(12) United States Patent
Harats et al.

(10) Patent No.: US 7,973,023 B2
(45) Date of Patent: *Jul. 5, 2011

(54) OXIDIZED LIPIDS AND USES THEREOF IN THE TREATMENT OF INFLAMMATORY DISEASES AND DISORDERS

(75) Inventors: Dror Harats, Ramat-Gan (IL); Jacob George, Tel-Aviv (IL); Gideon Halperin, Har-Adar (IL); Itzhak Mendel, Rechovot (IL); Niva Yacov, Tel-Aviv (IL); Eti Kovalevski-Ishai, Netania (IL)

(73) Assignee: Vascular Biogenics Ltd., OrYehuda (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/588,371

(22) Filed: Oct. 14, 2009

(65) Prior Publication Data

US 2010/0048515 A1    Feb. 25, 2010

Related U.S. Application Data

(60) Division of application No. 11/528,657, filed on Sep. 28, 2006, now Pat. No. 7,625,882, which is a continuation-in-part of application No. 10/567,543, filed as application No. PCT/IL2004/000453 on May 27, 2004, which is a continuation of application No. 10/445,347, filed on May 27, 2003, now Pat. No. 6,838,452.

(51) Int. Cl.
    *A61K 31/66* (2006.01)
(52) U.S. Cl. ........................................ 514/114
(58) Field of Classification Search ............... 514/114; 558/169
    See application file for complete search history.

(56) References Cited

U.S. PATENT DOCUMENTS

| | | | |
|---|---|---|---|
| 4,329,302 A | 5/1982 | Hanahan et al. | |
| 4,410,237 A | 10/1983 | Veldkamp | |
| 4,614,796 A | 9/1986 | Kawamata et al. | |
| 4,711,512 A | 12/1987 | Upatnieks | |
| 4,827,011 A | 5/1989 | Wissner et al. | |
| 5,061,626 A * | 10/1991 | Baldo et al. ................ | 435/174 |
| 5,082,629 A | 1/1992 | Burgess et al. | |
| 5,091,527 A | 2/1992 | Junius et al. | |
| 5,224,198 A | 6/1993 | Jachimowicz et al. | |
| 5,237,451 A | 8/1993 | Saxe | |
| 5,660,855 A | 8/1997 | Malé-Brune | |
| 5,742,262 A | 4/1998 | Tabata et al. | |
| 5,747,340 A | 5/1998 | Harats et al. | |
| 5,761,177 A | 6/1998 | Muneyoshi et al. | |
| 5,835,661 A | 11/1998 | Tai et al. | |
| 5,962,437 A | 10/1999 | Kucera et al. | |
| 6,580,529 B1 | 6/2003 | Amitai et al. | |
| 6,611,385 B2 | 8/2003 | Song | |
| 6,805,490 B2 | 10/2004 | Levola | |
| 6,822,770 B1 | 11/2004 | Takeyama | |
| 6,833,955 B2 | 12/2004 | Niv | |
| 6,838,452 B2 | 1/2005 | Harats et al. | |
| 7,206,107 B2 | 4/2007 | Levola | |
| 7,504,388 B2 * | 3/2009 | Harats et al. ................ | 514/114 |
| 2002/0102241 A1 | 8/2002 | Arnaout et al. | |
| 2002/0158131 A1 | 10/2002 | Dickson et al. | |
| 2003/0040509 A1 | 2/2003 | Moskowitz | |
| 2003/0067685 A1 | 4/2003 | Niv | |
| 2003/0202247 A1 | 10/2003 | Niv et al. | |
| 2003/0225035 A1 | 12/2003 | Harats et al. | |
| 2004/0051957 A1 | 3/2004 | Liang | |
| 2004/0106677 A1 | 6/2004 | Harats et al. | |
| 2005/0026023 A1 | 2/2005 | Hirai et al. | |
| 2005/0201693 A1 | 9/2005 | Korenaga et al. | |
| 2005/0272813 A1 | 12/2005 | Harats et al. | |
| 2006/0056028 A1 | 3/2006 | Wildnauer | |
| 2006/0126179 A1 | 6/2006 | Levola | |
| 2006/0194765 A1 | 8/2006 | Garcia et al. | |
| 2007/0065942 A1 | 3/2007 | Wandinger-Ness et al. | |
| 2007/0099868 A1 | 5/2007 | Harats et al. | |
| 2008/0261865 A1 | 10/2008 | Harats et al. | |
| 2009/0209775 A1 | 8/2009 | Harats et al. | |

FOREIGN PATENT DOCUMENTS

| | | |
|---|---|---|
| CH | 642665 | 4/1984 |
| EP | 0121088 | 10/1984 |
| EP | 0142333 | 5/1985 |
| EP | 0184905 | 6/1986 |
| EP | 2019552 | 6/1991 |
| EP | 331167 | 7/1992 |
| EP | 1031870 | 8/2000 |
| EP | 1333308 | 8/2003 |
| EP | 1577872 | 9/2005 |
| ES | 2019552 | 6/1991 |
| JP | 60-104066 | 6/1985 |
| JP | 62-000094 | 1/1987 |
| JP | 62-030714 | 2/1987 |
| JP | 63-054386 | 3/1988 |
| JP | 63-135395 | 6/1988 |
| JP | 01-258691 | 10/1989 |
| JP | 02-048585 | 2/1990 |
| JP | 04-097201 | 3/1992 |

(Continued)

OTHER PUBLICATIONS

Response Dated Apr. 8, 2010 to Official Action of Mar. 9, 2010 From the US Patent and Trademark Office Re.: U.S. Appl. No. 10/567,543.
Response Dated Mar. 22, 2010 to Official Action of Feb. 24, 2010 From the US Patent and Trademark Office Re.: U.S. Appl. No. 12/371,930.
International Preliminary Examination Report Dated Jan. 14, 2005 From the International Preliminary Examining Authority Re.: Application No. PCT/US01/90720.
Office Action Dated Sep. 9, 2005 From the Patent Office of the People's Republic of China Re.: Application No. 01822215.3.
Office Action Dated Jan. 14, 2008 From the Israeli Patent Office Re.: Application No. 176976.

(Continued)

*Primary Examiner* — Rei-tsang Shiao

(57) ABSTRACT

Novel synthetic oxidized lipids and methods utilizing oxidized lipids for treating and preventing an inflammation associated with an endogenous oxidized lipid are provided.

51 Claims, 38 Drawing Sheets
(15 of 38 Drawing Sheet(s) Filed in Color)

FOREIGN PATENT DOCUMENTS

| | | |
|---|---|---|
| JP | 06-230225 | 8/1994 |
| JP | 06-250022 | 9/1994 |
| JP | 07-258261 | 10/1995 |
| JP | 11-116563 | 4/1999 |
| JP | 2003-515550 | 5/2003 |
| RU | 1400511 | 5/1988 |
| WO | WO 87/05904 | 10/1987 |
| WO | WO 95/11473 | 4/1995 |
| WO | WO 95/23592 | 9/1995 |
| WO | WO 01/39744 | 6/2001 |
| WO | WO 01/75168 | 10/2001 |
| WO | WO 02/41827 | 5/2002 |
| WO | WO 03/032017 | 4/2003 |
| WO | WO 03/091763 | 11/2003 |
| WO | WO 2004/106486 | 12/2004 |
| WO | WO 2005/021738 | 3/2005 |
| WO | WO 2007/031991 | 3/2007 |
| WO | WO 2007/031992 | 3/2007 |
| WO | WO 2007/052265 | 5/2007 |
| WO | WO 2007/138576 | 12/2007 |
| WO | WO 2008/020450 | 2/2008 |
| WO | WO 2008/132729 | 11/2008 |

OTHER PUBLICATIONS

Office Action Dated Oct. 25, 2006 From the Israeli Patent Office Re.: Application No. 156015.
Official Action Dated Mar. 2, 2006 From the US Patent and Trademark Office Re.: U.S. Appl. No. 10/718,596.
Official Action Dated Nov. 25, 2008 From the US Patent and Trademark Office Re.: U.S. Appl. No. 11/528,657.
Communication Pursuant to Article 94(3) EPC Dated Nov. 9, 2009 From the European Patent Office Re.: Application No. 01997274.4.
Examination Report Dated Dec. 7, 2007 From the Instituto Mexican de la Propriedad Industrial Re.: Application No. PA/a/2005/012784.
Examiner's Report Dated Sep. 2, 2009 From the Australian Government, IP Australia Re.: Application No. 2004243695.
Examiner's Report Dated Aug. 15, 2005 From the Australian Government, IP Australia Re.: Application No. 2002218461.
Notice of Allowance Dated Nov. 3, 2008 From the US Patent and Trademark Office Re.: U.S. Appl. No. 11/183,884.
Notice of Allowance Dated Jun. 30, 2009 From the US Patent and Trademark Office Re.: U.S. Appl. No. 11/528,657.
Office Action Dated May 1, 2008 From the Israeli Patent Office Re.: Application No. 172165.
Office Action Dated Feb. 2, 2009 From the Government of India, Patent Office Re.: Application No. 3555/CHENP/2005.
Office Action Dated Aug. 12, 2008 From the Israeli Patent Office Re.: Application No. 172165.
Office Action Dated Jan. 14, 2008 From the Israeli Patent Office Re.: Application No. 172165.
Office Action Dated Oct. 17, 2008 From the State Intellectual Property Office of the People's Republic of China Re.: Application No. 01822215.3 and Its Translation Into English.
Office Action Dated Mar. 20, 2006 From the Israeli Patent Office Re.: Application No. 156015.
Official Action Dated Dec. 7, 2007 From the US Patent and Trademark Office Re.: U.S. Appl. No. 11/183,884.
Official Action Dated Jul. 15, 2005 From the US Patent and Trademark Office Re.: U.S. Appl. No. 10/718,596.
Official Action Dated Apr. 16, 2008 From the US Patent and Trademark Office Re.: U.S. Appl. No. 11/183,884.
Official Action Dated Nov. 25, 2008 From the US Patent and Trademark Office Re.: U.S. Appl. No. 11/528,657.
Official Communication Dated Oct. 3, 2008 From the Mexican Institut of Industrial Property Re.: Application No. PA/a/2003/004517.
Official Communication Dated Dec. 7, 2007 From the Mexican Institut of Industrial Property Re.: Application No. PA/a/2005/012784.
Requisition by the Examiner Dated Sep. 22, 2008 From the Canadian Intellectual Property Office Re.: Application No. 2,429,817.
Supplementary European Search Report Dated Aug. 3, 2009 From the European Patent Office Re.: Application No. 01997274.4.
Supplementary Partial European Search Dated Aug. 5, 2009 From the European Patent Office Re.: Application No. 04735088.9.
Translation of the Examination Report Dated Oct. 3, 2006 From the Government of India, Patent Office Re.: Application No. 797/CHENP/2003.
Translation of the Examination Report Dated Feb. 25, 2008 From the Government of India, Patent Office Re.: Application No. 3555/CHENP/2005.
Translation of the Office Action Dated Jan. 4, 2008 From the Patent Office of the People's Republic of China Re.: Application No. 200480021217.5.
Translation of the Official Action Dated Apr. 27, 2007 From the Patent Office of the Russian Federation Re.: Application No. 2005140666/04(045293).
Translation of the Official Communication Dated Aug. 29, 2007 From the Korean Patent Office Re.: Application No. 2003-7006991.
Anonymous "Graphic CIE L*a*b* Calculator. Try the Color Metric Converter or the RGB Calculator", Applet, ColorEng Inc., Retrieved From the Internet: <URL:http://colorpro.com/info/tools/labcalc.htm>, 4 P., 2007.
Anonymous "TOPAS®: Thermoplastic Olefin Polymer of Amorphous Structure (COC). Cyclic Olefin Copolymer (COC)", Polyplastics, Retrieved From the Internet: URL:http://www.polyplastics.com/en/product/lines/topas/TOPAS.pdf, p. 1-7, 2008.
Berchthold et al. "Synthesis of Carboxyphospholipids", Chemistry and Physics of Lipids, 28(1): 55-60, 1981. CAPLUS Document No. 95:42295.
Boullier et al. "The Binding of Oxidized Low Density Lipoprotein to Mouse CD36 Is Mediated in Part by Oxidized Phospholipids That Are Associated With Both the Lipid and Protein Moieties of the Lipoprotein", The Journal of Biological Chemistry, 275(13): 9163-9169, 2000. p. 9163, 9164.
Cooney et al. "Combining Site Specificities of Rabbit Antibodies to Platelet-Activating Factor (PAF)", Molecular Immunology, 27(5): 405-412, 1990. Abstract.
Deigner et al. "Effect of Platelet Activating Factor on the Kinetics of LDL Oxidation In Vitro", FEBS Letters, XP025615837, 317(3): 202-206, Feb. 15, 1993. Abstract, p. 205-206.
Hoff et al. "Phospholipid Hydroxyaleknals: Biological and Chemical Properties of Specific Oxidized Lipids Present in Atherosclerotic Lesions", Arteriosclerosis, Thrombosis, and Vascular Biology, 23: 275-282, 2003. p. 276, Fig.1.
Itabe et al. "Oxidized Phosphatidylcholines That Modify Proteins. Analysis by Monoclonal Antibody Against Oxidized Low Density", The Journal of Biological Chemistry, XP002532604, 271(52): 33208-33217, Dec. 27, 1996. Abstract, p. 33216.
Itabe et al. "Preparation of Radioactive Aldehyde-Containing Phosphatidylcholine", Analytical Biochemistry, XP002532603, 285(1): 151-155, Oct. 1, 2000. Abstract, p. 152.
Kamido et al. "Lipid Ester-Bound Aldehydes Among Copper-Catalyzed Peroxidation Products of Human Plasma Lipoproteins", Journal of Lipid Research, XP002951008, 36(9): 1876-1886, Jan. 1, 1995. p. 1877, col. 2.
Karasawa et al. "Antibodies to Synthetic Platelet-Activating Factor (1-0-Alkyl-2-0-Acetyl-SN-Glycero-3-Phosphocholine) Analogs With Substituents at the SN-2 Position", Journal of Biochemistry, 110(5): 683-687, 1991. CAPLUS Document No. 116:39343.
Kern et al. "Stimulation of Monocytes and Platelets by Short-Chain Phosphatidylcholines With and Without Terminal Carboxyl Group", Biochimica et Biophysica Acta, XP000938800, 1394(1): 33-42, Jan. 1, 1998. CAPLUS Document No. 130:50286. p. 39, § 2, Table 2, p. 41.
Leitinger et al. "Structurally Similar Oxidized Phospholipids Differentially Regulate Endothelial Binding of Monocytes and Neutrophils", Proc. Natl. Acad. Sci. USA, XP002951991, 96(21): 12010-12015, 1999. Abstract, p. 12013-12014.
Macpherson et al. "Production and Characterization of Antibodies to Platelet-Activating Factor", Journal of Lipid Mediators, 5(1): 49-59,1992. CAPLUS Document No. 117:68162.
Nitta et al. "Phospholipase A2 Activity of Fcγ2b Receptors of Thioglycollate-Elicited Murine Peritoneal Macropharges", Journal of Leukocyte Biology, 36(4): 493-504, 1984. CAPLUS Document No. 102:4277.

Ota et al. "Complexes of ApoA-1 With Phosphatidylcholine Suppress Dysregulation of Arterial Tone by Oxidized LDL", The American Journal of Physiology, 273(3 Pt.2): H1215-H1222. 1997.

Podrez et al. "A Novel Family of Atherogenic Oxidized Phospholipids Promotes Macrophage Foam Cell Formation Via the Scavenger Receptor CD36 and Is Enriched in Atherosclerotic Lesions", The Journal of Biological Chemistry, 277(41): 38517-38523, 2002. Scheme 1 on p. 38519.

Podrez et al. "Identification of A Novel Family of Oxidized Phospholipids That Serve as Ligands for the Macrophage Scavenger Receptor CD36", The Journal of Biological Chemistry, 277(41): 38503-38516, 2002. Fig.1, Table 1.

Shaw et al. "Natural Antibodies With the T15 Idiotype May Act in Atherosclerosis, Apoptotic Clearance, and Protective Immunity," The Journal of Clinical Investigation, XP002904328, 105(12): 1731-1740, 2000. Database HCAPLUS 421919, 2000. RN: 121324-31-0.

Smal et al. "Production of Antibodies to Platelet Activating Factor", Molecular Immunology, 26(8): 711-719, 1989. CAPLUS Document No. 111:192750.

Subbanagounder et al. "Determinants of Bioactivity of Oxydized Phospholipids: Specific Oxidized Fatty Acyl Groups at the SN-2 Position," Arteriosclerosis, Thrombosis, and Vascular Biology, XP002951986, p. 2248-2254, Jan. 1, 2000. Abstract, p. 2249.

Subbanagounder et al. "Evidence That Phospholipid Oxidation Products and/or Platelet-Activating Factor Play An Important Role in Early Atherogenesis: In Vitro and In Vivo Inhibition by WEB 2086", Circulation Research, p. 311-318, 1999. p. 311-313, 317.

Subbanagounder et al. "Evidence That Phospholipid Oxidation Products and/or Platelet-Activating Factor Play An Important Role in Early Atherogenesis: In Vitro and In Vivo Inhibition by WEB 2086", Circulation Research, 85: 311-318, 1999. Compound 'PEIPC'.

Sun et al. "Novel Bioactive Phospholipid: Practical Total Syntheses of Products From the Oxidation of Arachidonic and Linoleic Esters of 2-Lysophosphatidylcholine", Journal of Organic Chemistry, XP002538422, 67(11): 3575-3584, 2002.

Sung et al. "Analog Micro-Optics Fabrication by Use of A Binary Phase Grating Mask", Micromachining Technology for Micro-Optics and Nano-Optics II, Proceedings of the SPIE, 5347(1): 62-70, 2004.

Thirstrup et al. "Diffractive Optical Coupling Element for Surface Plasmon Resonance Sensors", Sensors and Actuators B, 100(3): 298-308, 2004.

Tokumura et al. "Cardiovascular Effects of Lysophophatidic Acid and Its Structural Analogs in Rats", The Journal of Pharmacology and Experimental Therapeutics, 219(1): 219-222, 1981.

Wang et al. "A Facile Synthesis of An Aldehydic Analog of Platelet Activating Factor and Its Use in the Production of Specific Antibodies", Chemistry and Physics of Lipids, 55(3): 265-273, 1990. CAPLUS Document No. 114:40661.

Watson et al. "Structural Identification by Mass Spectrometry of Oxidized Phospholipids in Minimally Oxidized Low Density Lipoprotein That Induce Monocyte/Endothelial Interactions and Evidence for Their Presence In Vivo", Journal of Biological Chemistry, XP002904327, 272(21): 13597-13607, 1997. p. 13603.

Office Action Dated Jan. 14, 2010 From the Israel Patent Office Re.: Application No. 172165 and Its Translation Into English.

Office Action Dated Jan. 14, 2010 From the Israel Patent Office Re.: Application No. 176976 and Its Translation Into English.

Office Action Dated Jan. 22, 2010 From the State Intellectual Property Office of the People's Republic of China Re.: Application No. 200480021217.5 and Its Summary Into English.

Official Action Dated Mar. 9, 2010 From the US Patent and Trademark Office Re.: U.S. Appl. No. 10/567,543.

Official Action Dated Feb. 24, 2010 From the US Patent and Trademark Office Re.: U.S. Appl. No. 12/371,930.

AHC Media "BioWorld Today", The Daily Biotechnology Newspaper, AHC Media LLC, 21(3): 1-7, Jan. 6, 2010.

Bangari et al. "Current Strategies and Future Directions for Eluding Adenoviral Vector Immunity", Current Gene Therapy, 6(2): 215-226, Apr. 2006.

Boldin et al. "A Novel Protein That Interacts With the Death Domain of Fas/APO1 Contains A Sequence Motif Related to the Death Domain", The Journal of Biological Chemistry, 270(14): 7795-7798, Apr. 7, 1995.

ClinicalTrials "Study to Assess VB-201 in Patients With Psoriasis", ClinicaTrials.gov, 3 P., Jan. 21, 2010.

Goltsev et al. "CASH, A Novel Caspase Homologue With Death Effector Domains", The Journal of Biological Chemistry, 272(32): 19641-19644, Aug. 8, 1997.

Gorski et al. "Potentiation of the Antitumor Effect of Ionizing Radiation by Brief Concomitant Exposures to Angiostatin", Cancer Research, 58(24): 5686-5689, Dec. 15, 1998.

Itasaka et al. "Endostatin Blocks Endothelial Repopulation After Radiation Therapy", Proceedings of the American Association for Cancer Research, 44: 26, Abstract #115, Mar. 2003. Abstract.

Kolesnick et al. "Radiation and Ceramide-Induced Apoptosis", Oncogene, 22(37): 5897-5906, Sep. 1, 2003.

Micheau et al. "STAT-1-Independent Upregulation of FADD and Procaspase-3 and -8 in Cancer Cells Treated With Cytotoxic Drugs", Biochemical and Biophysical Research Communications, 256(3): 603-607, Mar. 24, 1999.

Nayak et al. "Progress and Prospects: Immune Responses to Viral Vectors", Gene Therapy, Advance Online Publication on Nov. 12, 2009. Abstract.

Shir et al. "Gene Therapy for Glioblastoma: Future Perspective for Delivery Systems and Molecular Targets", Cellular and Molecular Neurobiology, 21(6): 645-656, 2001.

Weissmann "Translating Stem and Progenitor Cell Biology to the Clinic: Barriers and Opportunities", Science, 287(5457): 1442-1446, 2000. Abstract.

Response Dated May 11, 2010 to Office Action of Jan. 22, 2010 From the State Intellectual Property Office of the People's Republic of China Re.: Application No. 200480021217.5.

Official Action Dated May 27, 2010 From the US Patent and Trademark Office Re.: U.S. Appl. No. 12/371,930.

Requisition by the Examiner Dated Feb. 5, 2010 From the Canadian Intellectual Property Office Re.: Application No. 2,429,817.

Response Dated Jun. 13, 2010 to Office Action of Jan. 14, 2010 From the Israel Patent Office Re.: Application No. 172165.

Response Dated Jun. 14, 2010 to Office Action of Jan. 14, 2010 From the Israel Patent Office Re. Application No. 176976.

Official Action Dated Jun. 15, 2010 From the US Patent and Trademark Office Re.: U.S. Appl. No. 10/567,543.

International Search Report Dated Jul. 11, 2002 From the International Searching Authority Re. Application No. PCT/IL01/01080.

Response Dated Sep. 22, 2003 to Written Opinion of Aug. 12, 2003 From the International Preliminary Examining Authority Re. Application No. PCT/IL01/01080.

Written Opinion Dated Aug. 12, 2003 From the International Preliminary Examining Authority Re. Application No. PCT/IL01/01080.

Dandona et al. "Metabolic Syndrome: A Comprehensive Perspective Based on Interactions Between Obesity, Diabetes, and Inflammation", Circulation, 111: 1448-1454, 2005.

Response Dated Jul. 28, 2010 to Requisition by the Examiner of Feb. 5, 2010 From the Canadian Intellectual Property Office Re.: Application No. 2,429,817.

Response Dated Aug. 24, 2010 to Official Action of May 27, 2010 From the US Patent and Trademark Office Re.: U.S. Appl. No. 12/371,930.

Response Dated Aug. 24, 2010 to Official Action of May 27, 2010 From the US Patent and Trademark Office Re.: U.S. Appl. No. 12/371,930.

Response Dated Aug. 30, 2010 to Examiner's Report of Sep. 2, 2009 From the Australian Government, IP Australia Re.: Application No. 2004243695.

Response Dated Sep. 14, 2010 to Official Action of Jun. 15, 2010 From the US Patent and Trademark Office Re.: U.S. Appl. No. 10/567,543.

Notice of Allowance Dated Nov. 3, 2010 From the US Patent and Trademark Office Re. U.S. Appl. No. 10/567,543.

Response Dated Nov. 1, 2010 to Examiner's Report of Sep. 2, 2009 From the Australian Government, IP Australia Re.: Application No. 2004243695.
Translation of Notice of the Reason for Rejection Dated Nov. 19, 2010 From the Korean Intellectual Property Office Re. Application No. 2005-7022741.
Response Dated Feb. 13, 2011 to Notice of the Reason for Rejection of Nov. 19, 2010 From the Korean Intellectual Property Office Re. Application No. 2005-7022741.

Translation of Notice of Reason for Rejection Dated Feb. 22, 2011 From the Japanese Patent Office Re. Application No. 2006-531006.
Pontsler et al. "Cyclooxygenase-2 Is induced in Monocytes by Peroxisome Proliferator Activated Receptor ? and Oxidized Alkyl Phospholipids From Oxidized Low Density Lipoprotein", The Journal of Biological Chemistry, 277(15): 13029-13036, Apr. 12, 2002.

* cited by examiner

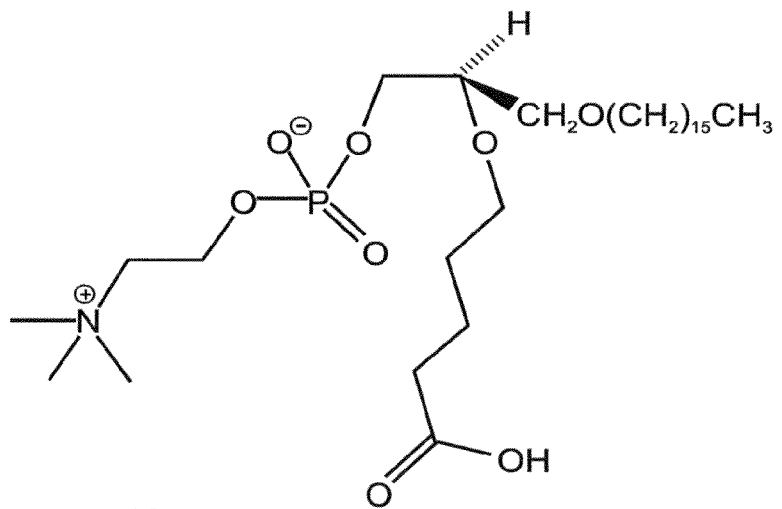
Compound VII (CI-201)
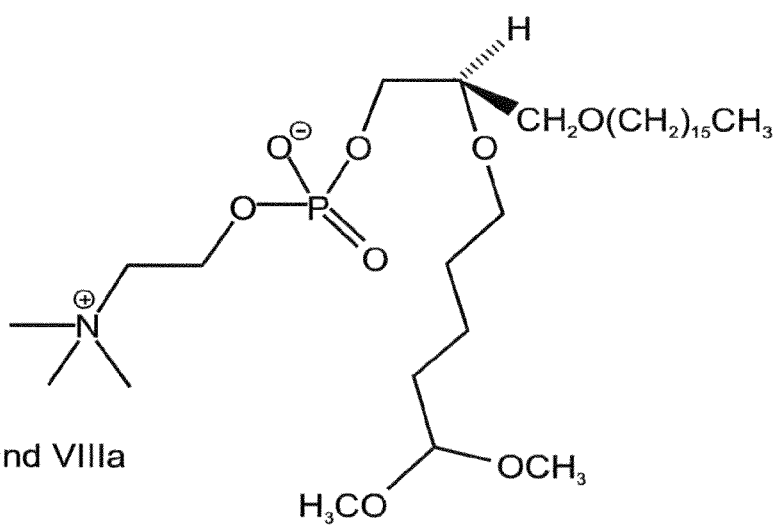
Compound VIIIa
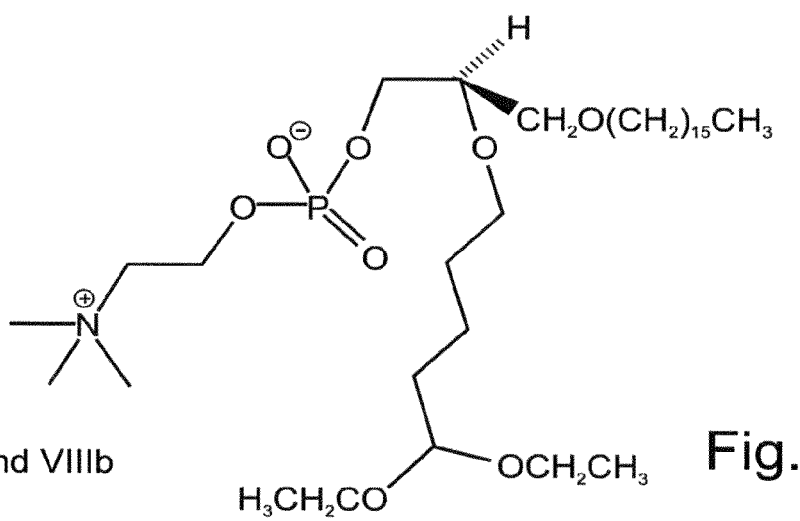
Compound VIIIb
Fig. 10

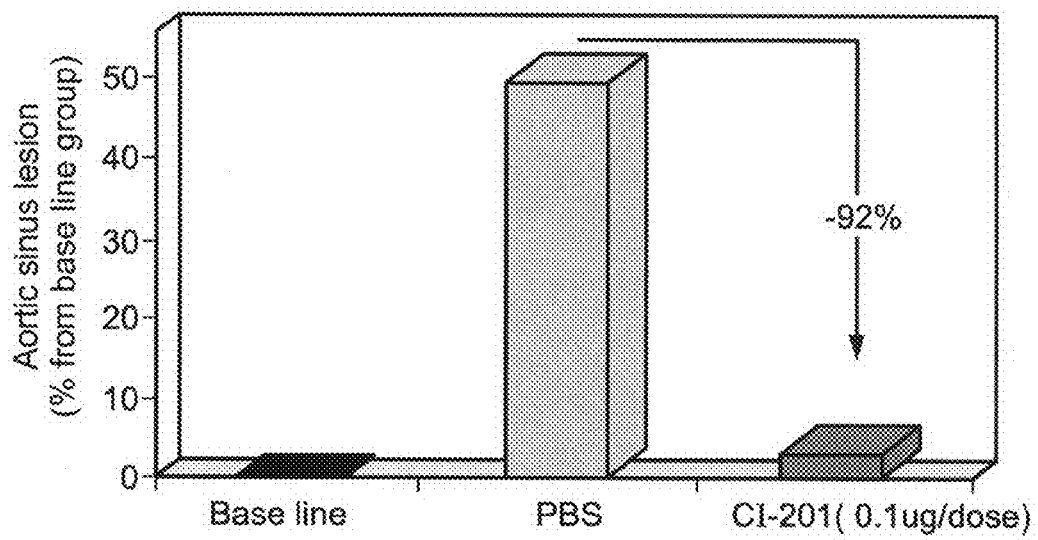
Fig. 14b
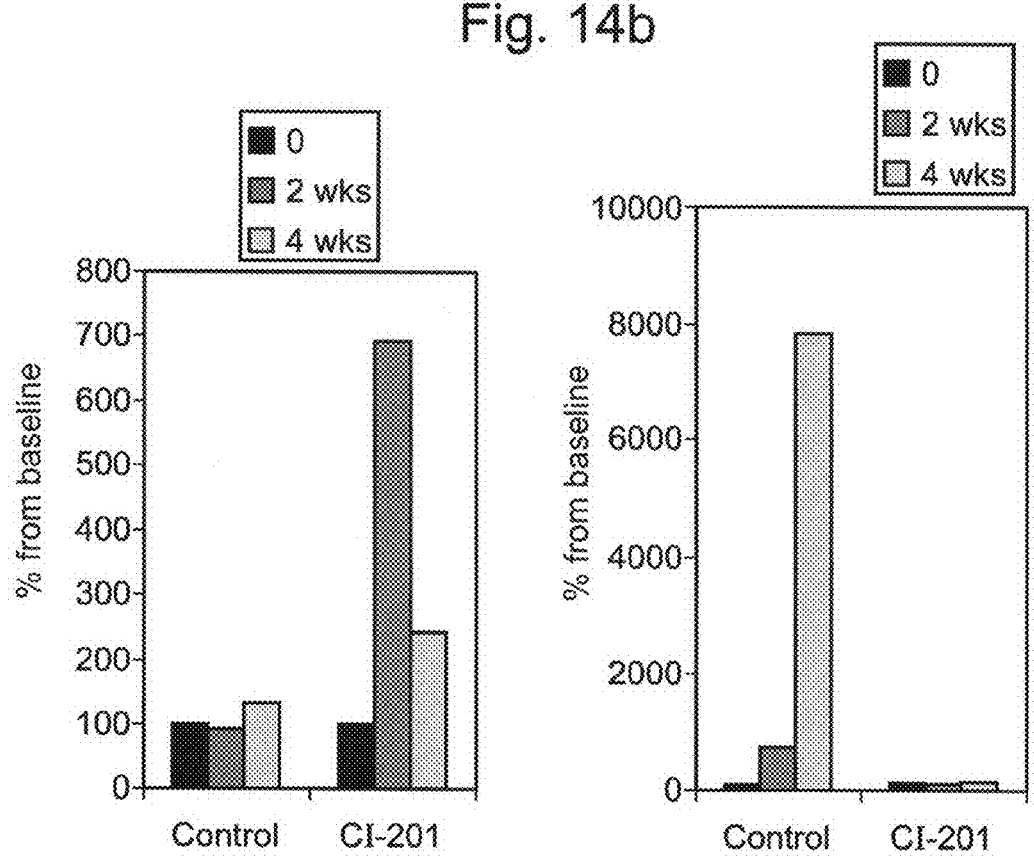
Fig. 15a
Fig. 15b

| Group | Dose mg/Kg B.W. | n= |
|---|---|---|
| A | 0 | 8 |
| B | 0.04 | 8 |
| C | 0.4 | 8 |
| D | 4 | 8 |

FIGs. 28g-l
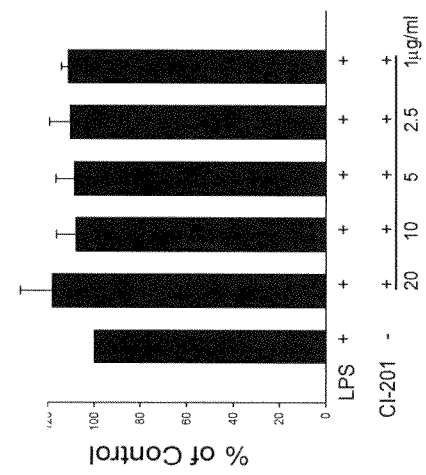
Fig. 28g
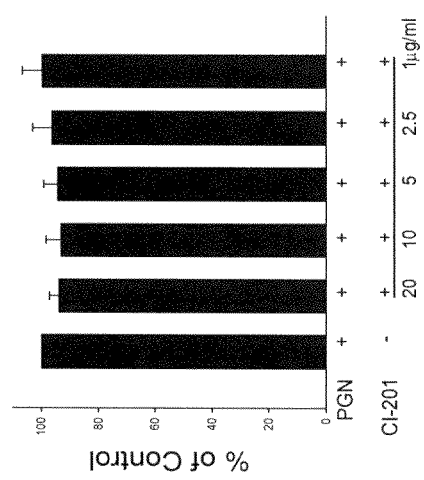
Fig. 28h
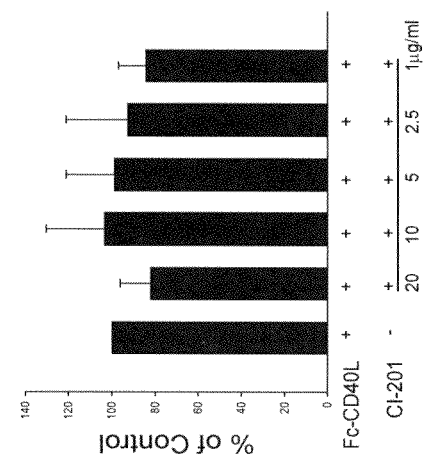
Fig. 28i
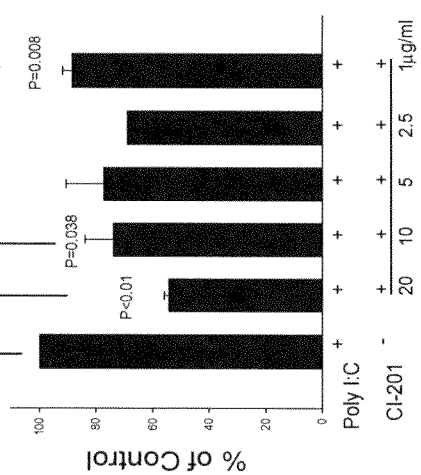
Fig. 28j
Fig. 28k
Fig. 28l

TNF-α:

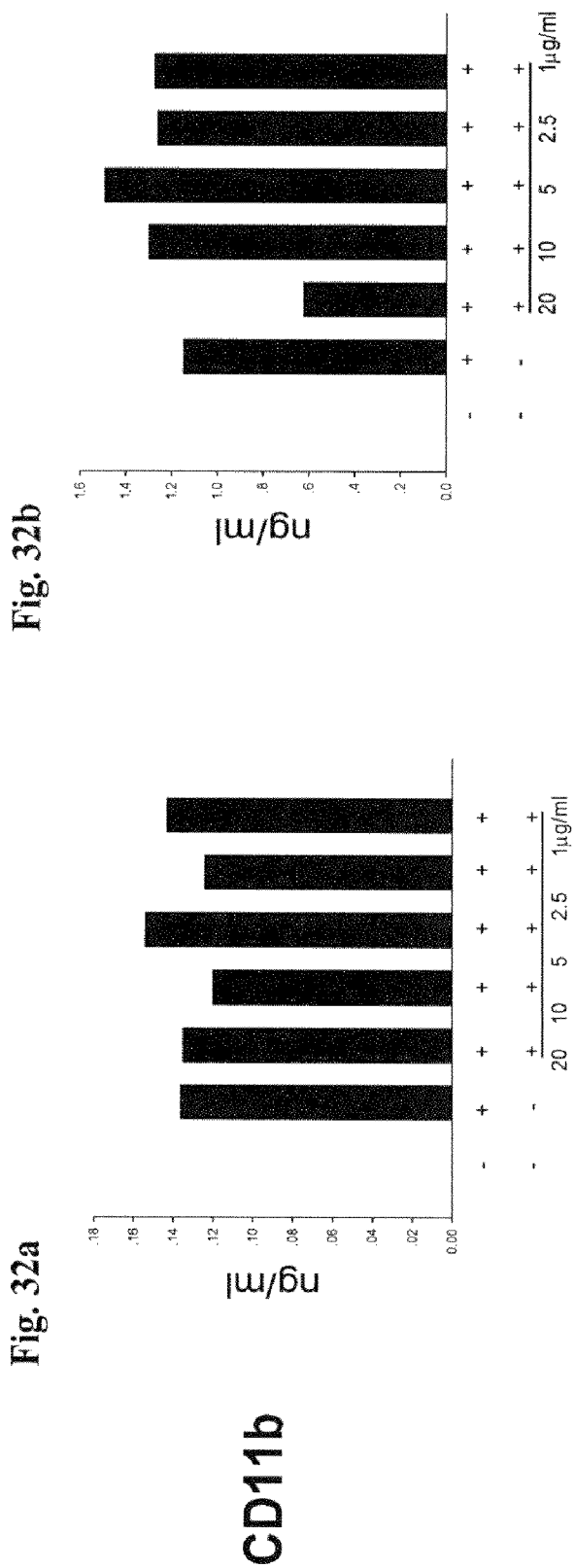
FIGs. 32a-b

Structure Function- Modified CI-201 molecules
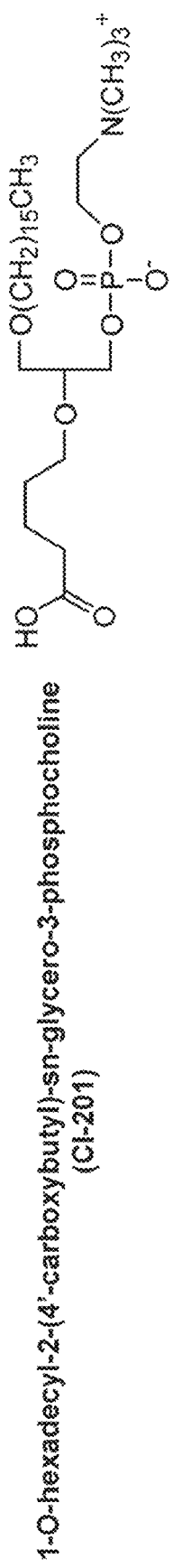
1-O-hexadecyl-2-(4'-carboxybutyl)-s

Structure Function- Modified CI-201 molecules
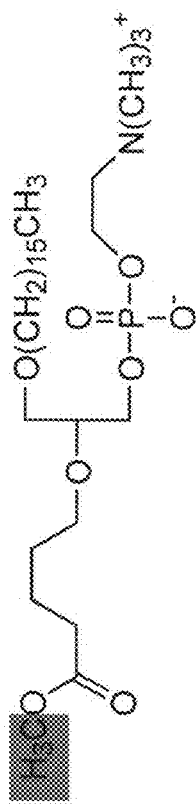
1-O-hexadecyl-2-(4'-carboxymethylester)-butyl-sn-glycero-3-phosphocholine (Methyl ester of CI-201)
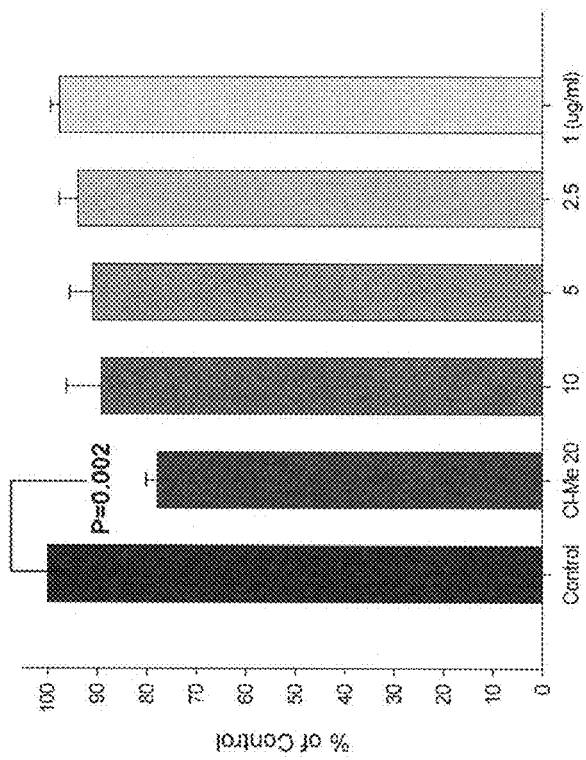

Structure Function- Modified CI-201 molecules
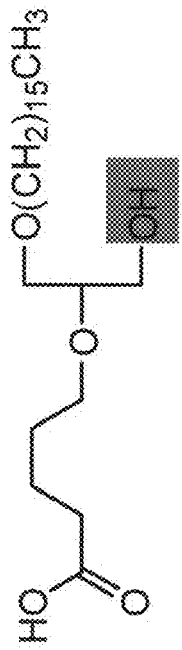
Non-phosphorylated metabolite of CI-201
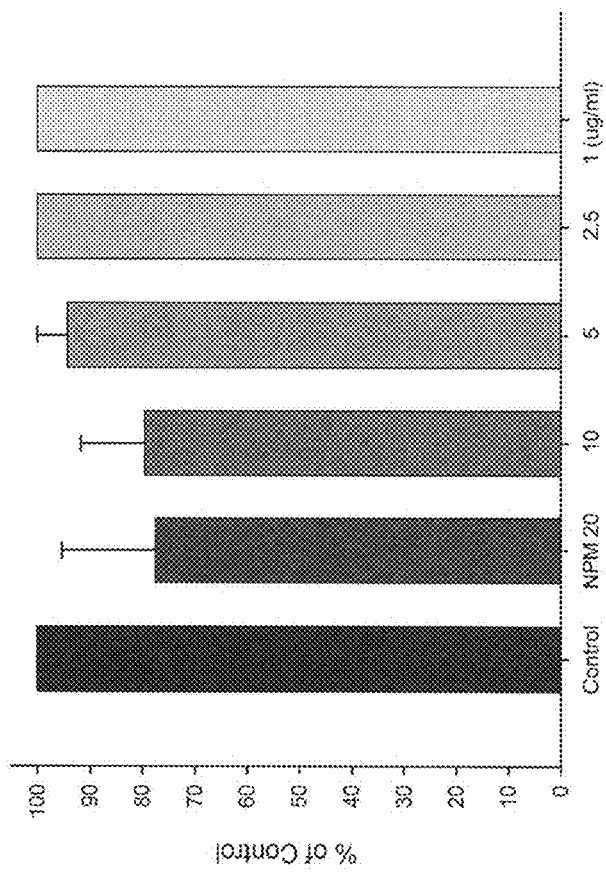
FIG. 33c

Structure Function- Modified Cl-201 molecules
Phosphoethanol amine of Cl-201
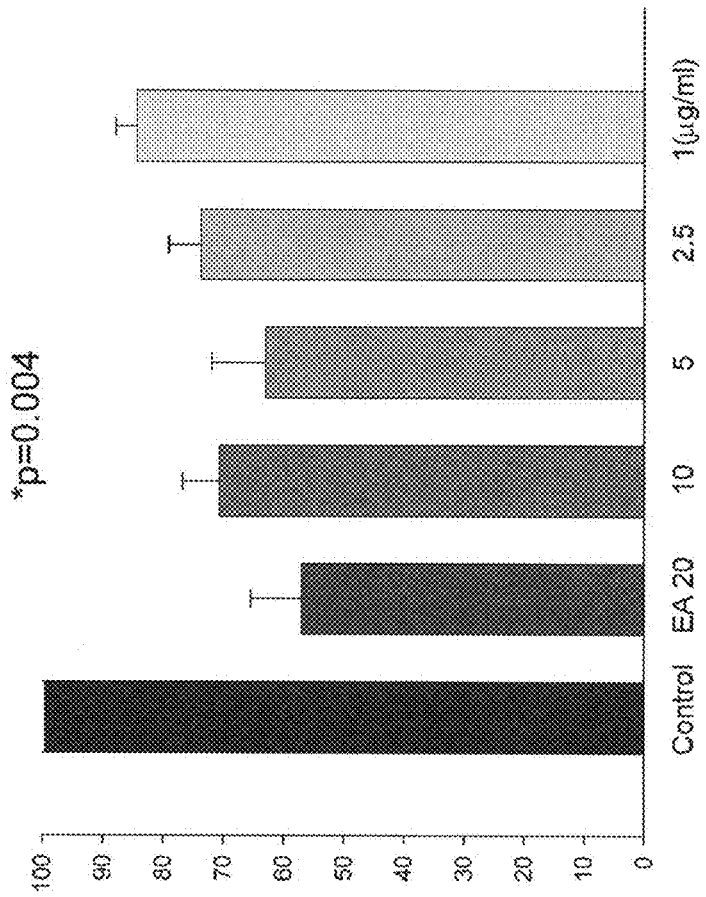
*p=0.004
FIG. 33d

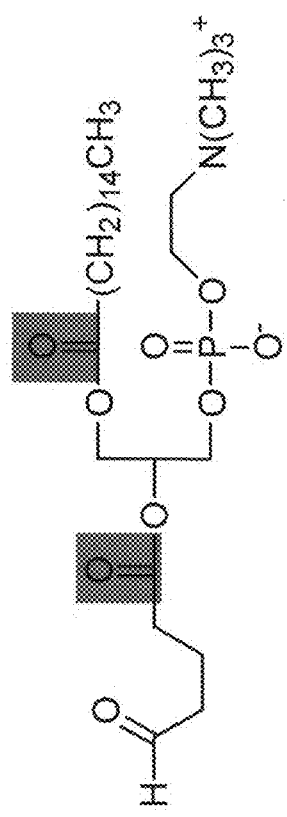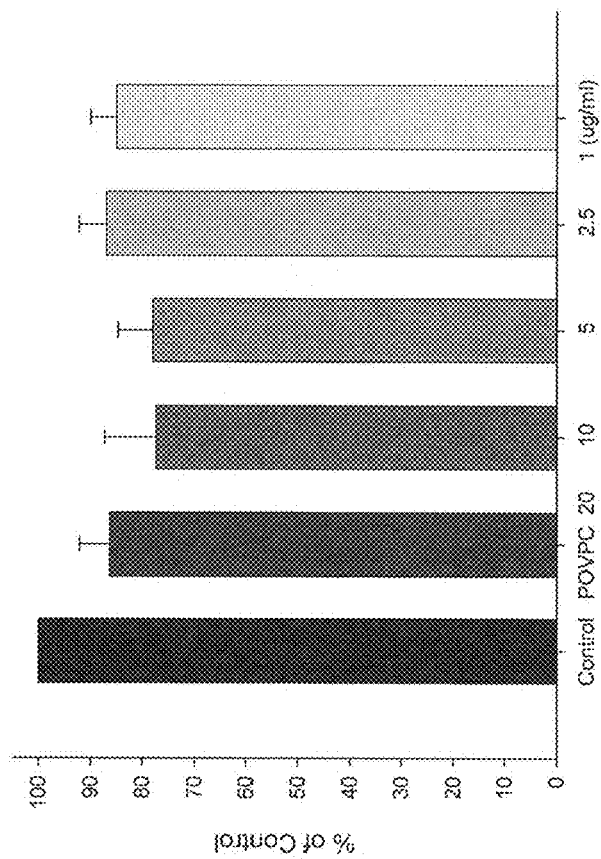
FIG. 33e

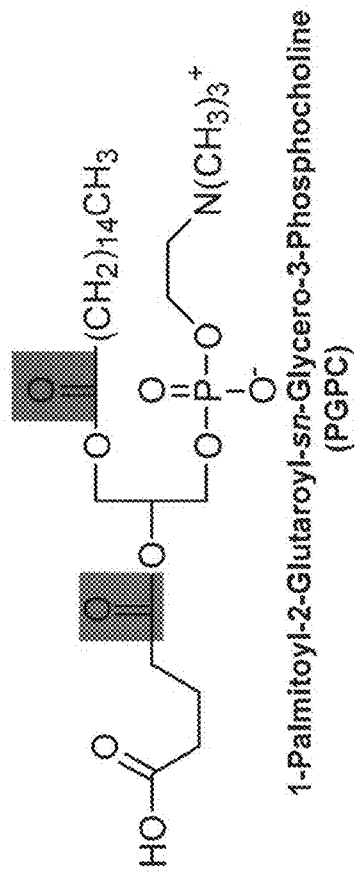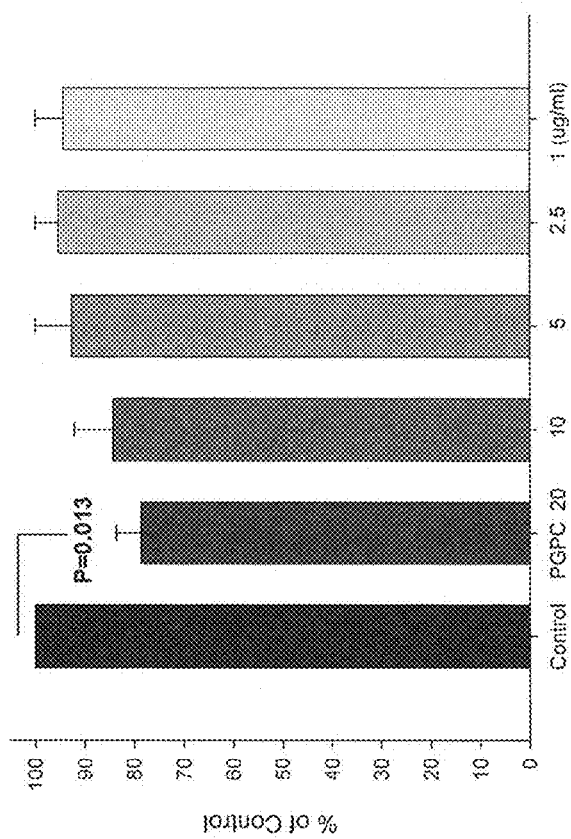
FIG. 33f

Structure Function- PAF like molecules
1-O-Hexadecyl-2-Acetoyl-sn-Glycero-3-Phosphocholine (PAF)
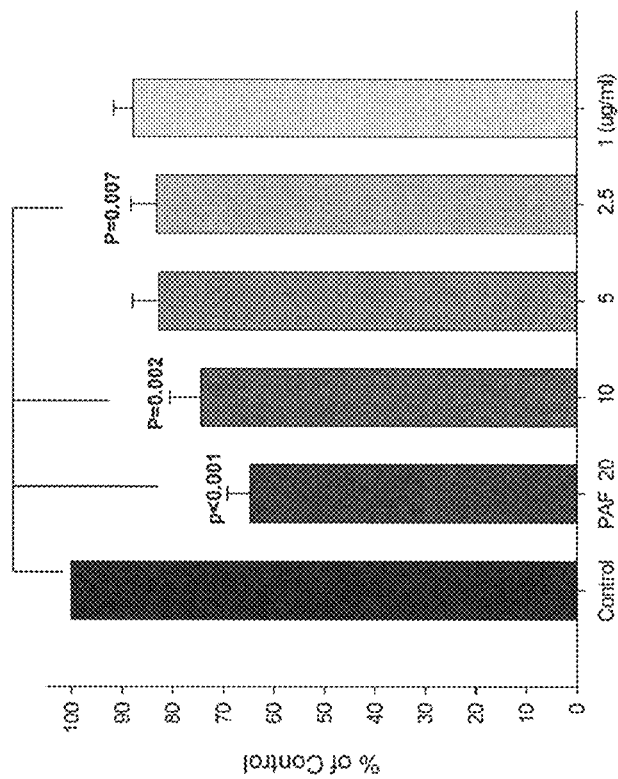
FIG. 33i

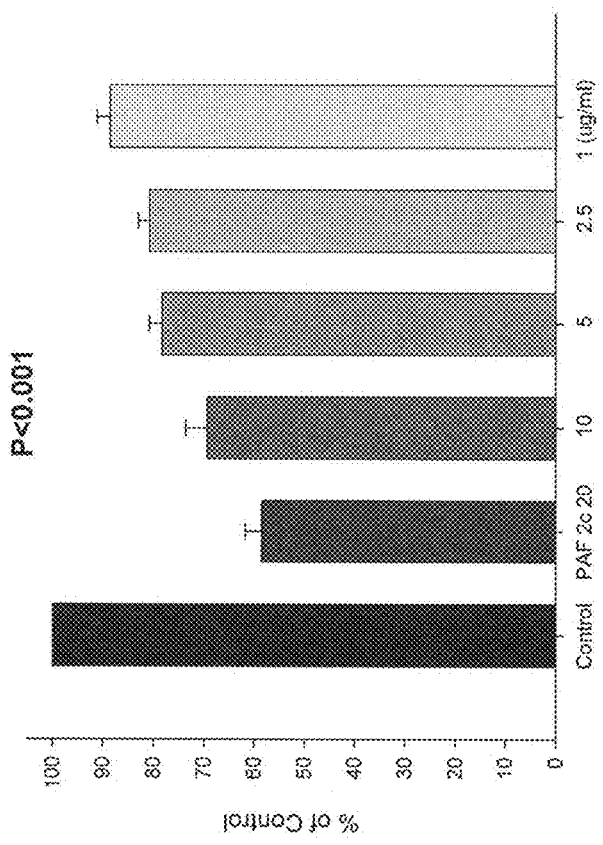
FIG. 33j

Structure Function- PAF like molecules
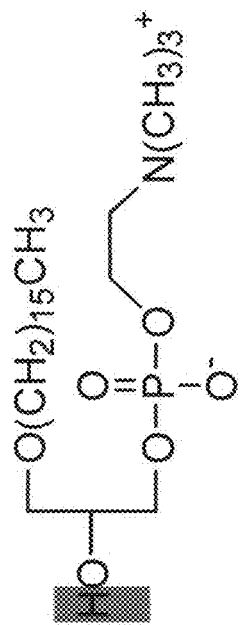
1-O-Hexadecyl-2-Hydroxy-sn-Glycero-3-Phosphocholine
(Lyso PAF)
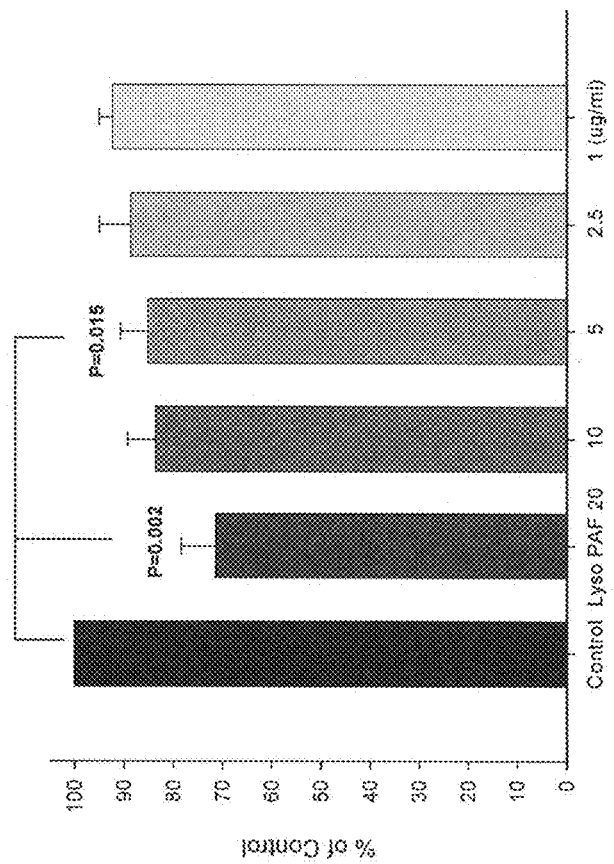
FIG. 33k

Structure Function- PAF like molecules
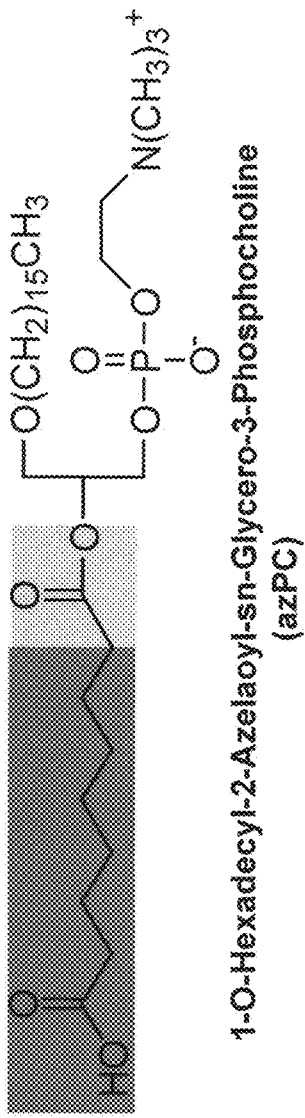
1-O-Hexadecyl-2-Azelaoyl-sn-Glycero-3-Phosphocholine
(azPC)
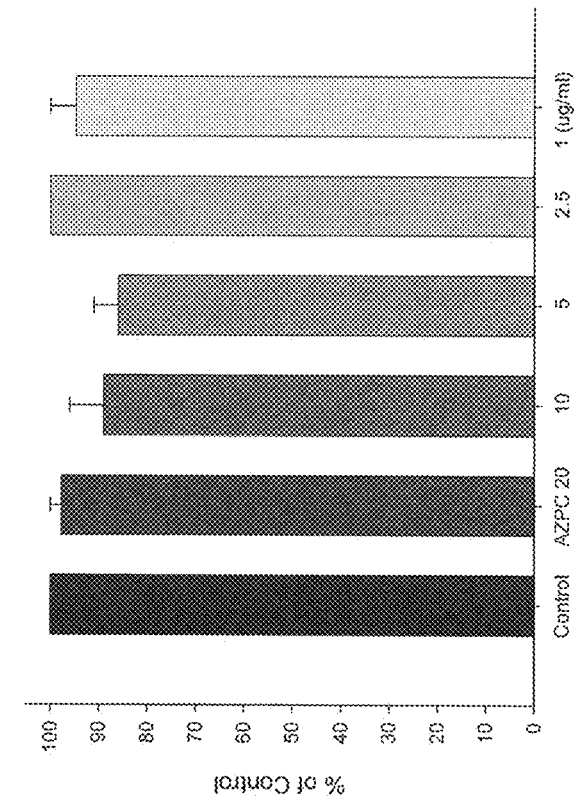
FIG. 33m

US 7,973,023 B2

OXIDIZED LIPIDS AND USES THEREOF IN THE TREATMENT OF INFLAMMATORY DISEASES AND DISORDERS

RELATED APPLICATIONS

This application is a divisional of pending U.S. patent application Ser. No. 11/528,657, filed on Sep. 28, 2006, which is a continuation-in-part of U.S. patent application Ser. No. 10/567,543, filed on Apr. 25, 2008, which is a National Phase of PCT Patent Application No. PCT/IL2004/000453, filed on May 27, 2004, which is a Continuation of U.S. patent application Ser. No. 10/445,347, filed on May 27, 2003, now U.S. Pat. No. 6,838,452 issued on Jan. 4, 2005. The contents of the above applications are all incorporated by reference.

FIELD AND BACKGROUND OF THE INVENTION

The present invention relates to novel oxidized lipids and to methods employing oxidized lipids for treating or preventing an inflammation associated with endogenous oxidized lipids. The methods of the present invention can be utilized in treating or preventing inflammation associated diseases and disorders such as, for example, atherosclerosis and related disorders, autoimmune diseases or disorders, and proliferative disease or disorders.

Cardiovascular disease is a major health risk throughout the industrialized world. Atherosclerosis, the most prevalent of cardiovascular diseases, is the principal cause of heart attack, stroke, and gangrene of the extremities, and as such, the principle cause of death in the United States. Atherosclerosis is a complex disease involving many cell types and molecular factors (for a detailed review, see Ross, 1993, Nature 362: 801-809). The process, which occurs in response to insults to the endothelium and smooth muscle cells (SMCs) of the wall of the artery, consists of the formation of fibrofatty and fibrous lesions or plaques, preceded and accompanied by inflammation. Plaque destabilization may lead to further complications such as rupture and thrombosis, which result from an excessive inflammatory-fibroproliferative response to numerous different forms of insults. For example, shear stresses are thought to be responsible for the frequent occurrence of atherosclerotic plaques in regions of the circulatory system where turbulent blood flow occurs, such as branch points and irregular structures.

The first observable event in the formation of an atherosclerotic plaque occurs when inflammatory cells such as monocyte-derived macrophages adhere to the vascular endothelial layer and transmigrate through to the sub-endothelial space. Elevated plasma LDL levels lead to lipid engorgement of the vessel walls, with adjacent endothelial cells producing oxidized low density lipoprotein (LDL). In addition, lipoprotein entrapment by the extracellular matrix leads to progressive oxidation of LDL by lipoxygenases, reactive oxygen species, peroxynitrite and/or myeloperoxidase. These oxidized LDL's are then taken up in large amounts by monocytes through scavenger receptors expressed on their surfaces.

Lipid-filled monocytes and smooth-muscle derived cells (SMCs) are called foam cells, and are the major constituent of the fatty streak. Interactions between foam cells, endothelial cells and smooth muscle cells surrounding them produce a state of chronic local inflammation which can eventually lead to activation of endothelial cells, increased macrophage apoptosis, smooth muscle cell proliferation and migration, and the formation of a fibrous plaque (Hajjar, D P and Haberland, M E, J. Biol Chem 1997 Sep. 12; 272(37):22975-78). Plaque rupture and thrombosis occlude the blood vessels concerned and thus restrict the flow of blood, resulting in ischemia, a condition characterized by a lack of oxygen supply in tissues of organs due to inadequate perfusion. When the involved arteries block the blood flow to the heart, a person is afflicted with a 'heart attack'; when the brain arteries occlude, the person experiences a stroke. When arteries to the limbs narrow, the result is severe pain, decreased physical mobility and possibly the need for amputation.

Oxidized LDL has been implicated in the pathogenesis of atherosclerosis and atherothrombosis, by its action on monocytes and smooth muscle cells, and by inducing endothelial cell apoptosis, impairing anticoagulant balance in the endothelium. Oxidized LDL also inhibits anti-atherogenic HDL-associated breakdown of oxidized phospholipids (Mertens, A and Holvoet, P, FASEB J 2001 October; 15(12):2073-84). This association is also supported by many studies demonstrating the presence of oxidized LDL in the plaques in various animal models of atherogenesis and the retardation of atherogenesis through inhibition of oxidation by pharmacological and/or genetic manipulations (see, for example, Witztum J and Steinberg, D, Trends Cardiovasc Med 2001 April-May; 11(3-4):93-102 for a review of current literature). Indeed, oxidized LDL and malondialdehyde (MDA)-modified LDL have been recently proposed as accurate blood markers for $1^{st}$ and $2^{nd}$ stages of coronary artery disease (U.S. Pat. Nos. 6,309,888, to Holvoet et al., and 6,255,070 to Witztum, et al.).

Reduction of LDL oxidation and activity has been the target of a number of suggested clinical applications for treatment and prevention of cardiovascular disease. Bucala, et al. (U.S. Pat. No. 5,869,534) discloses methods for the modulation of lipid peroxidation by reducing advanced glycosylation end product, lipid characteristic of age-, disease- and diabetes-related foam cell formation. Tang et al., at Incyte Pharmaceuticals, Inc. (U.S. Pat. No. 5,945,308) have disclosed the identification and proposed clinical application of a Human Oxidized LDL Receptor in the treatment of cardiovascular and autoimmune diseases and cancer.

Atherosclerosis and Autoimmune Disease

Because of the presumed role of the excessive inflammatory-fibroproliferative response in atherosclerosis and ischemia, a growing number of researchers have attempted to define an autoimmune component of vascular injury. In autoimmune diseases the immune system recognizes and attacks normally non-antigenic body components (autoantigens), in addition to attacking invading foreign antigens. The autoimmune diseases are classified as auto- (or self-) antibody mediated or cell mediated diseases. Typical autoantibody mediated autoimmune diseases are myasthenia gravis and idiopathic thrombocytopenic purpura (ITP), while typical cell mediated diseases are Hashimoto's thyroiditis and type I (Juvenile) Diabetes.

The recognition that immune mediated processes prevail within atherosclerotic lesions stemmed from the consistent observation of lymphocytes and macrophages in the earliest stages, namely the fatty streaks. These lymphocytes which include a predominant population of CD4+ cells (the remainder being CD8+ cells) were found to be more abundant over macrophages in early lesions, as compared with the more advanced lesions, in which this ratio tends to reverse. These findings posed questions as to whether they reflect a primary immune sensitization to a possible antigen or alternatively stand as a mere epiphenomenon of a previously induced local tissue damage. Regardless of the factors responsible for the recruitment of these inflammatory cells to the early plaque, they seem to exhibit an activated state manifested by concomitant expression of MHC class II HLA-DR and interleukin (IL) receptor as well as leukocyte common antigen (CD45R0) and the very late antigen 1 (VLA-1) integrin.

The on-going inflammatory reaction in the early stages of the atherosclerotic lesion may either be the primary initiating event leading to the production of various cytokines by the local cells (i.e. endothelial cells, macrophages, smooth muscle cells and inflammatory cells), or it may be that this reaction is a form of the body's defense immune system towards the hazardous process. Some of the cytokines which have been shown to be upregulated by the resident cells include TNF-α, IL-1, IL-2, IL-6, IL-8, IFN-γ and monocyte chemoattractant peptide-1 (MCP-1). Platelet derived growth factor (PDGF) and insulin-like growth factor (IGF) which are expressed by all cellular constituents within atherosclerotic plaques have also been shown to be overexpressed, thus possibly intensifying the preexisting inflammatory reaction by a co-stimulatory support in the form of a mitogenic and chemotactic factor. Recently, Uyemura et al. (Cross regulatory roles of IL-12 and IL-10 in atherosclerosis. J Clin Invest 1996 97; 2130-2138) have elucidated type 1 T-cell cytokine pattern in human atherosclerotic lesions exemplified by a strong expression of IFN-γ but not IL-4 mRNA in comparison with normal arteries. Furthermore, IL-12- a T-cell growth factor produced primarily by activated monocytes and a selective inducer of Th1 cytokine pattern, was found to be overexpressed within lesions as manifested by the abundance of its major heterodimer form p70 and p40 (its dominant inducible protein) mRNA.

Similar to the strong evidence for the dominance of the cellular immune system within the atherosclerotic plaque, there is also ample data supporting the involvement of the local humoral immune system. Thus, deposition of immunoglobulins and complement components have been shown in the plaques in addition to the enhanced expression of the C3b and C3Bi receptors in resident macrophages.

Valuable clues with regard to the contribution of immune mediated inflammation to the progression of atherosclerosis come from animal models. Immunocompromised mice (class I MHC deficient) tend to develop accelerated atherosclerosis as compared with immune competent mice. Additionally, treatment of C57BL/6 mice (Emeson E E, Shen M L. Accelerated atherosclerosis in hyperlipidemic C57BL/6 mice treated with cyclosporin A. Am J Pathol 1993; 142: 1906-1915) and New-Zealand White rabbits (Roselaar S E, Schonfeld G, Daugherty A. Enhanced development of atherosclerosis in cholesterol fed rabbits by suppression of cell mediated immunity. J Clin Invest 1995; 96: 1389-1394) with cyclosporin A, a potent suppressor of IL-2 transcription resulted in a significantly enhanced atherosclerosis under "normal" lipoprotein "burden". These latter studies may provide insight into the possible roles of the immune system in counteracting the self-perpetuating inflammatory process within the atherosclerotic plaque.

Atherosclerosis is not a classical autoimmune disease, although some of its manifestations such as the production of the plaque which obstructs the blood vessels may be related to aberrant immune responsiveness. In classical autoimmune disease, one can often define very clearly the sensitizing autoantigen attacked by the immune system and the component(s) of the immune system which recognize the autoantigen (humoral, i.e. autoantibody or cellular, i.e. lymphocytes). Above all, one can show that by passive transfer of these components of the immune system the disease can be induced in healthy animals, or in the case of humans the disease may be transferred from a sick pregnant mother to her offspring. Many of the above are not prevailing in atherosclerosis. In addition, the disease definitely has common risk factors such as hypertension, diabetes, lack of physical activity, smoking and others, the disease affects elderly people and has a different genetic preponderance than in classical autoimmune diseases.

Treatment of autoimmune inflammatory disease may be directed towards suppression or reversal of general and/or disease-specific immune reactivity. Thus Aiello, for example (U.S. Pat. Nos. 6,034,102 and 6,114,395) discloses the use of estrogen-like compounds for treatment and prevention of atherosclerosis and atherosclerotic lesion progression by inhibition of inflammatory cell recruitment. Similarly, Medford et al. (U.S. Pat. No. 5,846,959) disclose methods for the prevention of formation of oxidized PUFA, for treatment of cardiovascular and non-cardiovascular inflammatory diseases mediated by the cellular adhesion molecule VCAM-1. Furthermore, Falb (U.S. Pat. No. 6,156,500) designates a number of cell signaling and adhesion molecules abundant in atherosclerotic plaque and disease as potential targets of anti-inflammatory therapies.

Since oxidized LDL has been clearly implicated in the pathogenesis of atherosclerosis (see above), the contribution of these prominent plaque components to autoimmunity in atheromatous disease processes has been investigated.

Immune responsiveness to Oxidized LDL It is known that oxidized LDL (Ox LDL) is chemotactic for T-cells and monocytes. Ox LDL and its byproducts are also known to induce the expression of factors such as monocyte chemotactic factor 1, secretion of colony stimulating factor and platelet activating properties, all of which are potent growth stimulants.

The active involvement of the cellular immune response in atherosclerosis has recently been substantiated by Stemme S., et al. (Proc Natl Acad Sci USA 1995; 92: 3893-97), who isolated CD4+ within plaques clones responding to Ox LDL as stimuli. The clones corresponding to Ox LDL (4 out of 27) produced principally interferon-γ rather than IL-4. It remains to be seen whether the above T-cell clones represent mere contact with the cellular immune system with the inciting strong immunogen (Ox LDL) or that this reaction provides means of combating the apparently indolent atherosclerotic process.

The data regarding the involvement of the humoral mechanisms and their meaning are much more controversial. One recent study reported increased levels of antibodies against MDA-LDL, a metabolite of LDL oxidation, in women suffering from heart disease and/or diabetes (Dotevall, et al., Clin Sci 2001 November; 101(5): 523-31). Other investigators have demonstrated antibodies recognizing multiple epitopes on the oxidized LDL, representing immune reactivity to the lipid and apolipoprotein components (Steinerova A., et al., Physiol Res 2001; 50(2): 131-41) in atherosclerosis and other diseases, such as diabetes, renovascular syndrome, uremia, rheumatic fever and lupus erythematosus. Several reports have associated increased levels of antibodies to Ox LDL with the progression of atherosclerosis (expressed by the degree of carotid stenosis, severity of peripheral vascular disease etc.). Most recently, Sherer et al. (Cardiology 2001; 95(1):20-4) demonstrated elevated levels of antibodies to cardiolipin, beta 2GPI and OxLDL, in coronary heart disease. Thus, there seems to be a consensus as to the presence of Ox LDL antibodies in the form of immune complexes within atherosclerotic plaque, although the true significance of this finding has not been established.

Antibodies to Ox LDL have been hypothesized as playing an active role in lipoprotein metabolism. Thus, it is known that immune complexes of Ox LDL and its corresponding antibodies are taken up more efficiently by macrophages in suspension as compared with Ox LDL. No conclusions can be drawn from this consistent finding on the pathogenesis of atherosclerosis since the question of whether the accelerated uptake of Ox LDL by the macrophages is beneficial or deleterious has not yet been resolved.

Important data as to the significance of the humoral immune system in atherogenesis comes from animal models. It has been found that hyperimmunization of LDL-receptor deficient rabbits with homologous oxidized LDL, resulted in the production of high levels of anti-Ox LDL antibodies and was associated with a significant reduction in the extent of atherosclerotic lesions as compared with a control group exposed to phosphate-buffered saline (PBS). A decrease in plaque formation has also been accomplished by immunization of rabbits with cholesterol rich liposomes with the concomitant production of anti-cholesterol antibodies, yet this effect was accompanied by a 35% reduction in very low density lipoprotein cholesterol levels.

Thus, both the pathogenic role of oxidized LDL components and their importance as autoantigens in atherosclerosis, as well as other diseases, have been extensively demonstrated in laboratory and clinical studies.

Mucosal-Mediated Immunomodulation in Treatment of Autoimmune Disease

Recently, new methods and pharmaceutical formulations have been found that are useful for treating autoimmune diseases (and related T-cell mediated inflammatory disorders such as allograft rejection and retroviral-associated neurological disease). These treatments modulate the immune system by inducing tolerance, orally or mucosally, e.g. by inhalation, using as tolerizers autoantigens, bystander antigens, or disease-suppressive fragments or analogs of autoantigens or bystander antigens. Such treatments are described, for example, in U.S. Pat. No. 5,935,577 to Weiner et al. Autoantigens and bystander antigens are defined below (for a general review of mucosal tolerance see Nagler-Anderson, C., Crit Rev Immunol 2000; 20(2):103-20). Intravenous administration of autoantigens (and fragments thereof containing immunodominant epitopic regions of their molecules) has been found to induce immune suppression through a mechanism called clonal anergy. Clonal anergy causes deactivation of only immune attack T-cells specific to a particular antigen, the result being a significant reduction in the immune response to this antigen. Thus, the autoimmune response-promoting T-cells specific to an autoantigen, once anergized, no longer proliferate in response to that antigen. This reduction in proliferation also reduces the immune reactions responsible for autoimmune disease symptoms (such as neural tissue damage that is observed in MS). There is also evidence that oral administration of autoantigens (or immunodominant fragments) in a single dose and in substantially larger amounts than those that trigger "active suppression" may also induce tolerance through anergy (or clonal deletion).

A method of treatment has also been disclosed that proceeds by active suppression. Active suppression functions via a different mechanism from that of clonal anergy. This method, discussed extensively in PCT Application PCT/US93/01705, involves oral or mucosal administration of antigens specific to the tissue under autoimmune attack. These are called "bystander antigens". This treatment causes regulatory (suppressor) T-cells to be induced in the gut-associated lymphoid tissue (GALT), or bronchial associated lymphoid tissue (BALT), or most generally, mucosa associated lymphoid tissue (MALT) (MALT includes GALT and BALT). These regulatory cells are released in the blood or lymphatic tissue and then migrate to the organ or tissue afflicted by the autoimmune disease and suppress autoimmune attack of the afflicted organ or tissue. The T-cells elicited by the bystander antigen (which recognize at least one antigenic determinant of the bystander antigen used to elicit them) are targeted to the locus of autoimmune attack where they mediate the local release of certain immunomodulatory factors and cytokines, such as transforming growth factor beta (TGF-β), interleukin-4 (IL-4), and/or interleukin-10 (IL-10). Of these, TGF-β is an antigen-nonspecific immunosuppressive factor in that it suppresses immune attack regardless of the antigen that triggers the attack. (However, because oral or mucosal tolerization with a bystander antigen only causes the release of TGF-β in the vicinity of autoimmune attack, no systemic immunosuppression ensues.) IL-4 and IL-10 are also antigen-nonspecific immunoregulatory cytokines. IL-4 in particular enhances T helper type 2 ($Th_2$) response, i.e., acts on T-cell precursors and causes them to differentiate preferentially into $Th_2$ cells at the expense of $Th_1$ responses. IL-4 also indirectly inhibits $Th_1$ exacerbation. IL-10 is a direct inhibitor of $Th_1$ responses. After orally tolerizing mammals afflicted with autoimmune disease conditions with bystander antigens, increased levels of TGF-β, IL-4 and IL-10 are observed at the locus of autoimmune attack (Chen, Y. et al., Science, 265: 1237-1240, 1994). The bystander suppression mechanism has been confirmed by von Herreth et al., (J. Clin. Invest., 96:1324-1331, September 1996).

More recently, oral-mediated immunomodulation resulting in oral tolerance has been effectively applied in treatment of animal models of inflammatory bowel disease by feeding probiotic bacteria (Dunne, C, et al., Antonie Van Leeuwenhoek 1999 July-November; 76(1-4):279-92), autoimmune glomerulonephritis by feeding glomerular basement membrane (Reynolds, J. et al., J Am Soc Nephrol 2001 January; 12(1): 61-70) experimental allergic encephalomyelitis (EAE, which is the equivalent of multiple sclerosis or MS), by feeding myelin basic protein (MBP), adjuvant arthritis and collagen arthritis, by feeding a subject with collagen and HSP-65, respectively. A Boston based company called Autoimmune has carried out several human experiments for preventing diabetes, multiple sclerosis, rheumatoid arthritis and uveitis. The results of the human experiments have been less impressive than the non-human ones, however there has been some success with the prevention of arthritis.

Immunomodulation by induction of oral tolerance to autoantigens found in atherosclerotic plaque lesions has also been investigated. Study of the epitopes recognized by T-cells and Ig titers in clinical and experimental models of atherosclerosis indicated three candidate antigens for suppression of inflammation in atheromatous lesions: oxidized LDL, the stress-related heat shock protein HSP 65 and the cardiolipin binding protein beta 2GP1. U.S. patent application Ser. No. 09/806,400 to Shoenfeld et al. (filed Sep. 30, 1999), which is incorporated herein in its entirety, discloses the reduction by approximately 30% of atherogenesis in the arteries of genetically susceptible LDL-RD receptor deficient transgenic mice fed with oxidized human LDL. This protective effect, however, was achieved by feeding a crude antigen preparation consisting of centrifuged, filtered and purified human serum LDL which had been subjected to a lengthy oxidation process with $Cu^{++}$ or malondialdehyde (MDA). Although significant inhibition of atherogenesis was achieved, presumably via oral tolerance, no identification of specific lipid antigens or immunogenic LDL components was made. Another obstacle encountered was the inherent instability of the crude oxidized LDL in vivo, due to enzymatic activity and uptake of oxidized LDL by the liver and cellular immune mechanisms and its heterogeneity between different donors. It is plausible that a stable, more carefully defined oxidized LDL analog would have provided immunomodulation (e.g., by oral tolerance) of greater efficiency.

The induction of immune tolerance and subsequent prevention or inhibition of autoimmune inflammatory processes has been demonstrated using exposure to suppressive antigens via mucosal sites other than the gut. The membranous tissue around the eyes, and the mucosa of the nasal cavity, as well as the gut, are exposed to many invading as well as self-antigens and possess mechanisms for immune reactivity. Thus, Rossi, et al. (Scand J Immunol 1999 August; 50(2):177-82) found that nasal administration of gliadin was as effective as intravenous administration in downregulating the immune response to the antigen in a mouse model of celiac disease. Similarly, nasal exposure to acetylcholine receptor antigen was more effective than oral exposure in delaying and reducing muscle weakness and specific lymphocyte proliferation in a mouse model of myasthenia gravis (Shi, F D. et al., J Immunol 1999 May 15; 162 (10): 5757-63). Therefore, immunogenic compounds intended for mucosal as well as intravenous or intraperitoneal administration should optimally be adaptable to nasal and other membranous routes of administration.

Thus, there is clearly a need for novel, well defined, synthetic oxidized phospholipid derivatives and related substances exhibiting enhanced metabolic stability and efficient immunomodulation, induced by, e.g., oral, intravenous, intraperitoneal and mucosal administration.

Synthesis of Oxidized Phospholipids

Modification of phospholipids has been employed for a variety of applications. For example, phospholipids bearing lipid-soluble active compounds may be incorporated into compositions for trans-dermal and trans-membranal application (U.S. Pat. No. 5,985,292 to Fournerou et al.) and phospholipid derivatives can be incorporated into liposomes and biovectors for drug delivery (see, for example, U.S. Pat. Nos. 6,261,597 and 6,017,513 to Kurtz and Betbeder, et al., respectively, and U.S. Pat. No. 4,614,796). U.S. Pat. No. 5,660,855 discloses lipid constructs of aminomannose derivatized cholesterol suitable for targeting smooth muscle cells or tissue, formulated in liposomes. These formulations are aimed at reducing restenosis in arteries, using PTCA procedures. The use of liposomes for treating atherosclerosis has been further disclosed in WO 95/23592, to Hope and Rodrigueza, who teach pharmaceutical compositions of unilamellar liposomes that may contain phospholipids. The liposomes disclosed in WO 95/23592 are aimed at optimizing cholesterol efflux from atherosclerotic plaque and are typically non-oxidized phospholipids.

Modified phospholipid derivatives mimicking platelet activating factor (PAF) structure are known to be pharmaceutically active in variety of disorders and diseases, effecting such functions as vascular permeability, blood pressure, heart function inhibition etc. It has been suggested that one group of these derivatives may have anti cancerous activity (U.S. Pat. No. 4,778,912 to Inoue at al.). U.S. Pat. No. 4,329,302 teaches synthetic phosphoglycerides compounds—lysolechitin derivatives—that are usable in mediating platelet activation. While the compounds disclosed in U.S. Pat. No. 4,329,302 are either 1-O-alkyl ether or 1-O-fatty acyl phosphoglycerides, it was found that small chain acylation of lysolechitin gave rise to compounds with platelet activating behavior, as opposed to long-chain acylation, and that the 1-O-alkyl ether are biologically superior to the corresponding 1-O-fatty acyl derivatives in mimicking PAF.

The structural effect of various phospholipids on the biological activity thereof has also been investigated by Tokumura et al. (Journal of Pharmacology and Experimental Therapeutics. July 1981, Vol. 219, No. 1) and in U.S. Pat. No. 4,827,011 to Wissner et al., with respect to hypertension.

Another group of modified phospholipid ether derivatives has been disclosed in CH Pat. No. 642,665 to Berchtold. These modified phospholipid ether derivatives were found useful in chromatographic separation, but might have some physiological effect.

Oxidation of phospholipids occurs in vivo through the action of free radicals and enzymatic reactions abundant in atheromatous plaque. In vitro, preparation of oxidized phospholipids usually involves simple chemical oxidation of a native LDL or LDL phospholipid component. Investigators studying the role of oxidized LDL have employed, for example, ferrous ions and ascorbic acid (Itabe, H., et al., J. Biol. Chem. 1996; 271:33208-217) and copper sulfate (George, J. et al., Atherosclerosis. 1998; 138:147-152; Ameli, S. et al., Arteriosclerosis Thromb Vasc Biol 1996; 16:1074-79) to produce oxidized, or mildly oxidized phospholipid molecules similar to those associated with plaque components. Similarly prepared molecules have been shown to be identical to auto-antigens associated with atherogenesis (Watson A. D. et al., J. Biol. Chem. 1997; 272:13597-607) and able to induce protective anti-atherogenic immune tolerance (U.S. patent application Ser. No. 09/806,400 to Shoenfeld et al., filed Sep. 30, 1999) in mice. Likewise, Koike (U.S. Pat. No. 5,561,052) discloses a method of producing oxidized lipids and phospholipids using copper sulfate and superoxide dismutase to produce oxidized arachidonic or linoleic acids and oxidized LDL for diagnostic use. Davies et al. (J. Biol. Chem. 2001, 276:16015) teach the use of oxidized phospholipids as peroxisome proliferator-activated receptor agonists.

1-Palmitoyl-2-(5-oxovaleroyl)-sn-glycero-3-phosphocholine (POVPC, see Example I for a 2-D structural description) and derivatives thereof such as 1-palmitoyl-2-glutaroyl-sn-glycero-3-phosphocholine (PGPC) are representative examples of oxidized esterified phospholipids that have been studied with respect to atherogenesis (see, for example, Boullier et al., J. Biol. Chem. 2000, 275:9163; Subbanagounder et al., Circulation Research, 1999, pp. 311). The effect of different structural analogs that belong to this class of oxidized phospholipids has also been studied (see, for example, Subbanagounder et al., Arterioscler. Thromb. Nasc. Biol. 2000, pp. 2248; Leitinger et al., Proc. Nat. Ac. Sci. 1999, 96:12010).

However, in vivo applications employing oxidized phospholipids prepared as above have the disadvantage of susceptibility to recognition, binding and metabolism of the active component in the body, making dosage and stability after administration an important consideration.

Furthermore, the oxidation techniques employed are non-specific, yielding a variety of oxidized products, necessitating either further purification or use of impure antigenic compounds. This is of even greater concern with native LDL, even if purified.

Thus, there is a widely recognized need for, and it would be highly advantageous to have, a novel, synthetic oxidized phospholipid, improved methods of synthesizing same and uses thereof as immunomodulators, devoid of the above limitations.

SUMMARY OF THE INVENTION

According to one aspect of the present invention, there is provided a compound having the general formula I:

Formula I $$R'_1-C_1-B_1-A_1-X_1$$
$$R_2-C_2-B_2-A_2-X_2$$
$$R_{n-1}-C_{n-1}-B_{n-1}-A_{n-1}-X_{n-1}$$
$$R_n-C_n-B_n-Y$$

with $R_1$ on $C_1$ and $R'_n$ on $C_n$ wherein:

n is an integer of 1-6, whereas if n=1, Cn, Bn, Rn, R'n and Y are absent;

each of $B_1, B_2, \ldots Bn-1$ and Bn is independently selected from the group consisting of oxygen, sulfur, nitrogen, phosphor and silicon, whereby each of said nitrogen, phosphor and silicon is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo;

each of $A_1, A_2, \ldots An-1$ and An is independently selected from the group consisting of CR"R'", C=O and C=S;

Y is selected from the group consisting of hydrogen, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-biposphonate, pyrophosphate, phosphoethanolamine-diethylenetriamine-pentaacetate, dinitrophenyl-phosphoethanolamine and phsophoglycerol; and each of $X_1, X_2, \ldots Xn-1$ is independently a saturated or unsaturated hydrocarbon having the general formula II:

Formula II $$-C_a-C_b---C_{m-1}-C_m-Z;$$

with Ra, Rb, Rm-1, Rm on top and R'a, R'b, R'm-1, R'm on bottom wherein:

m is an integer of 1-26; and

Z is selected from the group consisting of:

H, $W=C\begin{smallmatrix}R''\\\\\end{smallmatrix}$, $W=C\begin{smallmatrix}R''\\O\\|\\OH\end{smallmatrix}$, $W=C\begin{smallmatrix}OR''\\\\\end{smallmatrix}$, $-CH\begin{smallmatrix}WR''\\WR'''\end{smallmatrix}$, and whereas:

W is selected from the group consisting of oxygen, sulfur, nitrogen and phosphor, whereby each of said nitrogen and phosphor is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo; and in at least one of $X_1, X_2, \ldots Xn-1$ Z is not hydrogen; and wherein:

each of $R_1, R'_1, R_2, \ldots Rn-1, Rn, R'n$, each of R" and R'" and each of Ra, R'a, Rb, R'b, \ldots Rm-1, R'm-1, Rm and R'm is independently selected from the group consisting of hydrogen, a bond, alkyl, alkenyl, alkylnyl, cycloalkyl, aryl, heteroaryl, heteroalicyclic, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, or, alternatively, at least two of R1, R'$_1$, R2, \ldots Rn-1, Rn and R'n and/or at least two of Ra, R'a, Rb, R'b, \ldots Rm-1, R'm-1, Rm and R'm form at least one four-, five- or six-membered aromatic, heteroaromatic, alicyclic or heteroalicyclic ring; and each of $C_1, C_2, \ldots, Cn-1, Cn$, and each of Ca, Cb, \ldots Cm-1 and Cm is a chiral or non-chiral carbon atom, whereby each chiral carbon atom has a S-configuration and/or a R-configuration, a pharmaceutically acceptable salt, a prodrug, a hydrate or a solvate thereof.

According to further features in preferred embodiments of the invention described below, at least one of $A_1, A_2, \ldots$ and An-1 is CR"R'", and at least one of these $A_1, A_2, \ldots$ and An-1 is linked to a $X_1, X_2 \ldots$ or Xn-1 which comprises a Z different than hydrogen.

According to still further features in the described preferred embodiments n equals 3 and at least one of $A_1$ and $A_2$ is CR"R'". Preferably, $A_2$ is CR"R'" and $X_2$ comprises a Z different than hydrogen. Further preferably, each of $A_1$ and $A_2$ is CR"R'".

According to still further features in the described preferred embodiments Z is selected from the group consisting of $$W=C\begin{smallmatrix}OR''\\\\\end{smallmatrix} \text{ and } -CH\begin{smallmatrix}WR''\\WR'''\end{smallmatrix},$$

whereby W is preferably oxygen and each of R" and R'" is independently selected from the group consisting of hydrogen and alkyl.

According to still further features in the described preferred embodiments n equals 1 and at least one of $R_1$ and $R'_1$ is a phosphate or a phosphonate.

According to still further features in the described preferred embodiments n equals 5 or 6 and at least one of $R_1, R'_1$ and at least one of Rn and R'n form at least one heteroalicyclic ring, e.g., a monosaccharide ring.

According to another aspect of the present invention there is provided a pharmaceutical composition comprising, as an active ingredient, the compound described hereinabove and a pharmaceutically acceptable carrier.

According to further features in preferred embodiments of the invention described below, the pharmaceutical composition is packaged in a packaging material and identified in print, in or on said packaging material, for use in the treatment or prevention of an inflammation associated with an endogenous oxidized lipid, as is detailed hereinbelow.

According to still further features in the described preferred embodiments, the pharmaceutical composition further comprises at least one additional compound capable of treating or preventing the inflammation associated with an endogenous oxidized lipid, as is detailed hereinbelow.

According to still another aspect of the present invention, there is provided a method of treating or preventing an inflammation associated with an endogenous oxidized lipid, which comprises administering to a subject in need thereof a therapeutically effective amount of at least one oxidized lipid, thereby treating or preventing the inflammation associated with an endogenous oxidized lipid in the subject.

According to still further features in the described preferred embodiments the oxidized lipid is selected from the group consisting of an oxidized phospholipid, a platelet activating factor, a plasmalogen, a substituted or unsubstituted 3-30 carbon atoms hydrocarbon terminating with an oxidized group, an oxidized sphingolipids, an oxidized glycolipid, an oxidized membrane lipid and any analog or derivative thereof.

According to still further features in the described preferred embodiments, the oxidized lipid has the general formula I depicted hereinabove.

According to still further features in the described preferred embodiments the oxidized lipid is selected from the group consisting of: 1-palmitoyl-2-azelaoyl-sn-glycero-3-phosphocholine, 1-hexadecyl-2-azelaoyl-sn-glycero-3-phosphocholine, 1-palmitoyl-2-glutaroyl-sn-glycero-3-phosphocholine (PGPC), 1-palmitoyl-2-(5-oxovaleroyl)-sn-glycero-3-phosphocholine (POVPC), 1-palmitoyl-2-(9-oxononanoyl)-sn-glycero-3-phosphocholine, 1-hexadecyl-2-acetoyl-sn-glycero-3-phosphocholine, 1-octadecyl-2-acetoyl-sn-glycero-3-phosphocholine, 1-hexadecyl-2-butyroyl-sn-glycero-3-phosphocholine, 1-octadecyl-2-butyroyl-sn-glycero-3-phosphocholine, 1-palmitoyl-2-acetoyl-sn-glycero-3-phosphocholine, 1-octadecenyl-2-acetoyl-sn-glycero-3-phosphocholine, 1-hexadecyl-2-(homogammalinolenoyl)-sn-glycero-3-phosphocholine, 1-hexadecyl-2-arachidonoyl-sn-glycero-3-phosphocholine, 1-hexadecyl-2-eicosapentaenoyl-sn-glycero-3-phosphocholine, 1-hexadecyl-2-docosahexaenoyl-sn-glycero-3-phosphocholine, 1-octadecyl-2-methyl-sn-glycero-3-phosphocholine, 1-hexadecyl-2-butenoyl-sn-glycero-3-phosphocholine, Lyso PAF C16, Lyso PAF C18, 1-O-1'-(Z)-hexadecenyl-2-[12-[(7-nitro-2-1,3-benzoxadiazol-4-yl)amino]dodecanoyl]-sn-glycero-3-phosphocholine, 1-O-1-(Z)-hexadecenyl-2-oleoyl-sn-glycero-3-phosphocholine, 1-O-1-(Z)-hexadecenyl-2-arachidonoyl-sn-glycero-3-phosphocholine, 1-O-1'-(Z)-hexadecenyl-2-docosahexaenoyl-sn-glycero-3-phosphocholine, 1-O-1-(Z)-hexadecenyl-2-oleoyl-sn-glycero-3-phosphoethanolamine, 1-O-1'-(Z)-hexadecenyl-2-arachidonoyl-sn-glycero-3-phosphoethanolamine, and 1-O-1'-(Z)-hexadecenyl-2-docosahexaenoyl-sn-glycero-3-phosphoethanolamine.

According to still further features in the described preferred embodiments, the method further comprises administering to the subject a therapeutically effective amount of at least one additional compound capable of treating or preventing an inflammation associated with endogenous oxidized LDL.

The at least one additional compound is preferably selected from the group consisting of a HMGCoA reductase inhibitor (a statin), a mucosal adjuvant, a corticosteroid, a steroidal anti-inflammatory drug, a non-steroidal anti-inflammatory drug, an analgesic, a growth factor, a toxin, a HSP, a Beta-2-glycoprotein I, a cholesteryl ester transfer protein (CETP) inhibitor, a perixosome proliferative activated receptor (PPAR) agonist, an anti-atherosclerosis drug, an anti-proliferative agent, ezetimide, nicotinic acid, a squalen inhibitor, an ApoE Milano, and any derivative and analog thereof.

The inflammation according to the present invention is associated with diseases and disorders such as, for example, idiopathic inflammatory diseases or disorders, chronic inflammatory diseases or disorders, acute inflammatory diseases or disorders, autoimmune diseases or disorders, infectious diseases or disorders, inflammatory malignant diseases or disorders, inflammatory transplantation-related diseases or disorders, inflammatory degenerative diseases or disorders, diseases or disorders associated with a hypersensitivity, inflammatory cardiovascular diseases or disorders, inflammatory cerebrovascular diseases or disorders, peripheral vascular diseases or disorders, inflammatory glandular diseases or disorders, inflammatory gastrointestinal diseases or disorders, inflammatory cutaneous diseases or disorders, inflammatory hepatic diseases or disorders, inflammatory neurological diseases or disorders, inflammatory musculo-skeletal diseases or disorders, inflammatory renal diseases or disorders, inflammatory reproductive diseases or disorders, inflammatory systemic diseases or disorders, inflammatory connective tissue diseases or disorders, inflammatory tumors, necrosis, inflammatory implant-related diseases or disorders, inflammatory aging processes, immunodeficiency diseases or disorders, proliferative diseases and disorders and inflammatory pulmonary diseases or disorders, as is detailed hereinbelow.

The present invention successfully addresses the shortcomings of the presently known configurations by providing novel synthetic oxidized lipids, devoid of the limitations associated with the presently known synthetic oxidized lipids and methods of treating or preventing an inflammation associated with an endogenous oxidized lipid utilizing synthetic oxidized lipids.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a flow chart depicting the synthesis of 2,5' Aldehyde lechitin ether, 1-hexadecyl-2-(5'-oxo-pentanyl)-sn-glycero-3-phosphocholine (for D-ALLE) or 3-hexadecyl-2-

(5'-oxo-pentanyl)-sn-glycero-1-phosphocholine (for L-ALLE) (ALLE), according to the synthesis method of the present invention.

Figure 2:
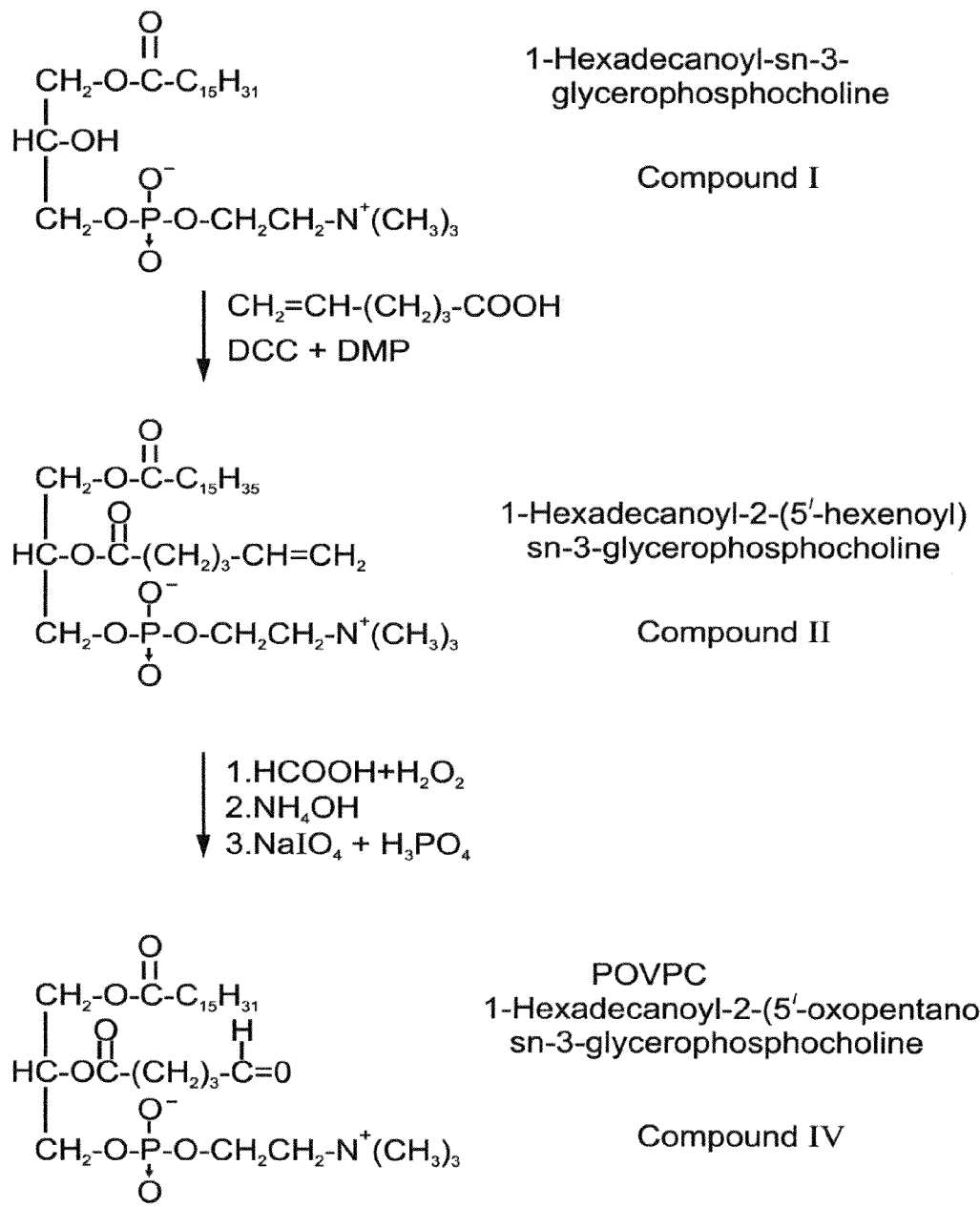

FIG. 2 is a flow chart depicting the synthesis of POVPC according to the present invention.

Figure 3:
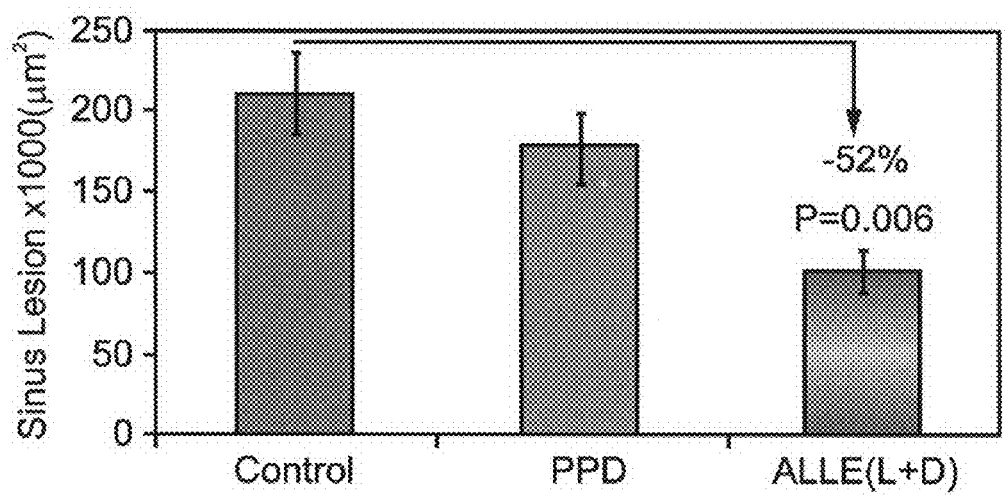

FIG. 3 is a graphic representation demonstrating inhibition of early atherogenesis in apoE-deficient mice by intra peritoneal immunization with mixed D- and L-isomers of ALLE. 5-7 week old Apo-E KO mice were immunized with 150 μg/mouse mixed D- or L-isomers of ALLE coupled to purified tuberculin protein derivative (ALLE L+D) (n=6), purified tuberculin protein derivative alone (PPD) (n=5) or unimmunized (CONTROL) (n=7). Atherogenesis is expressed as the area of atheromatous lesions in the aortic sinus 4.5 weeks following the 4$^{th}$ immunization.

Figure 4:
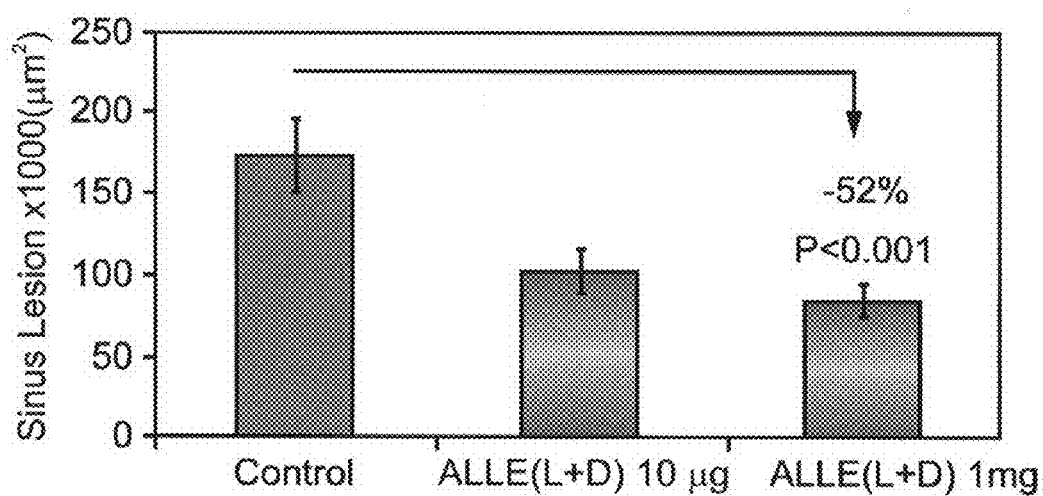

FIG. 4 is a graphic representation demonstrating inhibition of early atherogenesis in Apo-E KO mice by oral administration of ALLE. 6-7.5 week old Apo-E KO mice were fed mixed D- and L-isomers of ALLE: 10 μg/mouse (ALLE L+D 10 μg) (n=11) or 1 mg/mouse (ALLE L+D 1 mg) (n=11); or PBS (CONTROL) (n=12) every other day for 5 days. Atherogenesis is expressed as the area of atheromatous lesions in the aortic sinus 8 weeks after the last feeding.

Figure 5:
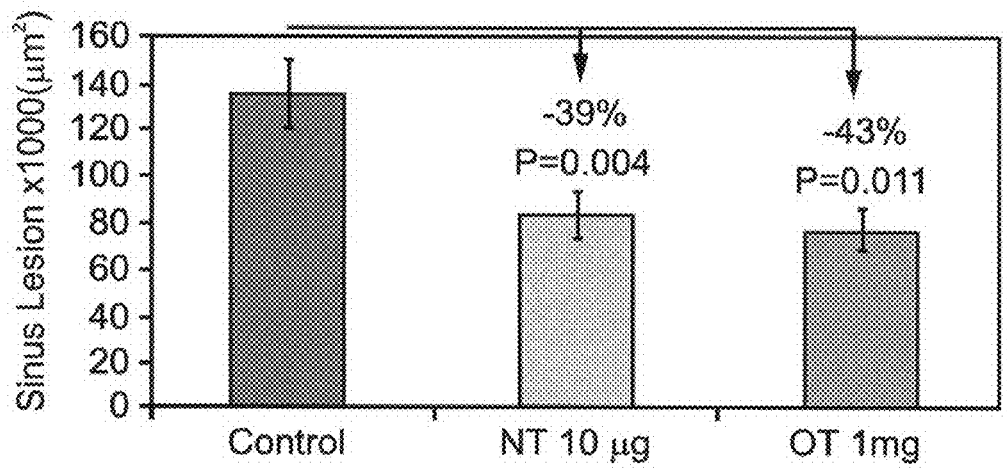

FIG. 5 is a graphic representation demonstrating inhibition of early atherogenesis in Apo-E KO mice by oral and nasal administration of L-ALLE. 7-10 week old Apo-E KO mice were either fed 1 mg/mouse L-ALLE every other day for 5 days (OT L-ALLE) (n=11) or intranasally administered with 10 μg/mouse L-ALLE every other day for 3 days (NT L-ALLE) (n=11). Control mice were fed an identical volume (0.2 ml) of PBS (PBS ORAL) (n=12). Atherogenesis is expressed as the area of atheromatous lesions in the aortic sinus 8 weeks after the last oral or nasal exposure.

Figure 6:
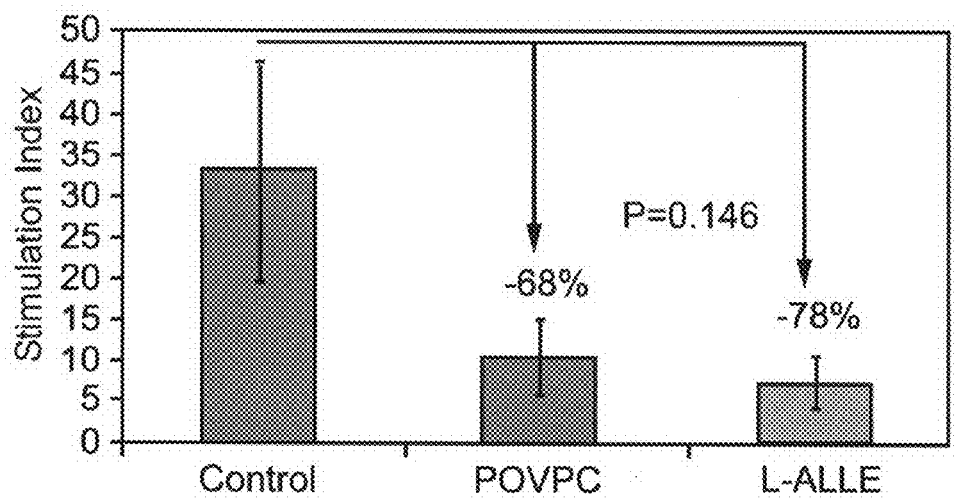

FIG. 6 is a graphic representation demonstrating suppression of immune reactivity to atherosclerotic plaque antigens induced by oral feeding with the synthetic oxidized phospholipids L-ALLE and POVPC. 6 week old male Apo-E KO mice were fed either 1 mg/mouse L-ALLE (L-ALLE) (n=2) or POVPC (POVPC) (n=3) in 0.2 ml PBS; or PBS alone (CONTROL) (n=3) every other day for 5 days. One week following the last feeding the mice were immunized with a single subcutaneous injection of 50 μg Human oxidized LDL antigen. 7 days later T-cells from inguinal lymph node were prepared as described in Materials and Methods section that follows, and exposed to the sensitizing Human ox-LDL antigen for in-vitro assessment of proliferation. Proliferation, indicating immune reactivity, is expressed as the ratio between incorporation of labeled thymidine into the T-cell's DNA in the presence and absence of human ox-LDL antigen (stimulation index, S.I.).

Figure 7:
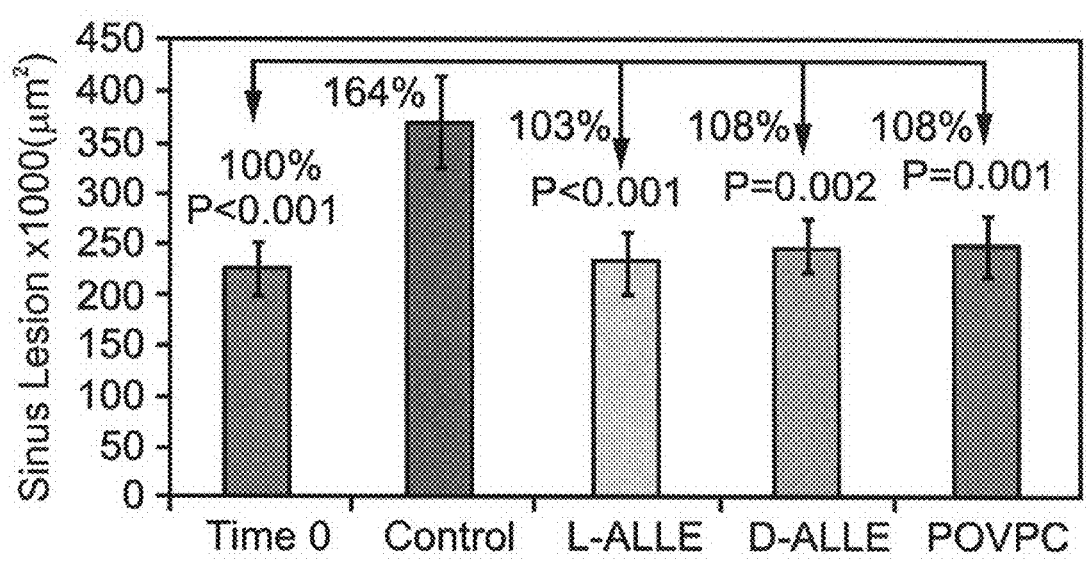

FIG. 7 is a graphic representation demonstrating inhibition of progression of late-stage atherogenesis in Apo-E KO mice by oral administration of the synthetic oxidized phospholipids D-ALLE, L-ALLE or POVPC. 24.5 week old Apo-E KO mice were fed 1 mg/mouse L-ALLE (L-ALLE) (n=11), D-ALLE (D-ALLE) (n=9) or POVPC (POVPC) (n=10) every other day for 5 days, at 4 week intervals over a 12 week period. Control mice were fed an identical volume (0.2 ml) and regimen of PBS (CONTROL) (n=10). Atherogenesis is expressed as the area of atheromatous lesions in the aortic sinus 12 weeks after the first feeding, as compared to the lesion scores of untreated 24.5 week old mice before feeding (sacrificed at Time 0).

Figure 8:
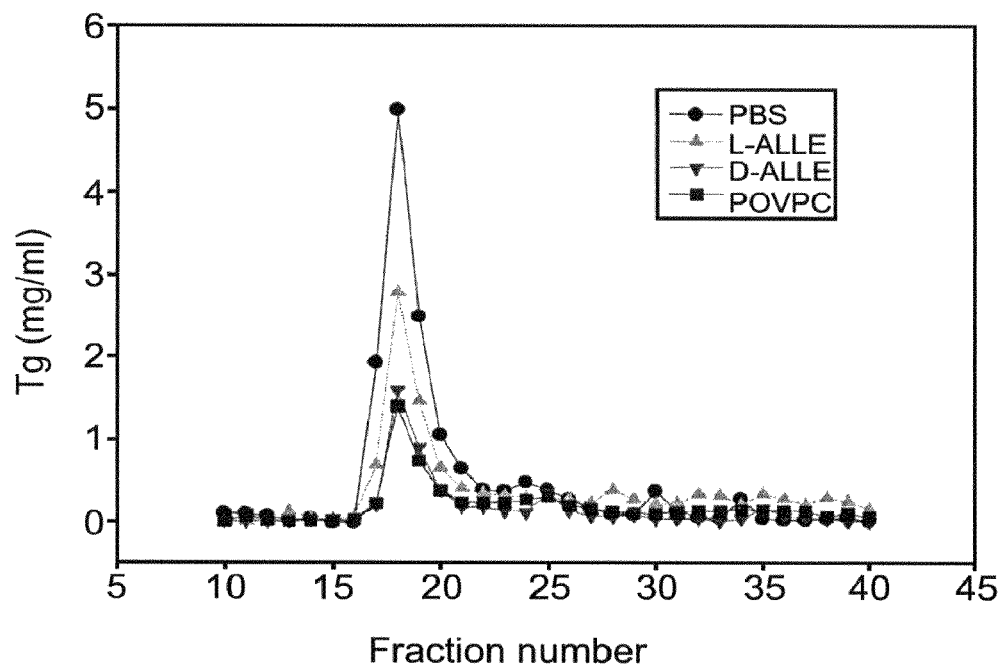

FIG. 8 is a graphic representation demonstrating reduction of triglyceride content of VLDL in Apo-E KO mice induced by feeding synthetic oxidized phospholipids D-ALLE, L-ALLE or POVPC. 24.5 weeks old Apo-E KO mice were fed 1 mg/mouse L-ALLE (triangle) (n=11), D-ALLE (inverted triangle) (n=9) or POVPC (square) (n=10) every other day for 5 days, at 4 weeks intervals over a 12 weeks period. Control mice were fed an identical volume (0.2 ml) and regimen of PBS (circle) (n=10). Triglyceride content (Tg, mg/ml) was measured 9 weeks from t=0, by enzymatic colorimetric method in the VLDL fractions following separation of pooled blood samples on FPLC, as described in the materials and methods section that follows.

Figure 9:
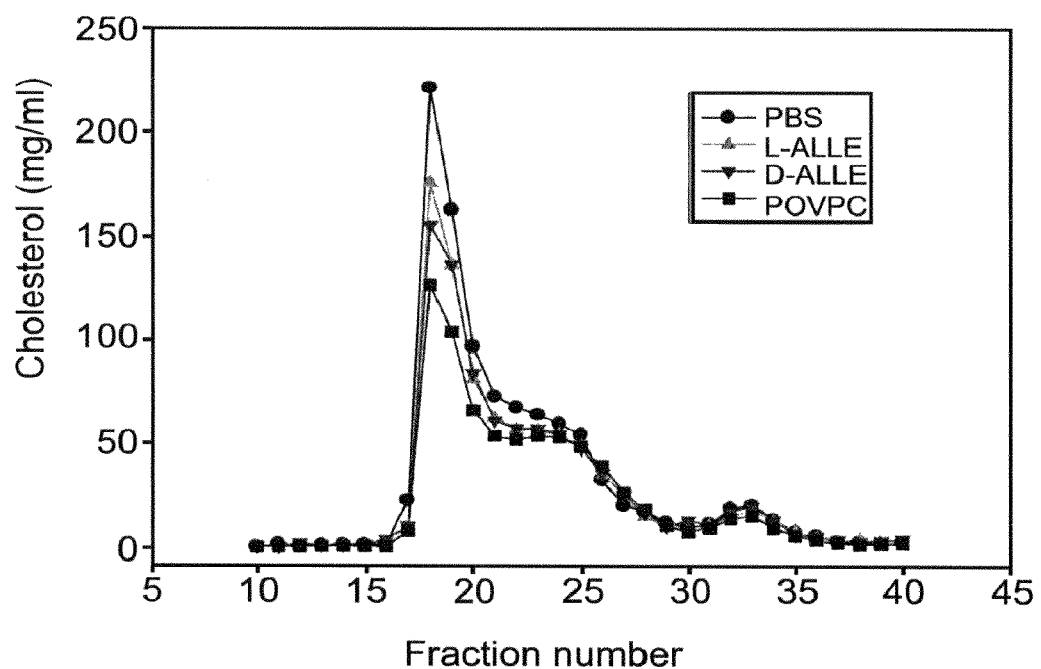

FIG. 9 is a graphic representation demonstrating reduction of cholesterol content of VLDL in Apo-E KO mice induced by feeding synthetic oxidized phospholipids D-ALLE, L-ALLE or POVPC. 24.5 weeks old Apo-E KO mice were fed 1 mg/mouse L-ALLE (triangle) (n=11), D-ALLE (inverted triangle) (n=9) or POVPC (square) (n=10) every other day for 5 days, at 4 weeks intervals over a 12 weeks period. Control mice were fed an identical volume (0.2 ml) and regimen of PBS (circle) (n=10). Cholesterol content (Cholesterol, mg/ml) was measured 9 weeks from t=0, by enzymatic colorimetric method in the VLDL fractions following separation of pooled blood samples on FPLC, as described in the materials and methods section that follows.

FIG. 10 presents 2D structural descriptions of 1-Hexadecyl-2-(5'-Carboxy-butyl)-sn-glycero-3-phosphocholine (CI-201, Compound VII), 1-Hexadecyl-2-(5',5'-Dimethoxy-pentyloxy)-sn-glycero-3-phosphocholine (Compound VIIIa) and 1-Hexadecyl-2-(5',5'-Diethoxy-pentyloxy)-sn-glycero-3-phosphocholine (Compound VIIIb).

Figure 11:
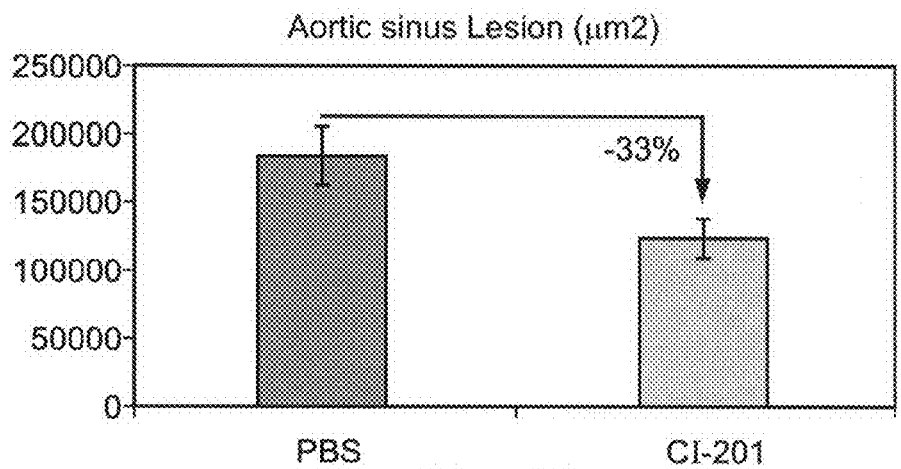

FIG. 11 is a graphic representation demonstrating inhibition of early atherogenesis in Apo-E KO mice by oral administration of CI-201. 12 week old Apo-E KO mice were fed CI-201: 0.025 mg/mouse (n=14); or 0.2 ml PBS (CONTROL) (n=15) every day for 8 weeks (5 times a week). Atherosclerosis is expressed as the area of atheromatous lesion in the aortic sinus 11 weeks after the first feeding.

Figure 12A:
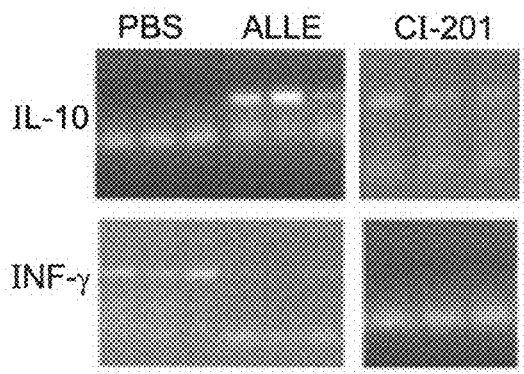
Figure 12C:
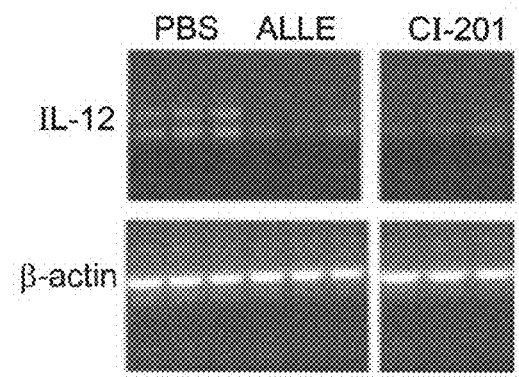
Figure 12B:
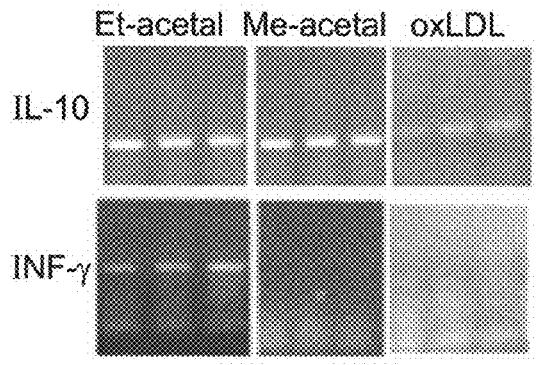
Figure 12D:
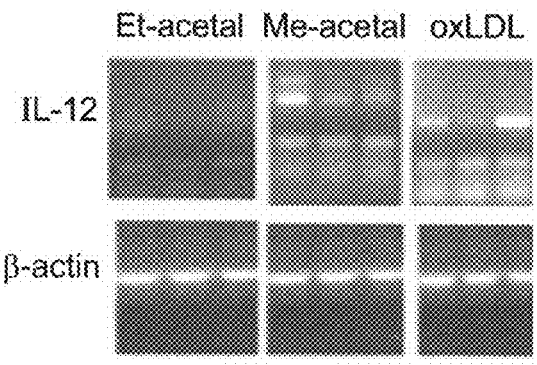

FIGS. 12a-d present photographs demonstrating the cytokine expression levels in the aorta of mice treated with ALLE, CI-201, its ethyl acetal derivative (Et-acetal), its methyl acetal derivative (Me-acetal), oxLDL or PBS. Particularly, FIGS. 12a and 12b present the elevation of IL-10 expression level in the aorta of mice treated with ALLE, CI-201, Et-acetal, Me-acetal and oxLDL as compared with non-treated mice (PBS) and the reduced IFN-gamma expression levels in aortas from mice treated with ALLE, CI-201, Me-acetal and oxLDL as compared with PBS treated mice, and FIGS. 12c and 12d present the reduced IL-12 expression in mice treated with ALLE, CI-201 and Et-acetal as compared with PBS treated group. 10-12 weeks old Apo-E KO mice were fed 1 mg/mouse/0.2 ml of the tested antigen (ALLE, CI-201, Et-acetal, Me-acetal) or 0.1 mg/mouse/0.2 ml oxLDL or administered with 0.2 ml PBS. Oral administrations took place 5 times every other day and the cytokine expression was evaluated 8 weeks after the last oral administration.

Figure 13:
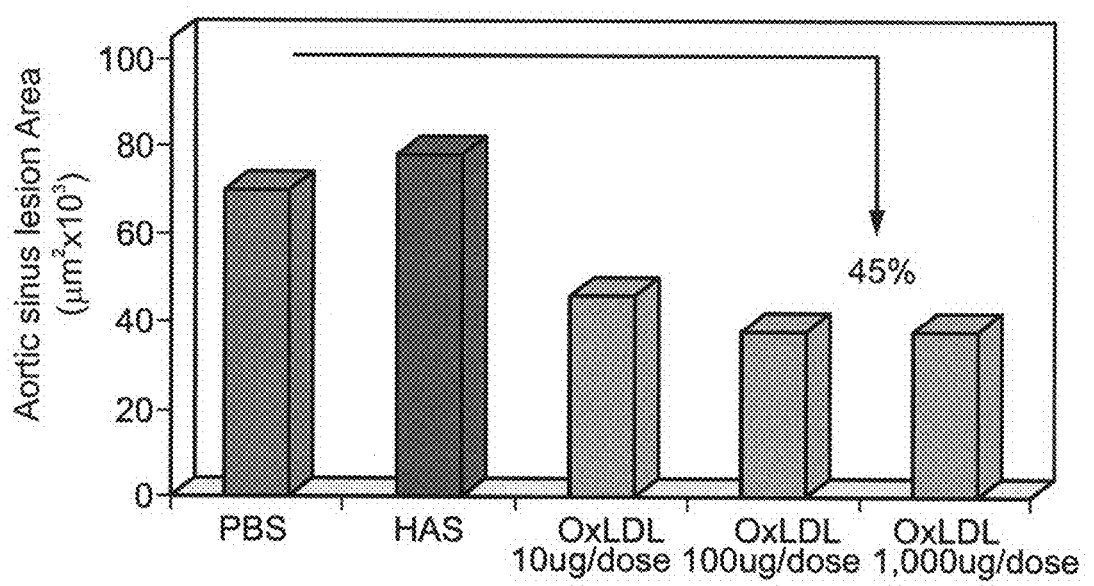

FIG. 13 presents a bar graph demonstrating the attenuation of atherogenesis in LDL-RD mice by oral administration of oxLDL. LDL-RD mice were fed with PBS, or 10, 100 and 1,000 μg/dose oxLDL, 5 times every other day. Atherogenesis is expressed as the area of atheromatous lesions in the aortic sinus, 5 weeks after the last feeding.

Figure 14A:
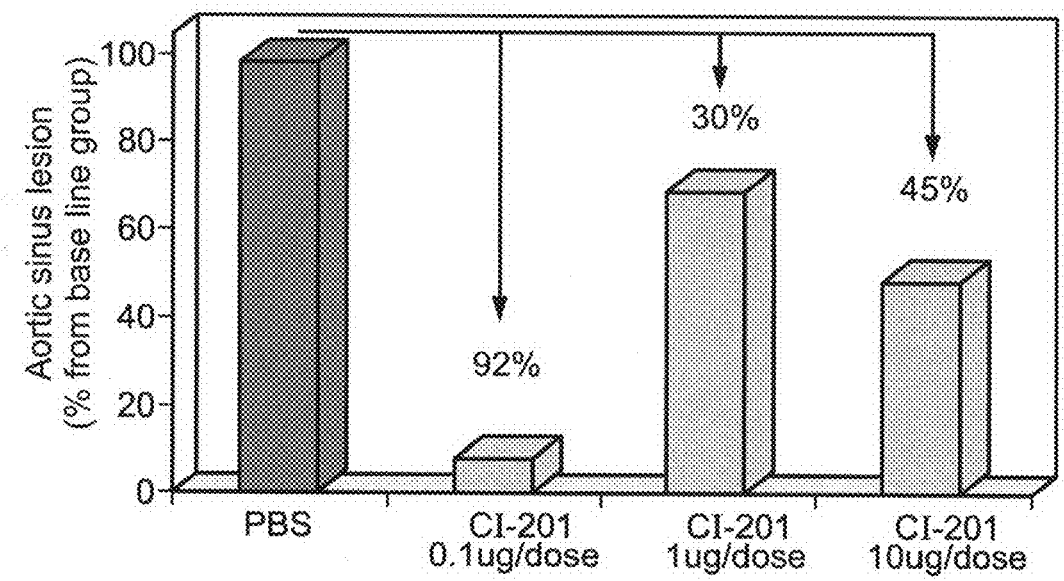

FIGS. 14a-b present bar graphs demonstrating the inhibition of atherogenesis in Apo-E KO mice by oral administration of CI-201. Apo-E KO mice were fed with PBS (control) or 0.1, 1 and 10 μg/dose CI-201, at three sets at the beginning of each month, 5 times every other day in each set. Atherogenesis is expressed as the area of atheromatous lesions in the aortic sinus, 12 weeks after the first feeding. FIG. 14a presents the extent of atherosclerosis in each group. FIG. 14b presents the dramatic effect of the low dose CI-201 treatment on atherosclerosis, as compared with the "base line" group (sacrificed at day 0) and the control group.

FIGS. 15a-b present bar graphs demonstrating the elevation in serum levels of IL-10 (FIG. 15a) and the prevention of SAA elevation (FIG. 15b) in Apo-E KO mice treated by CI-201. Apo-E KO mice were fed with PBS (control) or CI-201, 5 times every other day. Serum was collected at the beginning of the experiment, 2 weeks and 4 weeks after the first feeding. Markers levels were evaluated as described in the Materials and Methods section that follows.

Figure 16A:
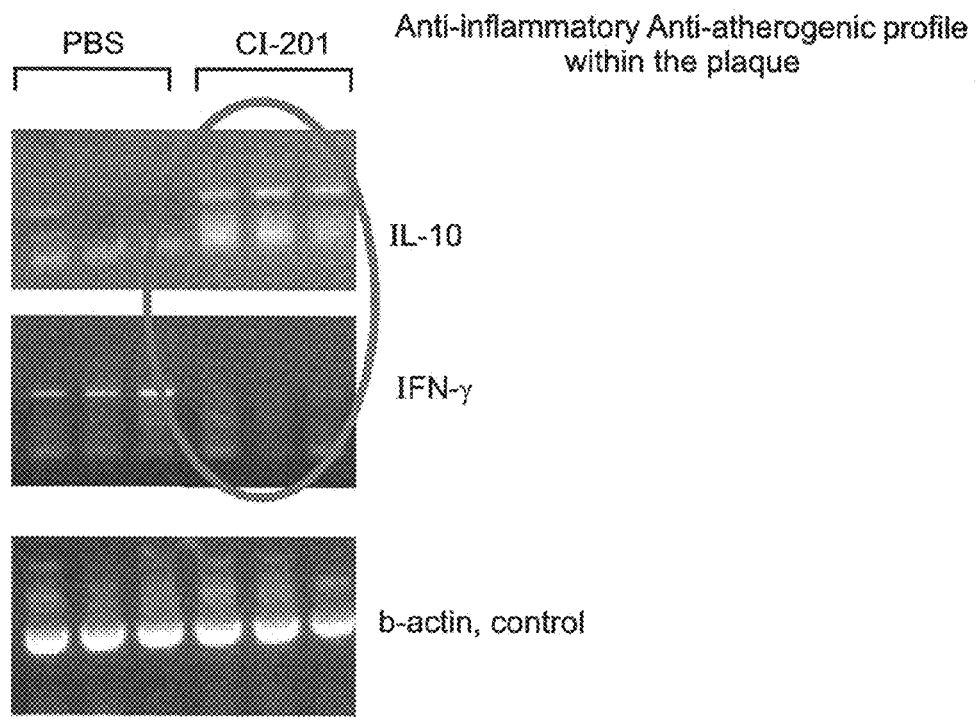
Figure 16B:
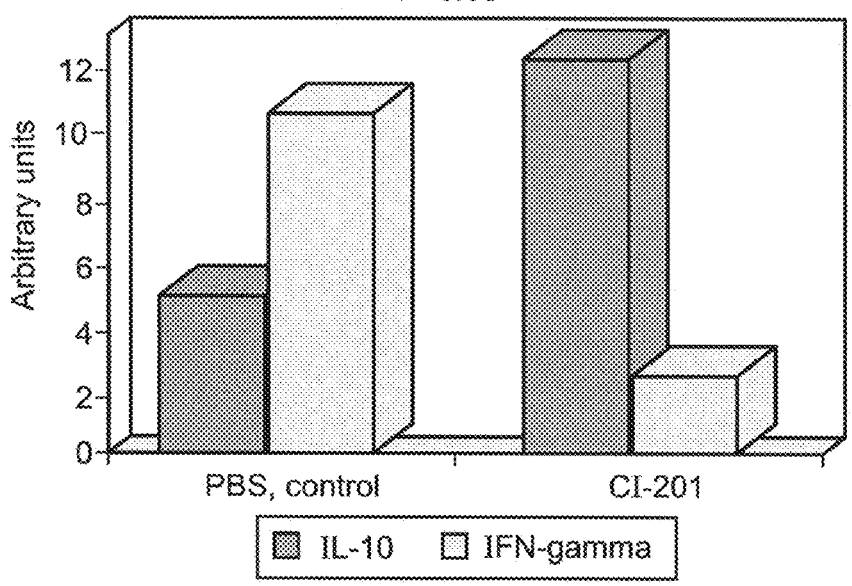

FIGS. 16a-b present photographs (FIG. 16a) and a graphic representation (FIG. 16b) demonstrating the cytokine expression levels in the aorta of mice treated with CI-201 or PBS. Particularly, FIGS. 16a and 16b present the elevation of IL-10 expression level in the aorta of mice treated with CI-201, as compared with non-treated mice (PBS) and the reduced IFN-gamma expression levels in aortas from mice treated with CI-201, as compared with PBS treated mice. Apo-E KO mice were fed with 1 mg/mouse CI-201 or with 0.2 ml/mouse PBS, 5 times every other day. The expression of the anti-inflammatory cytokine IL-10 and the pro-inflammatory cytokine IFN-$\gamma$ were determined 8 weeks after the last feeding.

Figure 17:
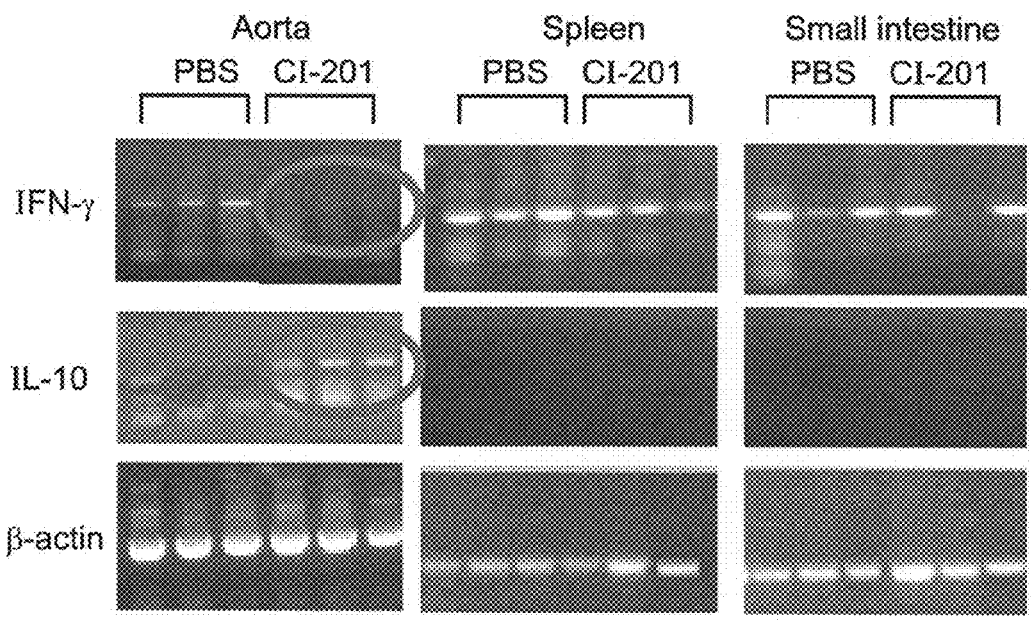

FIG. 17 presents photographs demonstrating aorta-targeted CI-201 oral treatment in Apo-E KO mice. While in the aorta CI-201 treatment induced elevation of IL-10 expression level and reduction of IFN-gamma expression levels, as compared with the PBS treatment, no differences were observed in cytokine expression in the spleen and in the small intestine between the CI-201 treated group and the control, PBS treated, group.

Figure 18:
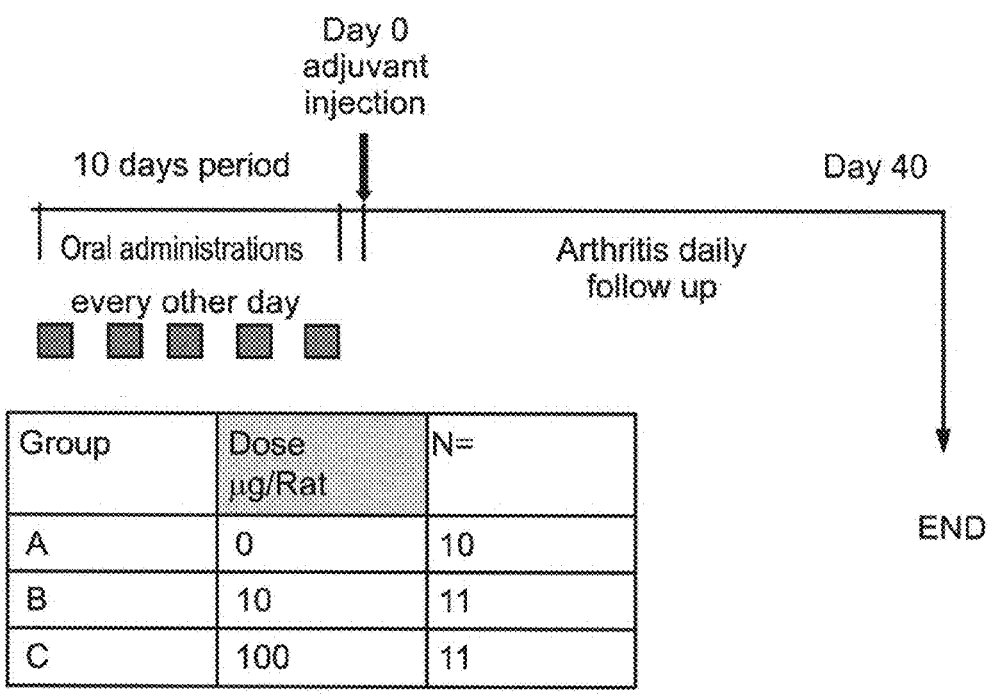

FIG. 18 is a graphic presentation of the study design for evaluating the attenuation of Adjuvant-induced arthritis (AIA) in rats pre-treated with CI-201.

Figure 19:
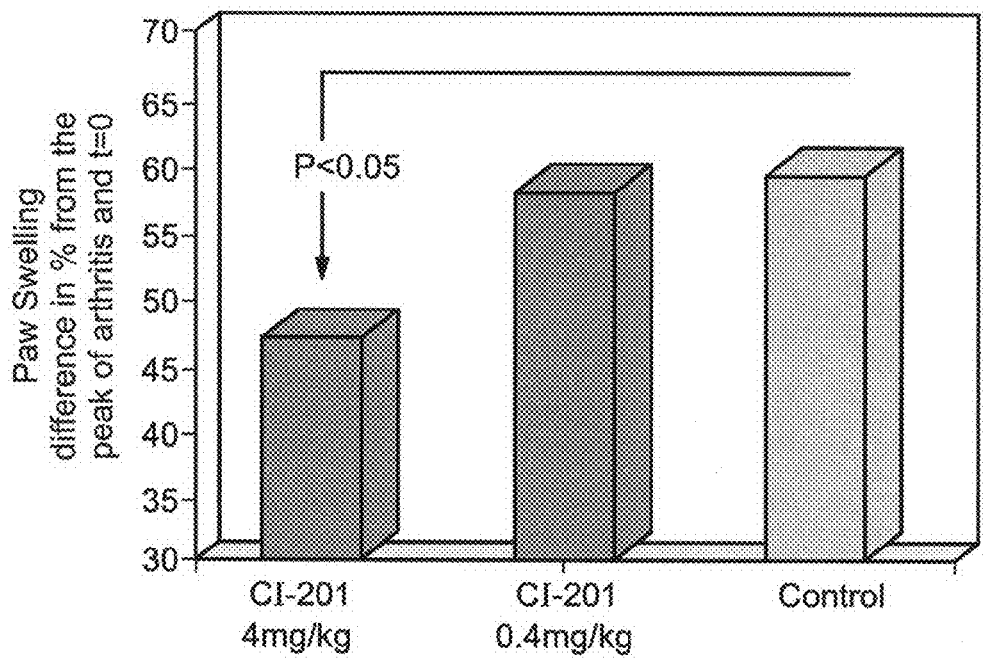

FIG. 19 presents a bar graph demonstrating the effect of oral administration of CI-201 in Adjuvant induced arthritis (AIA)-induced rats in terms of paw swelling. Lewis rats were fed with CI-201 or PBS (CONTROL), 5 times every other day, and where thereafter injected intradermally with a tuberculosis suspension.

Figure 20:
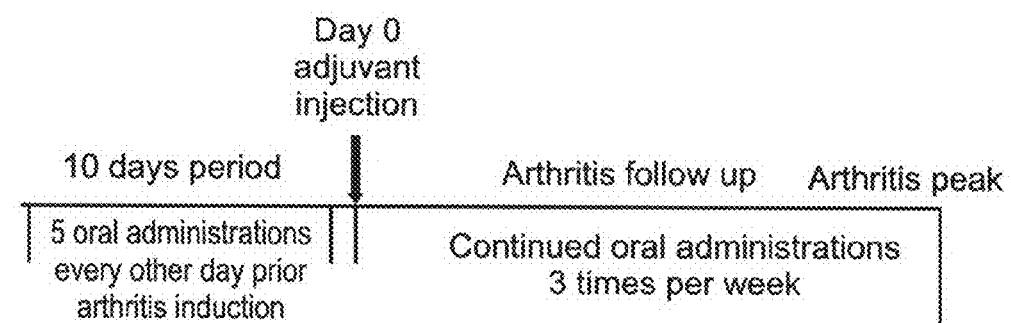

FIG. 20 is a graphic presentation of the study design for evaluating the attenuation of Adjuvant-induced arthritis (AIA) in rats continuously treated with CI-201.

Figure 21:
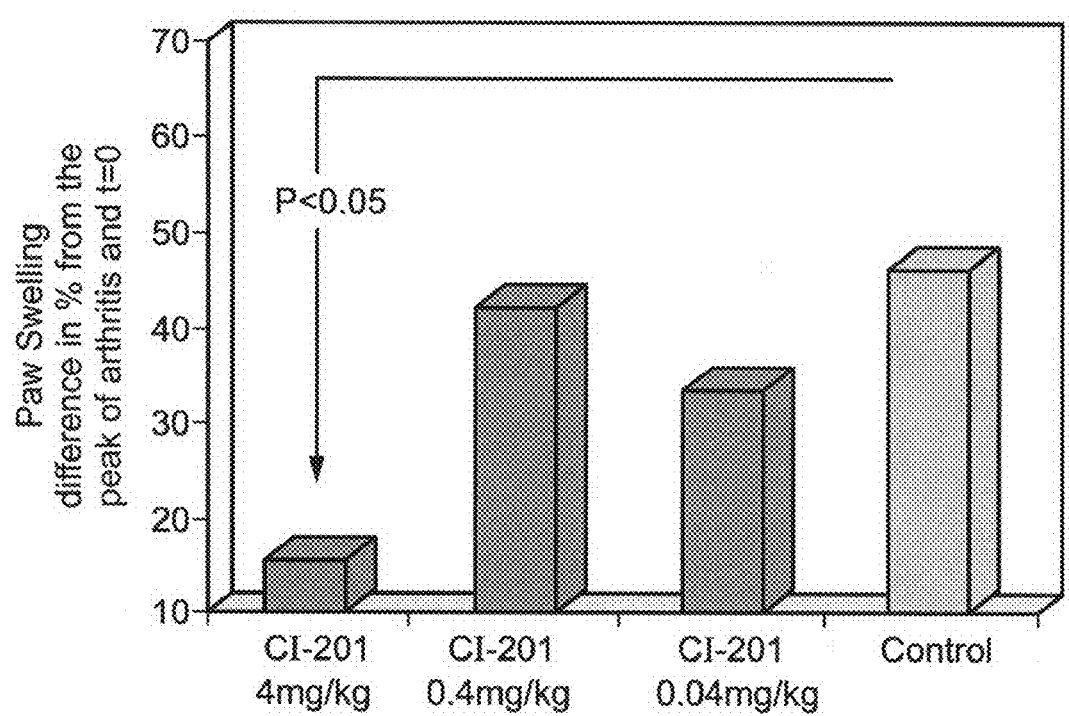

FIG. 21 presents a bar graph demonstrating the effect of oral administration of CI-201 in AIA-induced Lewis rats in terms of paw swelling. Lewis rats were fed with CI-201 or PBS (CONTROL), 5 times every other day, subjected thereafter to arthritis induction and were then continuously treated with CI-201 by feeding 3 times a week.

Figure 22:
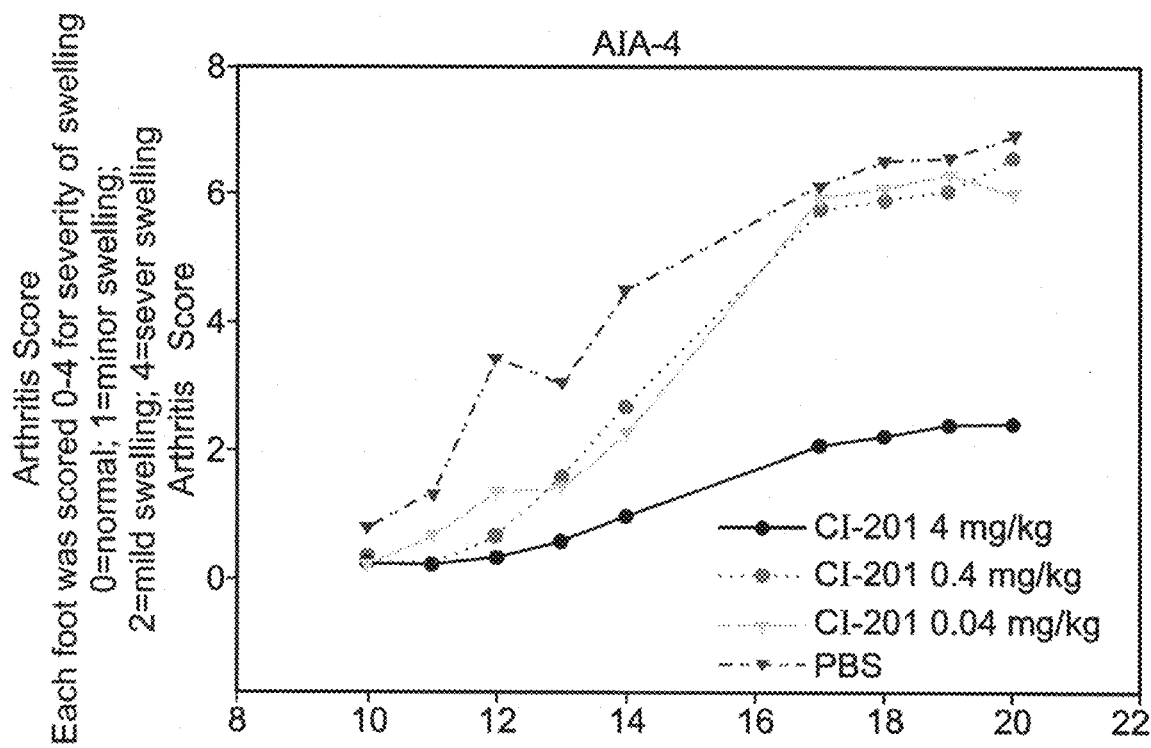

FIG. 22 presents comparative plots demonstrating the arthritis score assessment monitored during arthritis development in rats treated with various concentrations of CI-201, as compared with PBS-treated rats.

Figure 23:
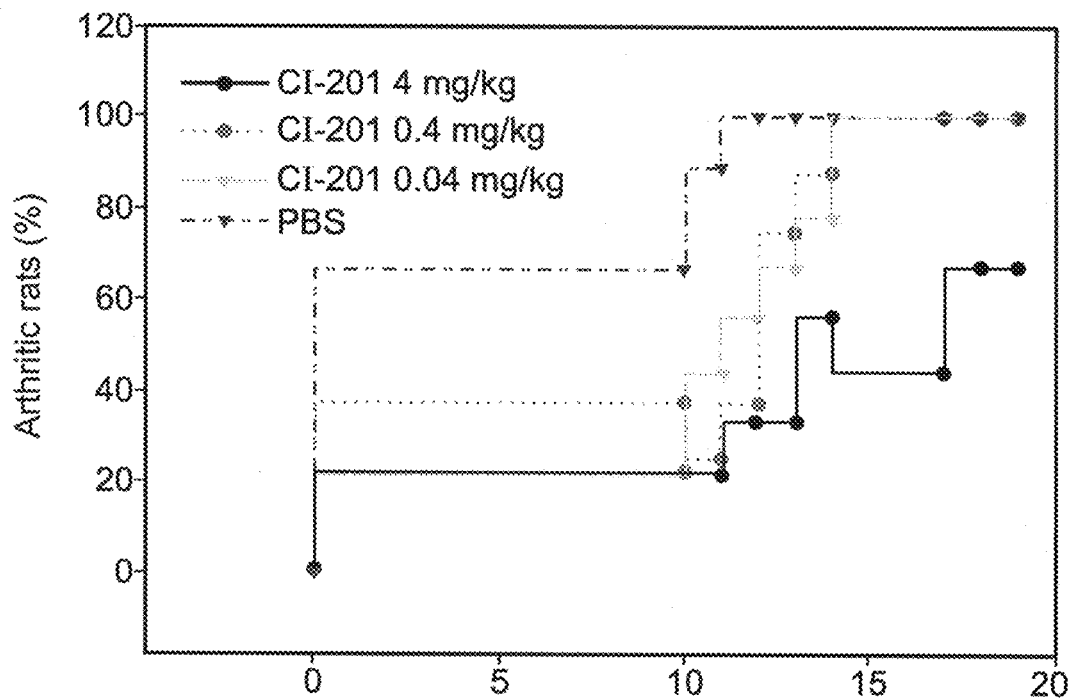

FIG. 23 presents comparative plots demonstrating the percentage of rats having arthritis symptoms following treatment with PBS (control) and various concentrations of CI-201.

Figure 24:
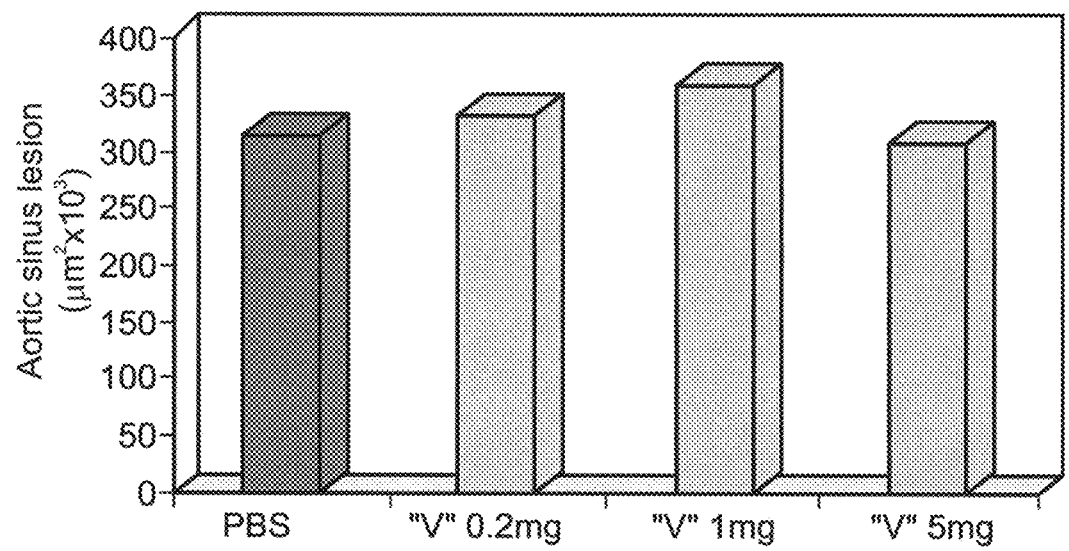

FIG. 24 presents a bar graph demonstrating the effect on early atherogenesis in Apo-E KO mice induced by oral administration of the pre-oxidized Compound V. 8-10 week old female Apo-E KO mice were fed with Compound V: 5 mg/mouse (n=6), 1 mg/mouse (n=6), 0.2 mg/mouse (n=6) or PBS (control) (n=7) every other day for 5 days. Atherogenesis is expressed as the area of atheromatous lesions in the aortic sinus 8 weeks after the last feeding.

Figure 25:
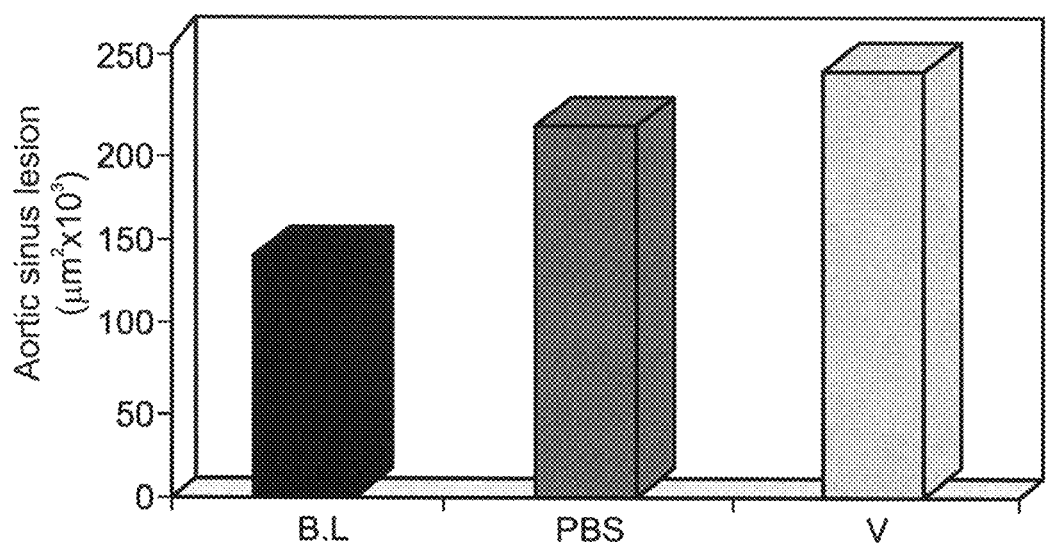

FIG. 25 presents bar graphs demonstrating the effect on atherogenesis in Apo-E KO mice induced by oral administration of the pre-oxidized Compound V. 23-26 week old Apo-E KO mice were either sacrificed at the beginning of experiment (baseline B. L. group, n=10) or fed with PBS (control, n=11) or 0.1 $\mu$g/dose Compound V (n=10), at three sets at the beginning of each month, 5 times every other day in each set. Atherogenesis is expressed as the area of atheromatous lesions in the aortic sinus, 12 weeks after the first feeding.

Figure 26B:
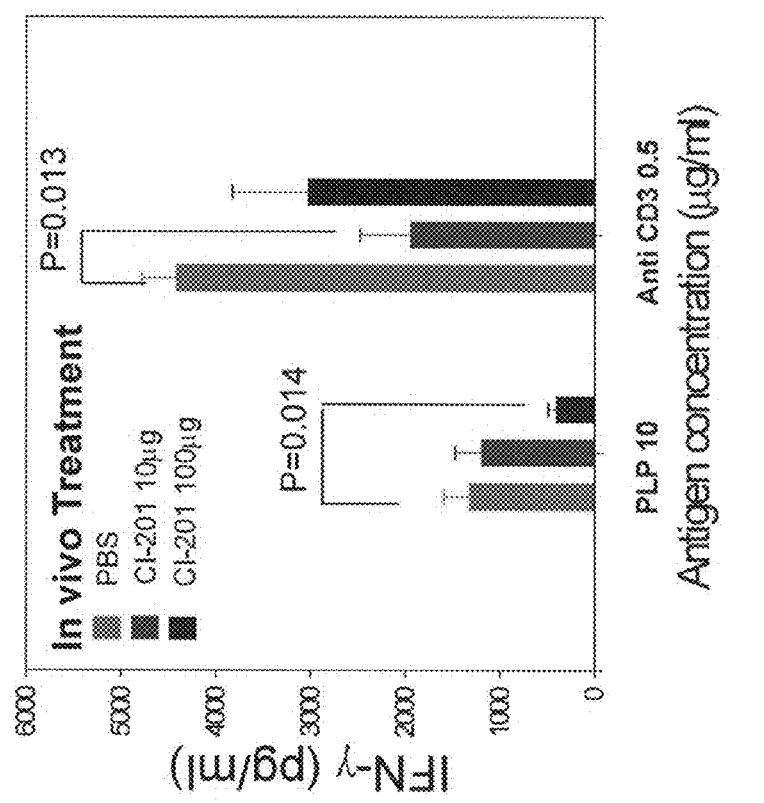
Figure 26A:
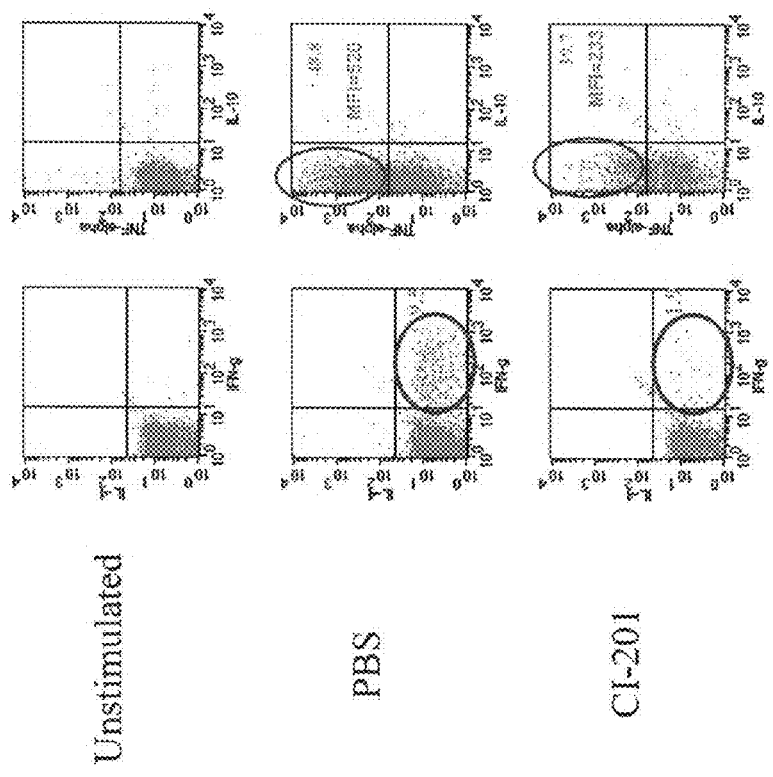

FIGS. 26a-b are scatter plots and graphs illustrating that in vivo administration of CI-201 reduces IFN-$\gamma$ production by T cells. (FIG. 26a) C57BL/6 mice were fed in alternate days from day −10 to day +10 with CI-201 (0.1 $\mu$g/feed) of PBS. On day 0, mice were immunized with ovalbumin in CFA. On day 10, draining lymph nodes were excised and cells stimulated with ovalbumin. Cells were expanded for a week and then re-stimulated for 4 hours with plate bound anti-CD3 and anti-CD28 (5 $\mu$g/ml) in the presence of monensin (2 $\mu$M) and tested for cytokine expression by intracellular staining. Results are gated on CD4+ T cells. (FIG. 26b) SJL mice were orally administered with CI-201 (10 and 100 $\mu$g/mouse/feed) or PBS, 5 times once a day, every other day for a total of 5 doses and then immunized with PLP peptide 139-151 in CFA followed by 4 more administrations every other day. Lymph nodes were collected 10 days later, stimulated ex vivo with 10 $\mu$g/ml of PLP 139-151 peptide or 0.5 $\mu$g/ml of anti CD3 and three days later supernatants were collected and tested by ELISA for cytokine production.

Figure 27:
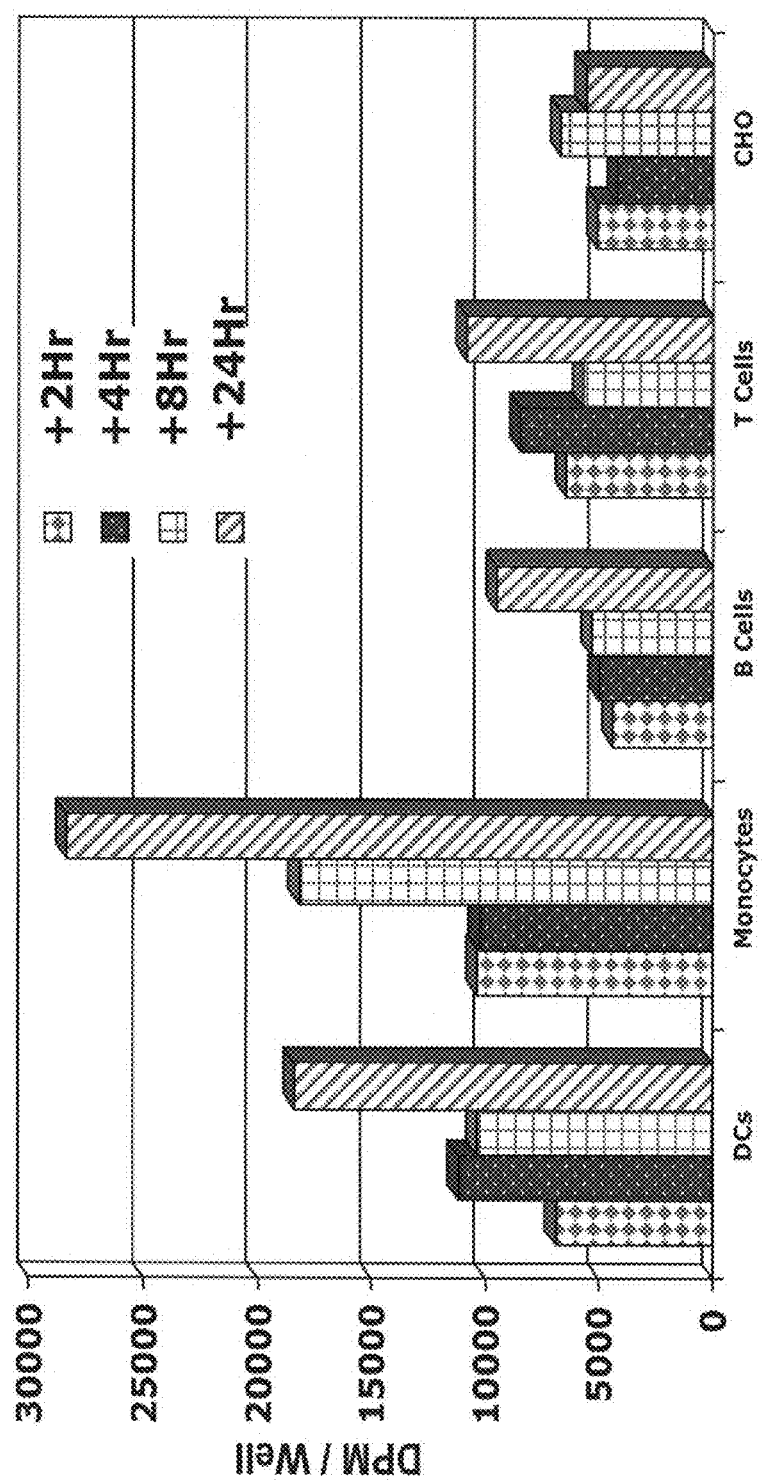

FIG. 27 is a bar graph illustrating the preferential binding of $^3$H—CI-201 to professional antigen presenting cells. $^3$H—CI-201 uptake was evaluated at the indicated time points in monocytes, dendritic, T and B cell lines. Chinese hamster ovary cells (CHO) served as a control cell line.

Figure 28A:
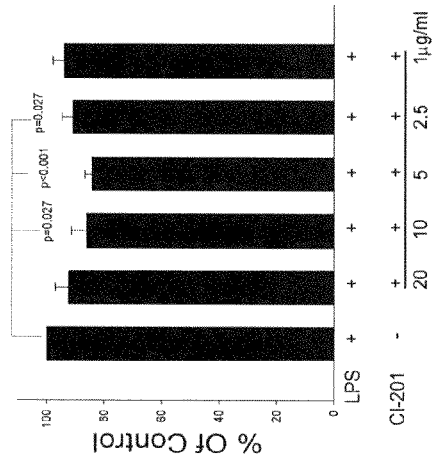
Figure 28B:
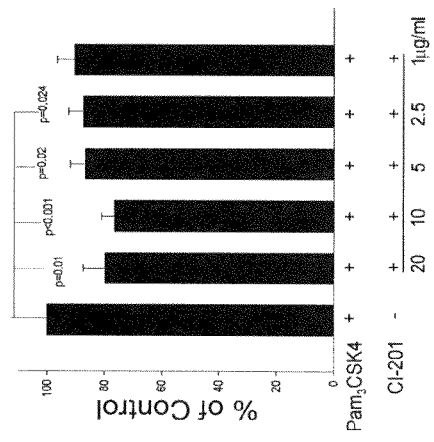
Figure 28D:
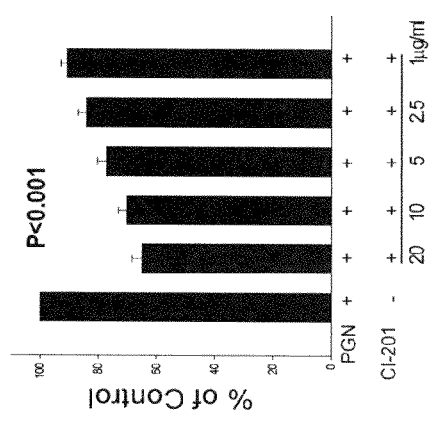
Figure 28C:
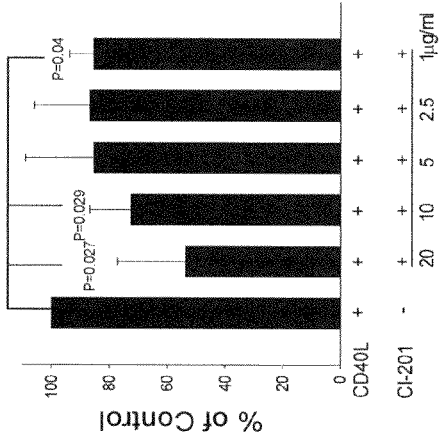
Figure 28E:
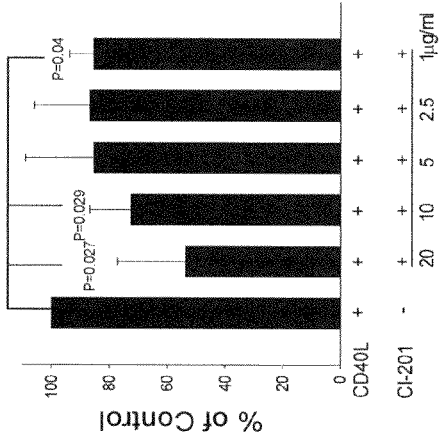
Figure 28F:
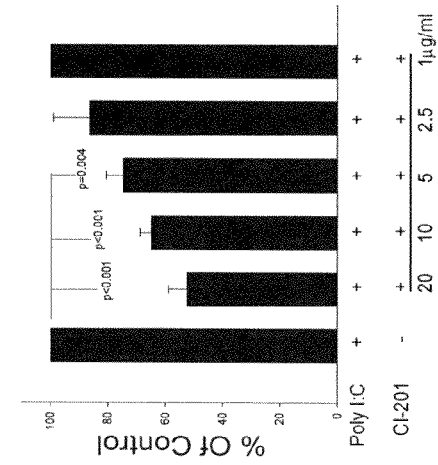
Figure 28N:
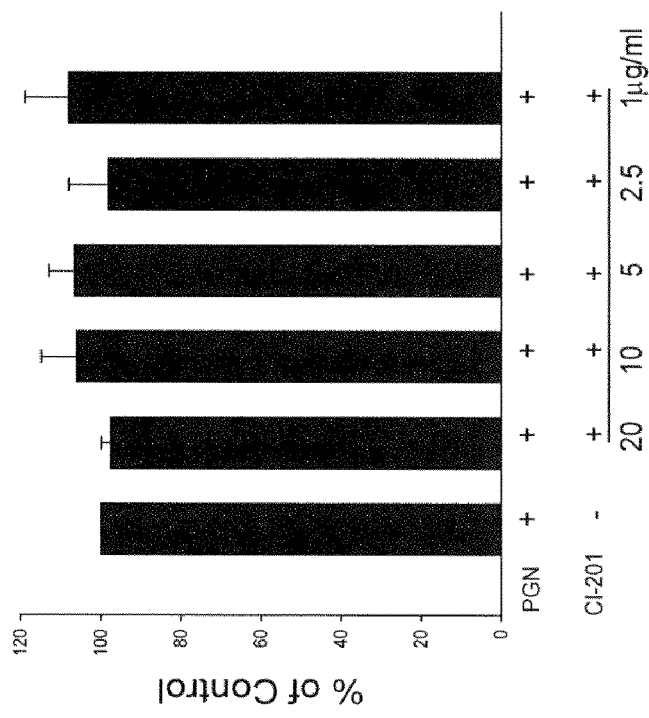
Figure 28M:
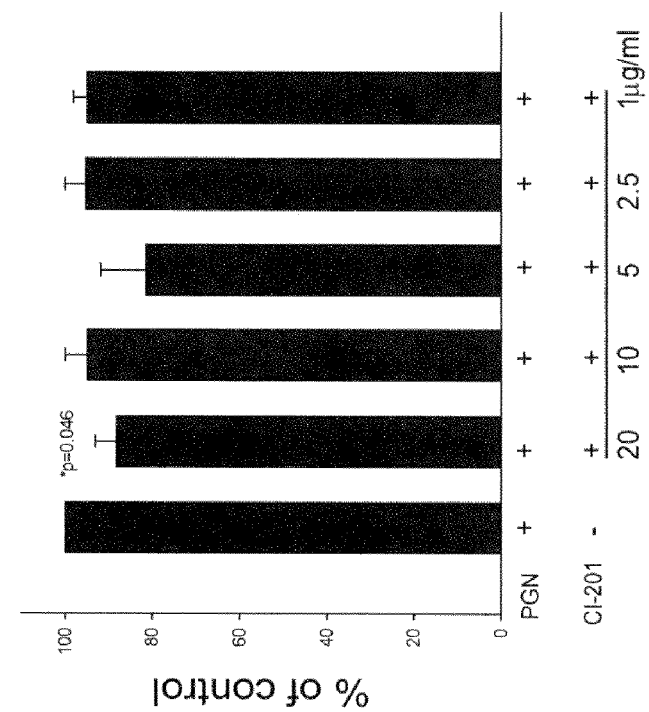

FIGS. 28a-n are bar graphs illustrating that CI-201 inhibits p40 but not the production of other pro inflammatory cytokines by activated BMDC's. BMDC's were incubated for 1 hour with various CI-201 concentrations prior to activation with the indicated agonists at the concentrations listed in the materials and methods. Supernatant were collected 24 hours following activation and the levels of p40 (FIGS. 28a-f) and TNF-$\alpha$ (FIGS. 28g-l) were measured by ELISA.

BMDC's were incubated for 1 hour with different CI-201 concentrations prior to activation with 10 $\mu$g/ml of PGN. Supernatant were collected 24 hours following activation and the levels of IL-6 (FIG. 3M) and IL-1 (FIG. 3N) were measured.

FIGS. 29a-d are bar graphs illustrating that CI-201 alters p40 and p19 a RNA expression level. Purified BM CD11c+ DC's were incubated for 1 hour with CI-201 (20 $\mu$g/ml) prior to activation with PGN (10 $\mu$g/ml) and RNA was isolated at the indicated time points. Q-PCR was performed for IL-12/IL-23p40 (FIG. 29a), IL-12p35 (FIG. 29b), IL-23p19 (FIG. 29c) and IL-27p28 (FIG. 29d) All results were normalized to GAPDH.

Figure 30B:
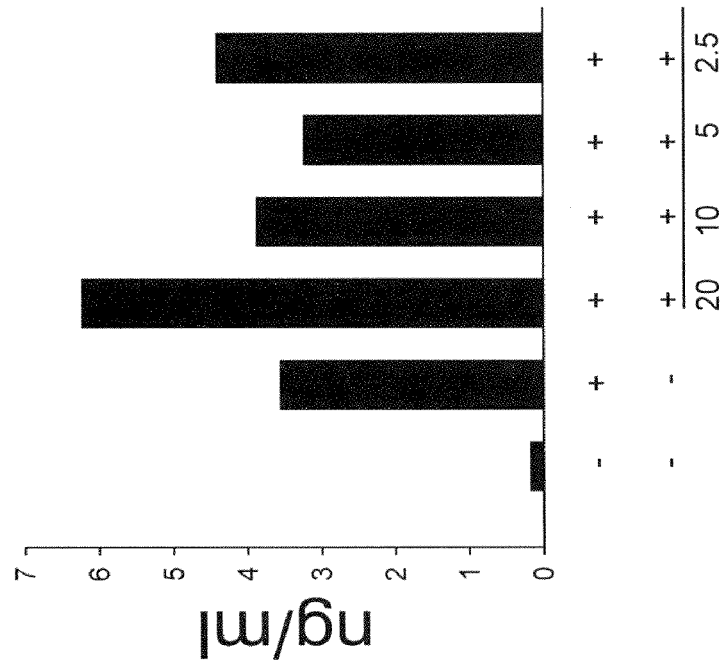
Figure 30A:
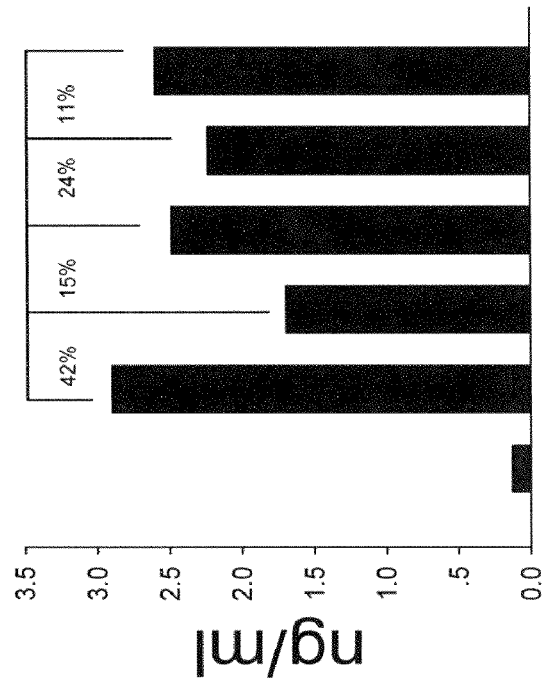

FIGS. 30a-b are bar graphs illustrating that CI-201 inhibits p40 but not TNF-$\alpha$ production by human DC's. Mo-Dc's were incubated for 1 hour with various CI-201 concentrations prior to activation with 10 $\mu$g/ml of PGN. Supernatants were collected 24 hours following activation and the levels of p40 (FIG. 30a) and TNF-$\alpha$ (FIG. 30b) were measured by ELISA.

FIGS. 31a-d are bar graphs illustrating that CI-201 effects p40 and TNF-$\alpha$ production by PBMC's. PBMC's were isolated from two separate donors and incubated for 1 hour with various CI-201 concentrations prior to activation with 10 $\mu$g/ml of PGN. Supernatant were collected 24 hours following activation and the levels of p40 (FIGS. 31a-b) and TNF-$\alpha$ (FIG. 31c-d) were measured by ELISA.

FIGS. 32a-b are bar graphs illustrating that CI-201 does not impair p40 production by Monocytes/Macrophages. Purified splenic CD11b monocytes and macrophages were resistant to incubated for 1 hour with various CI-201 concentrations prior to activation with 10 µg/ml of PGN. Supernatants were collected 24 hours following activation and the levels of p40 (FIG. 32a) and TNF-α (FIG. 32b) were measured by ELISA.

Figure 33G:
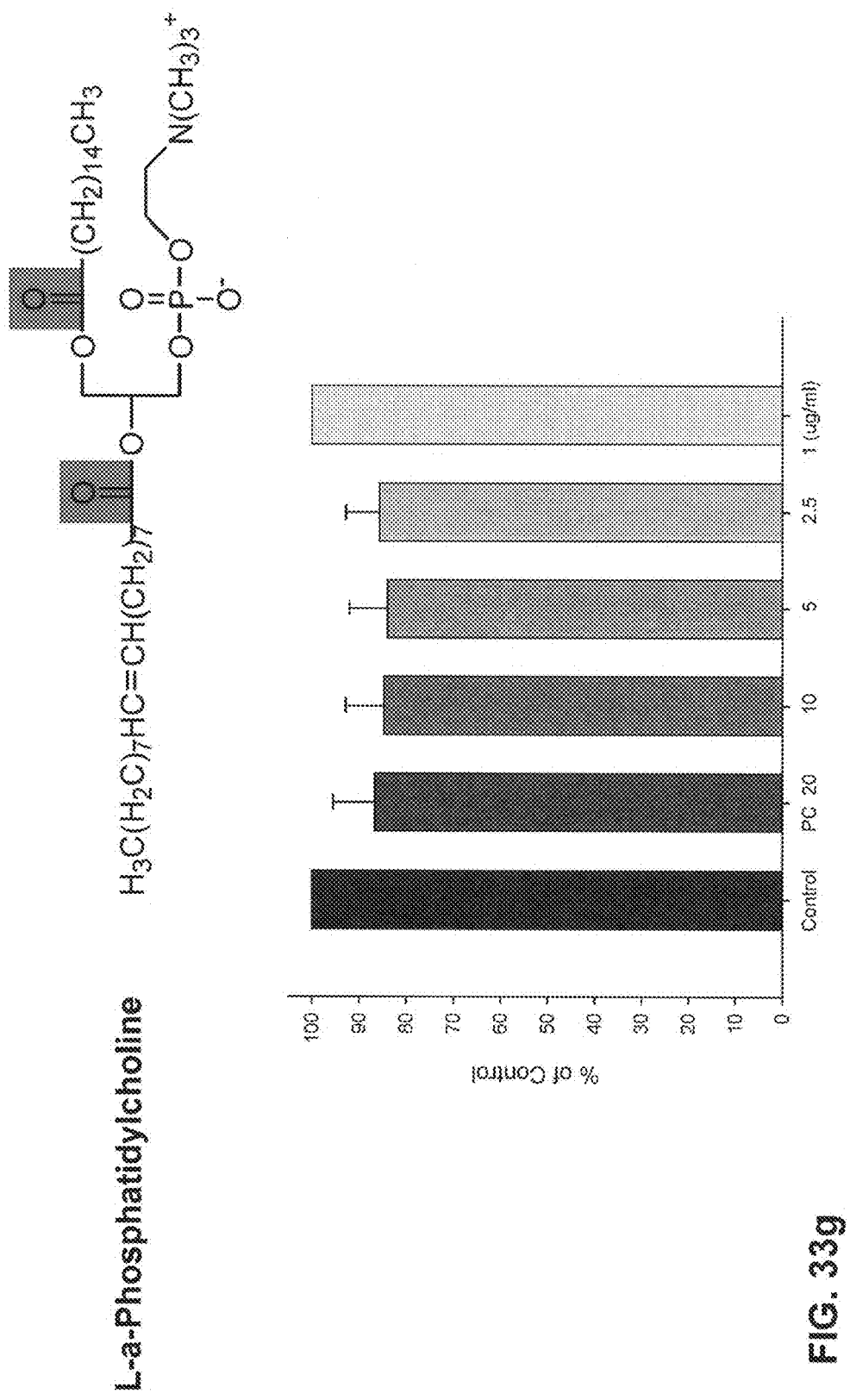

FIGS. 33a-m are structure-function analysis with CI-201 derivatives. BMDC's were incubated for 1 h with various CI-201 concentrations (FIG. 33a) and either newly synthesized or commercially available CI-201 analogous (FIGS. 33b-m) prior to activation with 10 µg/ml of PGN. Supernatant were collected 24 hours following activation and the levels of p40 was measured by ELISA.

DESCRIPTION OF THE PREFERRED EMBODIMENTS

The present invention is of methods and compositions employing oxidized lipids, which can be utilized in treating or preventing an inflammation associated with endogenous oxidized lipids. Particularly, the present invention is of (i) novel oxidized lipids; (ii) pharmaceutical compositions containing same; (iii) methods employing the novel oxidized lipids, as well as other oxidized lipids, for treating or preventing an inflammation associated with endogenous oxidized lipids, and thereby treating or preventing inflammation-associated diseases and disorders such as, but not limited to, atherosclerosis, cardiovascular diseases, cerebrovascular diseases, peripheral vascular diseases, stenosis, restenosis, in-stent-stenosis, autoimmune diseases or disorders, inflammatory diseases or disorders, infectious diseases or disorders and proliferative disease or disorders.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Experimental and clinical evidence indicates a causative role for oxidized LDL (ox LDL) and LDL components in the etiology of an excessive inflammatory response in atherosclerosis. Both cellular and humoral immune reactivity to plaque related oxidized LDL have been demonstrated, suggesting an important anti-oxidized LDL autoimmune component in atherogenesis. Thus, LDL, oxidized LDL and components thereof, have been the targets of numerous therapies for prevention and treatment of heart disease, cerebral-vascular disease and peripheral vascular disease.

Prior art studies associated with the role of oxidized LDL and components thereof in reducing the immune response to endogenous (e.g., plaque related) oxidized LDL employed either a crude antigen preparation consisting of centrifuged, filtered and purified human serum LDL which had been subjected to a lengthy oxidation process with $Cu^{++}$ or MDA, or synthetically prepared oxidized LDL analogs. Since phospholipids are considered as active LDL components, studies with synthetically prepared oxidized LDL analogs typically involved oxidized phospholipids (e.g., POVPC and PGPC).

Although the prior art teaches that oral administration of oxidized LDL can result in 30% reduction in atherogenesis, thus suggesting a protective effect of oxidized LDL, presumably via oral tolerance, no identification of specific lipid antigens or immunogenic LDL components was made.

Another obstacle encountered by these prior art studies was the inherent instability of the crude oxidized LDL in vivo, due to enzymatic activity and uptake of oxidized LDL by the liver and cellular immune mechanisms. Such an inherent instability is also associated with in vivo applications that utilize synthetic oxidized LDL derivatives such as POVPC and PGPC (described hereinabove).

Hence, hitherto, no direct correlation between exogenous oxidized LDL or components thereof and endogenous oxidized LDL, in terms of immunomodulation, has been established. Oxidized LDL analogs, devoid of the inherent instability and other limitations involved with the administration of oxidized LDL, which can modulate the immune and/or inflammatory response associated with endogenous oxidized LDL and other endogenous oxidized lipids, have not been uncovered so far as well.

While conceiving the present invention, it was hypothesized that synthetically defined oxidized lipids in general and oxidized LDL analogs in particular could modulate the immune reactivity to endogenous oxidized lipids in general and oxidized LDL in particular and thus be used in the treatment or prevention of a myriad of diseases and disorders, associated with inflammation and/or altered immune response, such as, for example, atherosclerosis and related diseases or disorders, as well as other diseases and disorder associated with endogenous oxidized lipid.

Inflammation involved in atherogenesis often leads to complications such as plaque rupture and thrombosis (Libby et al., Inflammation and atherosclerosis. Circulation. 2002; 105:1135-1143).

The presence of activated T lymphocytes in human atherosclerotic lesion may imply their involvement in the disease initiation and progression (Ross R. Atherosclerosis—an inflammatory disease. NEJM. 1999; 340:115-126). The major class of T lymphocytes, CD4+, can differentiate into the lineages Th1 or Th2, which are functionally defined by the produced cytokine: interferon (IFN)-γ, secreted from the Th1 cells, and interleukin (IL)-4 secreted from the Th2 cells. Among the principle inducers of the Th1 and Th2 cells are IL-12 and IL-10, respectively (Daugherty A and Rateri DL, T lymphocytes in atherosclerosis the Yin-Yang of Th1 and Th2 Influence on lesion formation, Circ Res. 2002; 90:1039-1040; Hansson G K, Vaccination against atherosclerosis science or fiction. Circulation. 2002; 106:1599-1601).

T-lymphocytes isolated from whole blood in patients with acute coronary syndromes or harvested from human carotid plaques have been shown to specifically recognize Ox LDL and proliferate when exposed to Ox LDL (Hansson GK. Immune mechanisms in atherosclerosis. Arterioscler Thromb Vasc Biol 2001; 21:1,876-90). Ox LDL and oxidized lipid byproducts thereof (e.g., oxidized phospholipids) are present within atherosclerotic plaques (Witztum 2001, supra).

Hence, while oxidative modification of LDL can be a prerequisite for rapid accumulation of LDL in macrophages and foam cell formation, it can further induce immunogenic epitopes in the LDL molecule, which lead to formation of antibodies against Ox LDL.

Oxidized LDL epitopes therefore serve as important ligands, mediating the binding and clearance of oxidatively damaged lipoprotein particles and apoptotic cells, and inducing an innate immune response which effects their removal. On the other hand the oxidized LDL epitopes can play a role in the immune activation that characterizes the progressive atherosclerotic plaque.

In view of the above, the present inventors postulated that compounds which can serve as oxidized LDL epitopes may modulate the immune response, so as to induce a beneficial rather than deleterious effect on atherogenesis. In other words, it was postulated that administering, preferably orally, oxidized LDL analogs, such as oxidized phospholipids, would induce tolerance to the endogenous oxidized LDL formed during atherogenesis and would thus reduce the inflammatory response thereto and attenuate atherogenesis progression.

Evidence supporting immunomodulation as a new therapeutic approach to treat atherosclerosis has recently been published (Nicoletti et al. Induction of neonatal tolerance to oxidized lipoprotein reduces atherosclerosis in Apo E knockout (Apo-E KO) mice. Mol. Med. 2000; 6(4):283-290). It was shown that intraperitoneal injection of oxidized LDL to (Apo-E KO) mice at birth induced T-cell tolerance due to clonal deletion, reduced the immune response to oxidized LDL and, as a result, reduced susceptibility to atherosclerosis.

Adaptive and innate immunity have been implicated in the pathogenesis of atherosclerosis as well as in many other disease and disorders. Given their abundance in the lesion, lipids are possible targets of the atherosclerosis-associated immune response. Recently it has been shown that natural killer T (NKT) cells can recognize lipid antigens presented by CD1 molecules. CD1 molecules present lipid antigens to T-cells, unlike the evolutionarily-related major histocompatibility complex (MHC) class I and II molecules, which display peptide antigens. Like MHC class II molecules, however, CD1 molecules consist of a heavy chain associated with the $\beta_2$-microglobulin ($\beta_2$M) light chain. Crystal structures of two CD1 isoforms, human CD1b and mouse CD1d, show an overall domain organization that resembles MHC class I molecules. Notably, the antigen-binding site in CD1 is hydrophobic, forming channels (CD1b) or pockets (mouse CD1d) that can accommodate hydrocarbon chains of lipids. A narrow opening between the $\alpha$-helices permits the display of polar moieties of the lipid in a region accessible for recognition by T-cell receptors (TCRs). This system facilitates the binding of different lipid molecules linked to diverse polar head groups, thereby creating an enormous pool of potential CD1-presented antigens (Zeng et al. Crystal structure of mouse CD1: an MHC-like fold with a large hydrophobic binding groove. Science 1997; 277:339-345).

CD1 molecules bind foreign lipid antigens as they survey the endosomal compartments of infected antigen-presenting cells. Unlike T-cells that recognize CD1-restricted foreign lipids, CD1-restricted T cells that are self-antigen reactive, function as 'auto-effectors' that are rapidly stimulated to carry out helper and effector functions upon interaction with CD1-expressing antigen-presenting cells. The functional distinctions between subsets of CD 1-restricted T-cells and the pathways by which these cells both influence the inflammatory and tolerogenic effects of dendritic cells and activate natural killer cells and other lymphocytes provide insight into how CD1-restricted T cells regulate antimicrobial responses, antitumor immunity and the balance between tolerance and autoimmunity (Vincent et al. Understanding the function of CD1-restricted T cells. Nat. Immunol. 2003; 4:517-23).

Tupin et al. (CD1d-dependent Activation of NKT Cells Aggravates Atherosclerosis. J Exp Med. 2004; 199:417-22) have explored the role of CD1d-restricted NKT cells in atherosclerosis by using apolipoprotein E-deficient (apoE(−/−)) mice, and ApoE(−/−) mice crossed with CD1d(−/−) (CD1d (−/−)apoE(−/−)) mice that exhibited a 25% decrease in lesion size compared with apoE(−/−) mice. Administration of alpha-galactosylceramide, a synthetic glycolipid that activates NKT cells via CD1d, induced a 50% increase in lesion size in apoE(−/−) mice, whereas it did not affect lesion size in apoE (−/−)CD1d(−/−) mice. These results show that activation of CD1d-restricted NKT cells exacerbates atherosclerosis. Zhou et al. (Editing of CD1d-bound lipid antigens by endosomal lipid transfer proteins. Science. 2004; 303:523-7) have reported that mice deficient in prosaposin, the precursor to a family of endosomal lipid transfer proteins (LTP), exhibit specific defects in CD1d-mediated antigen presentation and lack V$\alpha$14 NKT cells. In vitro, saposins extracted monomeric lipids from membranes and from CD1, thereby promoting the loading as well as the editing of lipids on CD1. Transient complexes between CD1, lipid, and LTP suggested a "tug-of-war" model in which lipid exchange between CD1 and LTP is on the basis of their respective affinities for lipids. LTPs constitute a previously unknown link between lipid metabolism and immunity and are likely to exert a profound influence on the repertoire of self, tumor, and microbial lipid antigens.

Type-2 activation of macrophages (M2) is an alternative pathway to the classic macrophage activation. These M2 cells are APC's that are presented in the Lamina-Propria of the gut as part of the gut associated immune system. These M2 cells will response with IL-10 expression instead of the classic Th1 cytokine response of macrophages as describe below.

Activated macrophages are used as antigen presenting cells (APCs). Antigen recognition by T cells is the key event controlling the adaptive immune response.

The classical pathway of IFN-$\gamma$ dependent activation of macrophages by Th1-type responses is a well-established feature of cellular immunity. Macrophage activation depends on the products of specifically activated T helper—Th1-type lymphocytes and natural killer cells—in particular, IFN-$\gamma$ and cytokine network involving IL-12 and IL-18, which are produced by APCs. The concept of an alternative pathway of macrophage activation by the Th2-type cytokines IL-4 and IL-13, together with IL-10, has gained credence in the past decade, to account for a distinctive macrophages phenotype that is consistent with a different role in humoral immunity and repair.

IL-4 and IL-13 up-regulates expression of the mannose receptor and MHC class II molecules by macrophages, which stimulate endocytosis and antigen presentation.

Immunoglobulins and immune complexes can bind both activating and inhibitory receptors for Fc and for complement. Also, Fc-receptor ligation induces marked effects on the release of cytokines, such as IL-12/IL-10 and IL-4, by APCs themselves and by other cells of the innate and acquired immune systems (Gordon S. Alternative Activation of Macrophages. Nat. Rev. Immunol. 3: 23-34; 2003).

Macrophages challenged with inflammatory stimuli (IFN-$\gamma$ for example) and introduced to immune complexes dramatically opposed in their action, instead of a Th1 response: elevated levels of IL-12 and moderate levels of IL-10 there is a dramatic decrease in IL-12 and an increase in IL-10 levels. IL-10 exerts immune-suppressive effects on macrophages. (Anderson, C. F. and Mosser, D. M. A Novel Phenotype for an Activated Macrophages: the Type 2 Activated Macrophage. J. Leukoc. Biol. 72: 101-106; 2002). IL-10 acts on a distinct plasma-membrane receptor to those for IL-4 and IL-13, and its effect on macrophage gene expression are different, involving a more profound inhibition of a range of antigen-presenting and effector functions, together with the activation of selected genes or functions (Gordon S. Alternative Activation of Macrophages. Nat. Rev. Immunol. 3: 23-34; 2003).

Hence, in addition to its effect on atherosclerosis and other diseases which are directly associated with oxidized LDL, it was further postulated that the immunomodulation and the anti-inflammatory effect induced by oxidized LDL (synthetic) analogs can be utilized in the treatment and prevention of other disease and disorders, directly or indirectly associated with endogenous oxidized LDL and other oxidized lipids. This was supported by several studies which were directed at immunotherapy of human autoimmune disease such as rheumatoid arthritis (RA), type I diabetes, and multiple sclerosis, either by modulation of individual immune pathways involved in inflammation or by tolerization to various antigens (Bielekova et al. Encephalitogenic potential of the myelin basic protein peptide (amino acids 83-99) in multiple sclerosis: Results of a phase II clinical trial with an altered peptide ligand. Nat. Med. 2000; 6:1167-1175; Kappos et al. Induction of a non-encephalitogenic type 2 T helper-cell autoimmune response in multiple sclerosis after administration of an altered peptide ligand in a placebo-controlled, randomized phase II trial. Nat. Med. 2000; 6:1176-1182).

Hence, there are ample data supporting the relation between lipids, inflammation and the immune system, indicating a direct linkage therebetween.

In an attempt to improve treatment of inflammation and diseases and disorders associated with oxidized lipids, the present inventors have designed novel synthetic oxidized phospholipids and structurally related compounds, which are devoid of the limitations associated oxidized LDL and other known oxidized phospholipids and lipids (as delineated hereinabove).

As is demonstrated in the Examples section that follows, while reducing the present invention to practice, it was indeed confirmed that oral and/or mucosal administration of the newly designed oxidized LDL analogs modulate the immune and/or inflammatory response to endogenous oxidized LDL, thereby reducing the inflammatory response in inflammatory diseases such as atherosclerosis and rheumatoid arthritis. These results clearly demonstrate the effect of exogenous oxidized lipids on inflammatory and immune processes which involve endogenous oxidized lipids.

Thus, according to one aspect of the present invention there are provided novel compounds, designed so as to mimic the immunomodulation effect induced by oxidized LDL and/or an inflammation associated with oxidized LDL and/or other oxidized lipids, while avoiding the limitations associated with oxidized LDL and other oxidized lipids and are thus highly suitable for oral/mucosal treatment of inflammatory associated diseases and disorders which involve oxidized lipids.

Since oxidized phospholipids are known as active components of ox LDL and further since biological membranes typically include phospholipids, and mainly phosphoglycerides, the compounds according to the present invention are structurally based on oxidized phospholipids in general and oxidized phosphoglycerides in particular.

Each of the compounds according to the present invention has the general formula I:

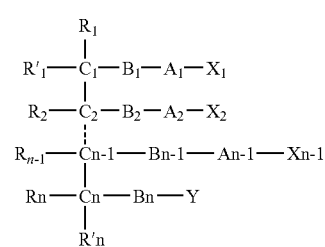

Formula I wherein:

n is an integer of 1-6, whereas if n=1, Cn, Bn, Rn, R'n and Y are absent;

each of $B_1, B_2, \ldots Bn-1$ and Bn is independently selected from the group consisting of oxygen, sulfur, nitrogen, phosphor and silicon, whereby each of the nitrogen, phosphor and silicon is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo;

each of $A_1, A_2, \ldots An-1$ and An is independently selected from the group consisting of CR"R'", C=O and C=S, Y is selected from the group consisting of hydrogen, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-biposphonate, pyrophosphate, phosphoethanolamine-diethylenetriamine-pentaacetate, dinitrophenyl-phosphoethanolamine and phsophoglycerol; and each of $X_1, X_2, \ldots Xn-1$ is independently a saturated or unsaturated hydrocarbon having the general formula II:

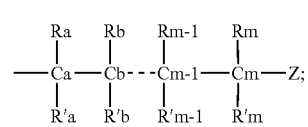

Formula II wherein:

m is an integer of 1-26; and

Z is selected from the group consisting of:

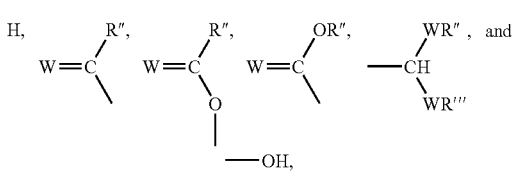

whereas:

W is selected from the group consisting of oxygen, sulfur, nitrogen and phosphor, whereby each of the nitrogen and phosphor is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo; and in at least one of $X_1, X_2, \ldots Xn-1$ Z is not hydrogen; and wherein:

each of $R_1$, $R'_1$, $R_2$, ... $Rn-1$, $Rn$, $R'n$, each of $R''$ and $R'''$ and each of $Ra$, $R'a$, $Rb$, $R'b$, ... $Rm-1$, $R'm-1$, $Rm$ and $R'm$ is independently selected from the group consisting of hydrogen, a bond, alkyl, alkenyl, alkylnyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, or, alternatively, at least two of $R_1$, $R'_1$, $R2$, ... $Rn-1$, $Rn$ and $R'n$ and/or at least two of $Ra$, $R'a$, $Rb$, $R'b$, ... $Rm-1$, $R'm-1$, $Rm$ and $R'm$ form at least one four-, five- or six-membered aromatic, heteroaromatic, alicyclic or heteroalicyclic ring; and each of $C_1$, $C_2$, ..., $Cn-1$, $Cn$, and each of $Ca$, $Cb$, ... $Cm-1$ and $Cm$ is a chiral or non-chiral carbon atom, whereby each chiral carbon atom, has a S-configuration and/or a R-configuration, a pharmaceutically acceptable salt, a prodrug, a hydrate or a solvate thereof.

It will be appreciated by one of ordinary skill in the art that the feasibility of each of the substituents (e.g., $R_1$-$Rn$, $Ra$-$Rm$, $R''$, $R'''$) to be located at the indicated positions depends on the valency and chemical compatibility of the substituent, the substituted position and other substituents. Hence, the present invention is aimed at encompassing all the feasible substituents for any position.

As used herein throughout, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, sulfonyl, sulfinyl, sulfonamide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. Representative examples are piperidine, piperazine, tetrahydro furane, tetrahydropyrane, morpholino and the like.

A "hydroxy" group refers to an —OH group.

An "azide" group refers to a —N=N group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R group, where R is hydrogen, alkyl, alkenyl, cycloalkyl, aryl, heteroaryl (bonded through a ring carbon) or heteroalicyclic (bonded through a ring carbon) as defined herein.

An "aldehyde" group refers to a carbonyl group, where R is hydrogen.

A "thiocarbonyl" group refers to a —C(=S)—R group, where R is as defined herein.

A "C-carboxy" group refers to a —C(=O)—O—R groups, where R is as defined herein.

An "O-carboxy" group refers to an RC(=O)—O— group, where R is as defined herein.

An "oxo" group refers to a =O group.

A "carboxylic acid" group refers to a C-carboxyl group in which R is hydrogen.

A "halo" group refers to fluorine, chlorine, bromine or iodine.

A "trihalomethyl" group refers to a —CX$_3$ group wherein X is a halo group as defined herein.

A "sulfinyl" group refers to an —S(=O)—R group, where R is as defined herein.

A "sulfonyl" group refers to an —S(=O)$_2$—R group, where R is as defined herein.

An "S-sulfonamido" group refers to a —S(=O)$_2$—NR$_2$ group, with each of R as is defined herein.

An "N-sulfonamido" group refers to an RS(=O)$_2$—NR group, where each of R is as defined herein.

An "O-carbamyl" group refers to an —OC(=O)—NR$_2$ group, where each of R is as defined herein.

An "N-carbamyl" group refers to an ROC(=O)—NR— group, where each of R is as defined herein.

An "O-thiocarbamyl" group refers to an —OC(=S)—NR$_2$ group, where each of R is as defined herein.

An "N-thiocarbamyl" group refers to an ROC(=S)NR— group, where each of R is as defined herein.

An "Amino" group refers to an —NR$_2$ group where each of R is as defined herein.

A "C-amido" group refers to a —C(=O)—NR$_2$ group, where each of R is as defined herein.

An "N-amido" group refers to an RC(=O)—NR— group, where each of R is as defined herein.

An "urea" group refers to an —NRC(=O)—NR$_2$ group, where each of R is as defined herein.

A "guanidino" group refers to an —RNC(=N)—NR$_2$ group, where each of R is as defined herein.

A "guanyl" group refers to an R$_2$NC(=N)— group, where each of R is as defined herein.

A "nitro" group refers to an —NO$_2$ group.

A "cyano" group refers to a —C≡N group.

The term "phosphonyl" or "phosphonate" describes a —P(=O)(OR)$_2$ group, with R as defined hereinabove. The term "phosphate" describes an —O—P(=O)(OR)$_2$ group, with each of R as defined hereinabove.

A "phosphoric acid" is a phosphate group is which each of R is hydrogen.

The term "phosphinyl" describes a —PR$_2$ group, with each of R as defined hereinabove.

The term "thiourea" describes a —NR—C(=S)—NR— group, with each of R as defined hereinabove.

The term "saccharide" refers to one or more sugar unit, either an open-chain sugar unit or a cyclic sugar unit (e.g., pyranose- or furanose-based units), and encompasses any monosaccharide, disaccharide and oligosaccharide, unless otherwise indicated.

As is shown in the general formula I above, the compounds according to the present invention include a backbone of 1-6 carbon atoms, whereby at least one of these backbone carbon atoms is covalently attached to hydrogen, a hydrocarbon group (alkyl, aryl, etc.), a carboxy group (e.g., acyl, carboxylic acid, etc.) or to a phosphoryl group (which is also referred to herein as a phosphate group or simply as a phosphate), and the other 1-5 backbone carbon atoms are covalently attached to hydrocarbon chains (X$_1$-Xn−1) via a heteroatom (B$_1$-Bn in the general formula I above). These hydrocarbon chains can include saturated or unsaturated, substituted or unsubstituted chains, optionally interrupted by aromatic, alicyclic, heteroalicyclic and/or heteroaromatic moieties, all as described hereinabove and depicted in general formula II, whereby at least one of these chains is terminating with an oxidized group, defined hereinabove as Z that is different than hydrogen.

As used herein, the term "hydrocarbon" refers to a compound that includes hydrogen atoms and carbon atoms, covalently attached therebetween. When the hydrocarbon is saturated, each of Ca-Cm is covalently attached to its neighboring atoms via a single sigma bond. When the hydrocarbon is unsaturated, at least two neighboring atoms of Ca-Cm are attached therebetween via a double bond or a triple bond.

Each of the hydrocarbon chains according to the present invention can include between 1 and 26 carbon atoms, more preferably between 3 and 26 carbon atoms. Hydrocarbon chains that terminate with the oxidized group Z are typically lower-sized chains, preferably having between 3 and 10 carbon atoms, more preferably between 3 and 6 carbon atoms, not including the carbon atom in the oxidized group.

LDL is a lipoprotein composed of functionally different moieties (components). Among these moieties are phospholipids, which are considered to play an important role in the effect of oxidized LDL on plaque related diseases.

As used herein throughout, the term "moiety" or "component" refers to a major portion of a functional molecule which is linked to another molecule, while retaining its activity. Phospholipids are natural substances that include a non-polar lipid group and a highly polar phosphatidyl group at the end. The most prevalent phospholipids in nature are phosphoglycerides, which include a glycerol backbone and fatty acyl moieties attached thereto. Phosphoglycerides such as 1,2-O-fatty acyl phosphoglycerides, as well as oxidative modifications thereof such as POVPC and PGPC, have been involved in atherogenesis related studies, as is described in detail hereinabove.

In addition to LDL, phospholipids and phosphoglycerides, other lipids are involved in various biological processes such as inflammation. These include, for example, sphingolipids, glycolipids and other membrane lipids.

The compounds of the present invention described above have been primarily designed according to the basic structure of phosphoglycerides, such that in a preferred embodiment of the present invention n in the general formula I above equals 3. Such compounds are referred to herein as oxidized phosphoglyceride analogs, while the compounds of the present invention are collectively referred to herein as oxidized lipids and include analogs and derivatives thereof.

As used herein throughout, the term "analogs" refers to compounds that are structurally related to the subject molecule (e.g., oxidized phospholipids, oxidized LDL, etc.) and can therefore exert the same biological activity.

The term "derivatives" refers to subject molecules which has been chemically modified but retain a major portion thereof unchanged, e.g., subject molecules which are substituted by additional or different substituents, subject molecules in which a portion thereof has been oxidized or hydrolysed, and the like.

In view of the inherent instability of the O-fatty acyl moiety in naturally occurring phosphoglycerides, as well as in other structurally related compounds, which results from its high susceptibility to fast hydrolysis in biological systems by phospholipase A$_2$ (see, for example, "A Textbook of Drug Design and Development", Povl Krogsgaard-Larsen and Hans Bundgaard, eds., Harwood Academic Publishers, chapter 13, pages 478-480), the compounds of the present invention have been designed to include at least one O-fatty ether moiety, such that in the general formula I above, when n equals 3, at least one of $A_1$ and $A_2$ is preferably a CR"R'" group. Compounds in which one of $A_1$ and $A_2$ is a CR"R'" group are referred to herein as mono-etherified phosphoglyceride analogs, while compounds in which both $A_1$ and $A_2$ are CR"R'" are referred to herein as di-etherified phosphoglyceride analogs, and are characterized by improved in vivo stability, particularly as compared with the presently known synthetic oxidized phosphoglycerides (e.g., POVPC and PGPC).

As is defined under the general formula I above, when n equals 3, at least one of $X_1$ and $X_2$ is a hydrocarbon chain that terminates with an oxidized group, such that Z is not hydrogen. However, since in naturally occurring oxidized LDL derivatives the oxidized alkyl chain is typically located at the second position, and since it has been demonstrated that the biological activity of several phospholipids directly depends on the structure thereof (see the Background section for a detailed discussion), in another preferred embodiment of the present invention, $X_2$ is a hydrocarbon chain that terminates with an oxidized group.

As is further described in the general formula II hereinabove, the oxidized group can be, for example,

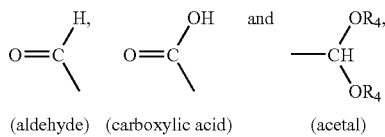

(aldehyde)   (carboxylic acid)   (acetal)

as well as derivatives thereof such as, for example, any carboxy or thiocarboxy derivative (e.g., a carboxylic ester in which W is oxygen and R" is an alkyl, aryl, cycloalkyl and the like), as defined hereinabove, imino derivatives (in which W in a nitrogen atom), amido derivatives (in which W is oxygen and R" is an amine), phosphine or phosphonate derivatives and many more, as defined hereinabove.

One example of a novel etherified oxidized phosphoglyceride according to the present invention is 2,5'-Aldehyde Lecithin Ether (ALLE): 1-hexadecyl-2-(5'-oxo-pentanyl)-sn-glycero-3-phosphocholine (D-ALLE),3-hexadecyl-2-(5'-oxo-pentanyl)-sn-glycero-1-phosphocholine (L-ALLE)], and the racemic mixture thereof, the synthesis and use of which are further detailed in the Examples section which follows.

However, as aldehydes are known as unstable compounds, which tend to be easily oxidized, preferred examples of novel etherified oxidized phosphoglycerides according to the present invention include the acid derivative 1-Hexadecyl-2-(5'-Carboxy-butyl)-sn-glycero-3-phosphocholine (also referred to hereinafter as IC-201), and its corresponding acetals 1-Hexadecyl-2-(5',5'-Dimethoxy-pentyloxy)-sn-glycero-3-phosphocholine and 1-Hexadecyl-2-(5',5'-Diethoxy-pentyloxy)-sn-glycero-3-phosphocholine (see FIG. 10 for 2-D structural formulas), the synthesis and use of which are also further detailed in the Examples section which follows.

While the oxidized lipids described above are derived from phosphoglycerides, oxidized lipids derived from, for example, sphingolipids, are also within the scope of the present invention. Such oxidized sphingolipids analogs according to the present invention have the general formula I above, wherein n equals 3, Y is hydrogen, $B_2$ is NH, and $A_2$ is C=O, whereby the hydrocarbon chain terminating with an oxidized group is attached either to the amide, as $X_2$ or to $C_1$.

While oxidized phosphoglycerides are derived from glycerol, which is a monosaccharide molecule, and oxidized sphingolipids are derived from sphingosine, an amino alcohol, it is envisioned that oxidized phospholipids derived from other biologically prevalent alcohol base units would exert the same effect. Furthermore, since no correlation between the distance of the oxidized moiety and the phosphatidyl moiety in oxidized phospholipids has been established, it is envisioned that oxidized lipids that are derived from a 4-6 carbon atoms backbone would retain structure characteristics similar to those of oxidized phosphoglycerides and as such in all probability would possess the same antigenicity and immune modulation activity, and employed and applied similarly to the oxidized phosphoglyceride derivatives described herein.

A preferred example of such an alcohol base unit is a monosaccharide base unit, such as, for example, glucose, erythritol and threitol.

Thus, in another preferred embodiment, the compounds according to the present invention include up to 6 carbon atoms in the backbone chain. The carbon atoms in the backbone chain can be linearly attached one to another, so as to form an open-chain monosaccharide backbone, or alternatively, can form a heteroalicyclic monosaccharide backbone, namely a pyranose or furanose backbone, such that in the general formula above, one of $R_1$ and $R'_1$, is covalently attached to one of Rn or R'n, via an etheric bond (an R—O—R bond)

Still alternatively, the compounds of the present invention can include 4-6 carbon atoms in the backbone chain, which form a non-saccharidic ring, namely a four-, five- or six-membered carbocyclic or heteroalicyclic ring, such that in the general formula I above one of $R_1$ and $R'_1$, is covalently attached to one of Rn or R'n, via different bonds (e.g., a sigma bond, a π bond, a carboxylic bond, an ether bond, a thioether bond and any other bond).

As is further described in the general formula I hereinabove, Y is either a phosphoryl moiety (e.g., phosphoryl choline, phosphoryl ethanolamine, etc.) or a non-phosphoryl moiety (e.g., hydrogen, acyl or alkyl). When Y is a non-phosphoryl moiety, the resultant compound is not a phospholipid, rather a diglyceride compound, for n=3, or any other alcohol-derived, e.g., monosaccharide-derived compound.

Since no particular activity of the phosphoryl group has been taught so far with respect to the immunomodulation activity of oxidized LDL, it is further envisioned that such non-phosphoryl compounds would retain similar structure characteristics as the above oxidized phospholipids and as such in all probability would posses antigenicity and immune modulation activity, and can be employed and applied similarly to the oxidized phospholipid derivatives described herein.

In an embodiment of the present invention, Y is a saccharide, as is defined hereinabove, and thus the compound according to the present invention is an oxidized analog of glycolipids.

In another embodiment, the compound is an oxidized analog of any membrane lipid.

The preferred structural features described above with respect to oxidized phosphoglycerides apply for all the compounds described hereinabove. Hence, in a preferred embodiment of the present invention, at least one of $A_1, A_2, \ldots$ and An−1 is a CR"R'" group, such that the compound include at least one etherified side chain. Due to the instability of an O-acyl side chain, it is further preferred that at least one of the oxidized groups in $X_1$-Xn−1 would be linked to such an etherified side chain.

Although naturally occurring phospholipids and oxidized phospholipids typically include O-acyl chains, there is evidence that thiol derivatives of oxidized phospholipids, which include, for example, S-acyl chains, may exert the same biological activity (see, for example, Reddy et al. Antitumor ether lipids: an improved synthesis of ilmofosine and an entioselective synthesis of an ilmofosine analog. Tetrahedron Letters. 1994; 17:2679-2682; Batia and Hajdu. Stereospecific synthesis of ether and thioether phospholipids. The use of L-glyceric acid as a chiral phospholipids precursor. J. Org. Chem. 1988; 53:5034-5039; Bosies et al. Lipids. 1987; 22:947; Bosies et al. Ger. Offen. DE 3,906,952 [C.A. 1991, 114, 102394w]; and Herrmann et al. NCI-EORTC Symposium on New Drugs in Cancer Therapy, Amsterdam, March 1992). As thiols are characterized by enhanced biostability, such compounds can further be highly beneficial.

Hence, in one embodiment of the present invention, at least one of $B_1$-Bn is sulfur, such that at least one of the side chains is a thiolated S-acyl or an s-alkyl chain. In another embodiment, at least one of $X_1$-Xn−1 which comprises an oxidized group is linked to such a thiolated side chain.

Alternatively, each of $B_1$-Bn can be a biocompatible heteroatom other than oxygen and sulfur, such as, for example, nitrogen, phosphor or silicon, as is described within the general formula I hereinabove.

Apart from the structural features delineated herein, the compounds of the present invention can be further substituted at any position thereof, e.g., at any of the side chain carbon atoms and at any of the backbone carbon atoms. While a myriad of possible substituents delineated hereinabove and encompassed by the present invention, preferred substituents include, for example, halo and aryl.

Although the compounds of the present invention have been basically designed from oxidized phospholipids such as phosphoglycerides, the present inventors also envisage that a single oxidized hydrocarbon chain, which is optionally attached to a polar group, would exert that same antigenicity and immunomodulation activity as the oxidized phospholipid analogs described above.

Such an oxidized hydrocarbon chain is a common feature of arachidonic acid metabolites. Arachidonic acid is a polyunsaturated fatty acid having 20 carbon atoms, which is produced in vivo by the enzymatic hydrolysis of phospholipids containing same. Upon its release, arachidonic acid is oxidized into a number of important autacoids by certain lipoxygenases and following a cascade of additional enzymatic reactions, the autacoids are metabolized into a family of classical prostaglandins (PG), prostacyclin ($PGI_2$) and thromboxane (TX) $A_2$, which are active in many biological pathways. All these metabolites include a common feature of a six-carbon chain terminating with an oxidizable double bond.

As is described hereinabove and is further demonstrated in the Examples section that follows, the presence of an oxidized group in oxidized LDL analogs that are designed for mimicking the immunomodulation induced by ox LDL, is essential. Thus, in comparative studies it was shown, for example, that Compound V, the non-oxidized compound corresponding to CI-201 (Compound VII), is non-active while CI-201 is (see, for example, Examples XIV and XV in the Examples section that follows). Furthermore, based on the metabolism pathway of arachidonic acid, it is assumed that other oxidized phospholipids undergo the same pathway, which results in the release of the oxidized side chain. As is further described hereinabove, the oxidized side chain preferably includes between 3 and 7 carbon atoms, and is therefore similar to the six-carbon chain feature on the arachidonic acid metabolites. Moreover, the CD1 mechanism described above, which suggest a role for lipids in the immune system, indicate that the hydrophilic head, i.e. the carbon-C2 and/or the carbon-C3 head group in CD1-d are most probably the antigenic epitope presented to the immune system as it is the part presenting by the CD1 groove that hide the hydrophobic part of the molecule, indicating a role of an hydrophilic epitope at carbon-C2.

In oxidized phospholipids such as phosphoglycerides, the oxidized side chain is attached to a phosphoglycerol backbone. However, as is mentioned hereinabove, no particular role for the phosphoglycerol backbone has been suggested.

Hence, in a preferred embodiment of the present invention, n equals 1, such that the compound of the present invention is a single hydrocarbon chain terminating with an oxidized group. While such an oxidized single hydrocarbon chain is non-polar, it can be attached to a polar group such as a phosphoryl group, such that in the general formula I hereinabove, when n equals 1, at least one of $R_1$ and $R'_1$ is a phosphate or phosphonate group. Alternatively, at least one of $R_1$ and $R'_1$ can be selected from other biocompatible polar groups such as, for example, peptides, saccharides and the like.

Depending on the substituents, each of the carbon atoms in each of the compounds described above, namely $C_1$-Cn and Ca-Cm, can be chiral or non-chiral. Any chiral carbon atom that is present in the compounds of the present invention can be either in an R-configuration, an S-configuration or racemic. Thus the present invention encompasses any combination of chiral and racemic carbon atoms, including all the possible stereoisomers, optical isomers, enantiomers, and anomers. As is demonstrated in the Examples section that follows, the compounds of the present invention can be synthesized while retaining a configuration of the starting material. The compounds of the present invention can be further selectively synthesized in terms of the stereochemistry of the oxidized group. Hence, by selecting the appropriate starting materials and the appropriate syntheses conditions, the optical purity (e.g., the inclusion of chiral and/or racemic carbons) and the obtained stereoisomers of the resulting compounds can be determined. In cases where racemic mixtures are obtained, known techniques can be used to separate the optical or stereo-isomers. Such techniques are described, for example, in "Organic chemistry, fourth Edition by Paula Yurkanis Bruice, page 180-185 and page 214, Prentice Hall, Upper Sadde River, N.J. 07458".

The present invention further encompasses any pharmaceutically acceptable salts, prodrugs, hydrates and solvates of the compounds described hereinabove.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. The prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolysed in vivo, to thereby provide the free compound (the parent drug). The selected ester may affect both the solubility characteristics and the hydrolysis rate of the prodrug.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. An example, without limitation, of a pharmaceutically acceptable salt would be a carboxylate anion and a cation such as, but not limited to, ammonium, sodium, potassium and the like.

The term "solvate" refers to a complex of variable stoichiometry (e.g., di-, tri-, tetra-, penta-, hexa-, and so on), which is formed by a solute (the compound of present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

As is detailed hereinbelow, the newly designed compounds of the present invention exert a highly beneficial immunomodulation activity and therefore can be utilized in various therapeutic applications. Utilizing these compounds in therapeutic application involves administration thereof either per se, or as a part of a pharmaceutical composition where it is mixed with suitable carriers or excipients.

Thus, according to another aspect of the present invention, there is provided a pharmaceutical composition, which comprises, as an active ingredient, any of the compounds described hereinabove in general formula I and the accompanying description, and a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the compounds (e.g., ALLE and CI-201 and other compounds depicted in the general formula I hereinabove) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

In a preferred embodiment of the present invention, the pharmaceutical compositions are designed for modulating an immune and/or inflammatory response via mucosal administration.

In another preferred embodiment of the present invention, the pharmaceutical compositions are designed modulating an immune and/or inflammatory response via oral administration.

Further preferably, the pharmaceutical compositions of the present invention are designed for nasal, or intraperitoneal administration, as is detailed hereinafter.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of a disorder (e.g., atherosclerosis) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See, e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress angiogenesis (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed hereinbelow.

Thus, in a preferred embodiment of the present invention, the pharmaceutical composition is packaged in a packaging material and identified in print, on or in the packaging material, for use in the treatment or prevention of an inflammation associated with an endogenous oxidized lipid. A list of representative examples of diseases and disorders associated with such an inflammation is provided hereinbelow.

As is further described in detail hereinbelow, the pharmaceutical composition of the present invention can further include an additional compound, which is useful in the treatment or prevention of the above inflammation.

As is described in detail in the Examples section that follows, representative examples of the newly designed compounds of the present invention have been found effective in modulating an immune response and/or an inflammatory response associated with endogenous oxidized LDL, thus leading to attenuation of diseases associated with endogenous oxidized LDL. These results clearly suggest that (i) modulation of an immune and/or inflammatory response to endogenous oxidized LDL in particular and endogenous oxidized lipids in general can be induced by any compound that is structurally related to an oxidized lipid; and (ii) compounds capable of modulating an immune and/or inflammatory response to oxidized lipids can be utilized to treat or prevent inflammation associated with endogenous oxidized lipids.

Hence, according to another aspect of the present invention there is provided a method of treating or preventing an inflammation associated with an endogenous oxidized lipid. The method according to this aspect of the present invention is effected by administering to a subject in need thereof a therapeutically effective amount of one or more oxidized lipids.

As used herein, the phrase "an endogenous oxidized lipid" refers to one or more oxidized lipids that are present or formed in vivo, as a result of inflammatory and other cell- or humoral-mediated processes.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the phrase "treating or preventing" includes abrogating, substantially inhibiting, slowing or reversing the progression of a disease, substantially ameliorating clinical symptoms of a disease or substantially preventing the appearance of clinical symptoms of a disease.

Examples of subjects suitable for such treatment include subjects suffering from a disease or disorder associated with an inflammation, as is detailed hereinbelow. Preferred individual subjects according to the present invention are mammals such as canines, felines, ovines, porcines, equines, and bovines. Preferably the individual subjects according to the present invention are humans.

The phrase "oxidized lipid" refers to a natural or, preferably, synthetically prepared, compound that has common structural features with a natural lipid, an oxidized lipid, and any components, moieties, analogs and derivatives thereof. For example, oxidized LDL is composed of several functionally and structurally different moieties, and this phrase encompasses any synthetically prepared compound that has common structural features with any one of these moieties. This phrase further encompasses any derivative of such analogs.

Representative examples of oxidized lipids include, without limitation, oxidized phospholipids, platelet activating factor analogs, plasmalogen analogs, substituted or unsubstituted 3-30 carbon atoms hydrocarbons terminating with an oxidized group, sphingolipids oxidized analogs, glycolipids oxidized analogs, oxidized analogs of membrane lipids and any analogs or derivatives thereof.

Phospholipids in general and phosphoglycerides in particular are well known lipids, which are also components of oxidized LDL. Phosphoglycerides are derivatives of phsophoglycerol, which include one or more fatty acyl or acyl groups attached to the phsophoglycerol backbone.

Hence, synthetically prepared oxidized phospholipids may be efficiently used in the method according to this aspect of the present invention. Representative examples of known synthetic oxidized phospholipids include, without limitation, 1-palmitoyl-2-azelaoyl-sn-glycero-3-phosphocholine, 1-hexadecyl-2-azelaoyl-sn-glycero-3-phosphocholine, 1-palmitoyl-2-glutaroyl-sn-glycero-3-phosphocholine (PGPC), 1-palmitoyl-2-(5-oxovaleroyl)-sn-glycero-3-phosphocholine (POVPC), and 1-palmitoyl-2-(9-oxononanoyl)-sn-glycero-3-phosphocholine.

More preferred examples of synthetic oxidized phospholipids include the compounds of the present invention, as described hereinabove, including those compounds in which $n=1$. The latter are delineated herein as substituted or unsubstituted 3-30 carbon atoms hydrocarbons terminating with an oxidized group.

Other compounds which are structurally related to oxidized phosphoglycerides, and can therefore be efficiently used in this and other aspects of the present invention, are platelet-activating factor (PAF) analogs.

PAF are 1-alkyl-2-acetyl-sn-glycero-3-phosphocholines, naturally occurring ether-linked glycerolipids. The alkyl chain at the sn−1 position is typically an unsaturated alkyl having 16-18 carbon atoms. Some well-known PAF analogs typically include substitution of the acyl moiety at the sn−2 position by a long-chain acyl moiety (e.g., a fatty acid acyl). Additional PAF analogs include an oxidative modification, either at the unsaturated O-alkyl chain present in the sn−1 position or at the fatty acyl chain present at the sn−2 position.

Representative examples of known PAF analogs that can be used in this context of the present invention include, without limitation, 1-palmitoyl-2-(9-oxononanoyl)-sn-glycero-3-phosphocholine, 1-hexadecyl-2-acetoyl-sn-glycero-3-phosphocholine, 1-octadecyl-2-acetoyl-sn-glycero-3-phosphocholine, 1-hexadecyl-2-butyroyl-sn-glycero-3-phosphocholine, 1-octadecyl-2-butyroyl-sn-glycero-3-phosphocholine, 1-palmitoyl-2-acetoyl-sn-glycero-3-phosphocholine, 1-octadecenyl-2-acetoyl-sn-glycero-3-phosphocholine, 1-hexadecyl-2-(homogammalinolenoyl)-sn-glycero-3-phosphocholine, 1-hexadecyl-2-arachidonoyl-sn-glycero-3-phosphocholine, 1-hexadecyl-2-eicosapentaenoyl-sn-glycero-3-phosphocholine, 1-hexadecyl-2-docosahexaenoyl-sn-glycero-3-phosphocholine, 1-octadecyl-2-methyl-sn-glycero-3-phosphocholine, 1-hexadecyl-2-butenoyl-sn-glycero-3-phosphocholine, Lyso PAF C16 and Lyso PAF C18. However, any other PAF analogs or derivatives thereof can further be used in this context of the present invention.

Additional compounds, which are structurally related to oxidized phosphoglycerides, and can therefore be efficiently used in this and other aspects of the present invention, are plasmalogen analogs.

Plasmalogens are 1-alkyl-2-acetyl-sn-glycero-3-phosphatidyl, naturally occurring ether-linked glycerolipids, in which the alkyl chain at the sn−1 position is typically saturated. Some well-known plasmalogen analogs typically include substitution of the acyl moiety at the sn−2 position by a long-chain acyl moiety (e.g., a fatty acid acyl) and further include an oxidative modification, either at the sn−1 position or at the sn−2 position.

Representative examples of known plasmalogen analogs that can be used in this context of the present invention include, without limitation, 1-O-1'-(Z)-hexadecenyl-2-[12-[(7-nitro-2-1,3-benzoxadiazol-4-yl)amino]dodecanoyl]-sn-glycero-3-phosphocholine, 1-O-1'-(Z)-hexadecenyl-2-oleoyl-sn-glycero-3-phosphocholine, 1-O-1'-(Z)-hexadecenyl-2-arachidonoyl-sn-glycero-3-phosphocholine, 1-O-1'-(Z)-hexadecenyl-2-docosahexaenoyl-sn-glycero-3-phosphocholine, 1-O-1'-(Z)-hexadecenyl-2-oleoyl-sn-glycero-3-phosphoethanolamine, 1-O-1'-(Z)-hexadecenyl-2-arachidonoyl-sn-glycero-3-phosphoethanolamine, and 1-O-1'-(Z)-hexadecenyl-2-docosahexaenoyl-sn-glycero-3-phosphoethanolamine. However, any other plasmalogen analogs or derivatives thereof can further be used in this context of the present invention.

As used herein, the phrase "an inflammation associated with an endogenous oxidized lipid" describes an inflammation that is associated with the in vivo formation or presence of one or more oxidized lipids (e.g., oxidized LDL, oxidized membrane lipids, etc.).

Inflammation is a protective response of the body to an injury. Several cytokines play key roles in mediating inflammatory reactions amongst are IFN-γ and IL-10. IFN-γ has been implicated in the pathogenesis of a variety of autoimmune and chronic inflammatory conditions. On the other hand, IL-10 inhibits IFN-γ production by activated immune cells such as TH2 and M2 cells this cytokine (IL-10) serve as the major anti-inflammatory "gate".

Excessive inflammation is oftentimes deleterious, involving or leading to a myriad of diseases and disorders. As is explained in detail hereinabove, excessive inflammatory response is typically associated with oxidized lipid epitopes.

As is shown in the Examples section that follows, modulating the immune response to oxidized LDL by synthetic oxidized LDL analogs is associated with an anti-inflammatory effect. This anti-inflammatory effect may be utilized in treating or preventing inflammation-associated disease or disorders in which endogenous oxidized LDL or any other endogenous oxidized lipid is implicated. Such diseases and disorders include, for example, diseases or disorders associated with plaque formation, including but not limited to atherosclerosis, atherosclerotic cardiovascular disease, cerebrovascular disease, peripheral vascular disease, stenosis, restenosis and in-stent-stenosis, as well as autoimmune diseases or disorders, neurodegenerative diseases or disorders, proliferative disease or disorders and aging processes.

Thus, representative examples of diseases or disorders associated with an inflammation, which in turn is associated with an endogenous oxidized lipids, and are therefore treatable by the method of the present invention include, for example, idiopathic inflammatory diseases or disorders, chronic inflammatory diseases or disorders, acute inflammatory diseases or disorders, autoimmune diseases or disorders, infectious diseases or disorders, inflammatory malignant diseases or disorders, inflammatory transplantation-related diseases or disorders, inflammatory degenerative diseases or disorders, diseases or disorders associated with a hypersensitivity, inflammatory cardiovascular diseases or disorders, inflammatory cerebrovascular diseases or disorders, peripheral vascular diseases or disorders, inflammatory glandular diseases or disorders, inflammatory gastrointestinal diseases or disorders, inflammatory cutaneous diseases or disorders, inflammatory hepatic diseases or disorders, inflammatory neurological diseases or disorders, inflammatory musculo-skeletal diseases or disorders, inflammatory renal diseases or disorders, inflammatory reproductive diseases or disorders, inflammatory systemic diseases or disorders, inflammatory connective tissue diseases or disorders, inflammatory tumors, necrosis, inflammatory implant-related diseases or disorders, inflammatory aging processes, immunodeficiency diseases or disorders, proliferative diseases and disorders and inflammatory pulmonary diseases or disorders, as is detailed hereinbelow.

Non-limiting examples of hypersensitivities include Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity, delayed type hypersensitivity, helper T lymphocyte mediated hypersensitivity, cytotoxic T lymphocyte mediated hypersensitivity, TH1 lymphocyte mediated hypersensitivity, and TH2 lymphocyte mediated hypersensitivity.

Non-limiting examples of inflammatory cardiovascular disease or disorder include occlusive diseases or disorders, atherosclerosis, a cardiac valvular disease, stenosis, restenosis, in-stent-stenosis, myocardial infarction, coronary arterial disease, acute coronary syndromes, congestive heart failure, angina pectoris, myocardial ischemia, thrombosis, Wegener's granulomatosis, Takayasu's arteritis, Kawasaki syndrome, anti-factor VIII autoimmune disease or disorder, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity, Chagas' disease or disorder, and anti-helper T lymphocyte autoimmunity.

Stenosis is an occlusive disease of the vasculature, commonly caused by atheromatous plaque and enhanced platelet activity, most critically affecting the coronary vasculature.

Restenosis is the progressive re-occlusion often following reduction of occlusions in stenotic vasculature. In cases where patency of the vasculature requires the mechanical support of a stent, in-stent-stenosis may occur, re-occluding the treated vessel.

Non-limiting examples of cerebrovascular diseases or disorders include stroke, cerebrovascular inflammation, cerebral hemorrhage and vertebral arterial insufficiency.

Non-limiting examples of peripheral vascular diseases or disorders include gangrene, diabetic vasculopathy, ischemic bowel disease, thrombosis, diabetic retinopathy and diabetic nephropathy.

Non-limiting examples of autoimmune diseases or disorders include all of the diseases caused by an immune response such as an autoantibody or cell-mediated immunity to an autoantigen and the like. Representative examples are chronic rheumatoid arthritis, juvenile rheumatoid arthritis, systemic lupus erythematosus, scleroderma, mixed connective tissue disease, polyarteritis nodosa, polymyositis/dermatomyositis, Sjogren's syndrome, Bechet's disease, multiple sclerosis, autoimmune diabetes, Hashimoto's disease, psoriasis, primary myxedema, pernicious anemia, myasthenia gravis, chronic active hepatitis, autoimmune hemolytic anemia, idiopathic thrombocytopenic purpura, uveitis, vasculitides and heparin induced thrombocytopenia.

Non-limiting examples of inflammatory glandular diseases or disorders include pancreatic diseases or disorders, Type I diabetes, thyroid diseases or disorders, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome.

Non-limiting examples of inflammatory gastrointestinal diseases or disorders disorders include colitis, ileitis, Crohn's disease, chronic inflammatory intestinal disease, inflammatory bowel syndrome, chronic inflammatory bowel disease, celiac disease, ulcerative colitis, an ulcer, a skin ulcer, a bed sore, a gastric ulcer, a peptic ulcer, a buccal ulcer, a nasopharyngeal ulcer, an esophageal ulcer, a duodenal ulcer and a gastrointestinal ulcer.

Non-limiting examples of inflammatory cutaneous diseases or disorders disorders include acne, and an autoimmune bullous skin disease.

Non-limiting examples of inflammatory hepatic diseases or disorders include autoimmune hepatitis, hepatic cirrhosis, and biliary cirrhosis.

Non-limiting examples of inflammatory neurological diseases or disorders include multiple sclerosis, Alzheimer's disease, Parkinson's disease, myasthenia gravis, motor neuropathy, Guillain-Barre syndrome, autoimmune neuropathy, Lambert-Eaton myasthenic syndrome, paraneoplastic neurological disease or disorder, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, Huntington's disease, AIDS associated dementia, amyotrophic lateral sclerosis (AML), multiple sclerosis, stroke, an inflammatory retinal disease or disorder, an inflammatory ocular disease or disorder, optic neuritis, spongiform encephalopathy, migraine, headache, cluster headache, and stiff-man syndrome.

Non-limiting examples of inflammatory connective tissue diseases or disorders include autoimmune myositis, primary Sjogren's syndrome, smooth muscle autoimmune disease or disorder, myositis, tendinitis, a ligament inflammation, chondritis, a joint inflammation, a synovial inflammation, carpal tunnel syndrome, arthritis, rheumatoid arthritis, osteoarthritis, ankylosing spondylitis, a skeletal inflammation, an autoimmune ear disease or disorder, and an autoimmune disease or disorder of the inner ear.

Non-limiting examples of inflammatory renal diseases or disorders include autoimmune interstitial nephritis and/or renal cancer.

Non-limiting examples of inflammatory reproductive diseases or disorders include repeated fetal loss, ovarian cyst, or a menstruation associated disease or disorder.

Non-limiting examples of inflammatory systemic diseases or disorders include systemic lupus erythematosus, systemic sclerosis, septic shock, toxic shock syndrome, and cachexia.

Non-limiting examples of infectious disease or disorder include chronic infectious diseases or disorders, a subacute infectious disease or disorder, an acute infectious disease or disorder, a viral disease or disorder, a bacterial disease or disorder, a protozoan disease or disorder, a parasitic disease or disorder, a fungal disease or disorder, a mycoplasma disease or disorder, gangrene, sepsis, a prion disease or disorder, influenza, tuberculosis, malaria, acquired immunodeficiency syndrome, and severe acute respiratory syndrome.

Non-limiting examples of inflammatory transplantation-related diseases or disorders include graft rejection, chronic graft rejection, subacute graft rejection, acute graft rejection hyperacute graft rejection, and graft versus host disease or disorder. Exemplary implants include a prosthetic implant, a breast implant, a silicone implant, a dental implant, a penile implant, a cardiac implant, an artificial joint, a bone fracture repair device, a bone replacement implant, a drug delivery implant, a catheter, a pacemaker, an artificial heart, an artificial heart valve, a drug release implant, an electrode, and a respirator tube.

Non-limiting examples of inflammatory tumors include a malignant tumor, a benign tumor, a solid tumor, a metastatic tumor and a non-solid tumor.

Non-limiting examples of inflammatory pulmonary diseases or disorders include asthma, allergic asthma, emphysema, chronic obstructive pulmonary disease or disorder, sarcoidosis and bronchitis.

An examples of a proliferative disease or disorder is cancer.

The implication of phospholipids and phospholipid metabolites in treating of preventing diseases and syndromes such as, for example, oxidative stress of aging (Onorato J M, et al, Annal N Y Acad Sci 1998 Nov. 20; 854:277-90), rheumatoid arthritis (RA)(Paimela L, et al. Ann Rheum Dis 1996 August; 55(8):558-9), juvenile rheumatoid arthritis (Savolainen A, et al, 1995; 24(4):209-11), inflammatory bowel disease (IBD)(Sawai T, et al, Pediatr Surg Int 2001 May; 17(4): 269-74) and renal cancer (Noguchi S, et al, Biochem Biophys Res Commun 1992 Jan. 31; 182(2):544-50), has been recently reported, and thus further support the beneficial use of oxidized LDL analogs in the treatment or prevention of these diseases or disorders.

According to the method of the present invention, the oxidized lipids can be administered to a subject by various routes, including, for example, the oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular routes. However, as is described in detail herein throughout and is further demonstrated in the Examples section that follows, preferred routes of administration include the oral, mucosal, nasal, intradermal (subcutaneous) and intraperitoneal routes.

Hence, in one embodiment, 0.1-100 mg/kg of an oxidized lipid is administered intraperitoneally, in a suitable carrier such as but not limited to PBS or glycerol, one to three times, every week, on a chronic or alternate regiment.

In another embodiment, 0.1-100 mg/kg of an oxidized lipid is administered nasally, in a suitable carrier such as but not limited to PBS or glycerol, one to three times, every week, on a chronic or alternate regiment.

In still another embodiment, 0.1-100 mg/kg of an oxidized lipid is administered subcutaneously, in a suitable carrier such as but not limited to PBS or glycerol, one to three times, every week, on a chronic or alternate regiment.

In yet another embodiment, 0.1-100 mg/kg of an oxidized lipid is administered orally, in a suitable carrier such as but not limited to PBS or glycerol, one to three times, every week, on a chronic or alternate regiment.

The pharmaceutical compositions and the method according to the present invention, described hereinabove, may further involve the administration of one or more additional compounds that are capable of treating or preventing an inflammation associated with endogenous oxidized lipid as delineated hereinabove.

The methods according to the present invention can therefore involve co-administering, prior to, concomitant with or after the administration of the oxidized lipids, a therapeutically effective amount of one or more of such additional compounds, while the pharmaceutical composition according to the present invention may include, in addition to the compounds of the present invention, such additional compounds.

Representative examples of additional compounds that are capable of treating or preventing an inflammation associated with endogenous oxidized lipid delineated hereinabove, and are therefore usable is the context of this embodiment of the present invention include, without limitation, HMGCoA reductase inhibitors (statins), mucosal adjuvants, corticosteroids, steroidal anti-inflammatory drugs, non-steroidal anti-inflammatory drugs, analgesics, growth factors, toxins, cholesteryl ester transfer protein (CETP) inhibitors, perixosomes, proliferative activated receptor (PPAR) agonists, anti-atherosclerosis drugs, anti-proliferative agents, ezetimide, nicotinic acid, squalen inhibitors, an ApoE Milano, HSPs, Beta-2-glycoprotein-I and any derivative and analog thereof.

HMGCoA reductase inhibitors (statins) are well known drugs that effectively reduce LDL-cholesterol levels by inhibiting the enzyme that regulates the rate of cholesterol production and increasing the clearance of LDL-cholesterol present in the blood by the liver. Non-limiting examples of commonly prescribed statins include Atorvastatin, Fluvastatin, Lovastatin, Pravastatin and Simvastatin.

Ezetimibe is the first of a new class of cholesterol absorption inhibitors that potently and selectively inhibits dietary and biliary cholesterol absorption at the brush border of the intestinal epithelium, without affecting the absorption of triglyceride or fat-soluble vitamins. Ezetimibe thus reduces overall cholesterol delivery to the liver, secondarily inducing increased expression of LDL receptors, resulting in an increased removal of LDL-C from the plasma.

Peroxisome is a single-membrane organelle present in nearly all eukaryotic cells. One of the most important metabolic processes of the peroxisome is the β-oxidation of long and very long chain fatty acids. The peroxisome is also involved in bile acid synthesis, cholesterol synthesis, plasmalogen synthesis, amino acid metabolism, and purine metabolism.

Nicotinic acid is a known agent that lowers total cholesterol, LDL-cholesterol, and triglyceride levels, while raising HDL-cholesterol levels. There are three types of nicotinic acid drugs: immediate release, timed release, and extended release. Nicotinic acid or niacin, the water-soluble B vitamin, improves all lipoproteins when given in doses well above the vitamin requirement.

Squalene, an isoprenoid compound structurally similar to beta-carotene, is an intermediate metabolite in the synthesis of cholesterol. In humans, about 60 percent of dietary squalene is absorbed. It is transported in serum generally in association with very low density lipoproteins and is distributed ubiquitously in human tissues, with the greatest concentration in the skin, where it is one of the major components of skin surface lipids. Squalene inhibitors (e.g., monooxygenase and synthase) serve as cholesterol biosynthesis inhibitors.

Proliferative Activated Receptor (PPAR) agonists, e.g., fibrates, are fatty acid-activated members of the nuclear receptor superfamily that play important roles in lipid and glucose metabolism, and have been implicated in obesity-related metabolic diseases such as hyperlipidemia, insulin resistance, and coronary artery disease. Fibrates are generally effective in lowering elevated plasma triglycerides and cholesterol and act as PPAR agonists. The most pronounced effect of fibrates includes a decrease in plasma triglyceride-rich lipoproteins (TRLs). Levels of LDL cholesterol (LDL-C) generally decrease in individuals with elevated baseline plasma concentrations, and HDL cholesterol (HDL-C) levels are usually increased when baseline plasma concentrations are low. Non-limiting examples of commonly prescribed fibrates include bezafibrate, gemfibrozil and fenofibrate.

Cholesteryl Ester Transfer Protein (CETP) inhibitors play a major role in atherogenesis, by reducing cholesteryl ester accumulation within macrophages and the arterial wall, and thus reducing foam cell formation and affecting the cholesterol absorption. The most promising presently known CETP inhibitor is avisimibe.

ApoA-I Milano is typically used as a recombinant complex with phospholipid (ETC-216) and produces significant regression of coronary atherosclerosis.

Co-administration of mucosal adjuvants has been shown to be essential in preventing the invasion of infectious agents through mucosal surfaces. In the early stages of induction of mucosal immune response, the uptake of orally or nasally administered antigens is achieved through a unique set of antigen-sampling cells, M cells located in follicle-associated epithelium (FAE) of inductive sites. After successful uptake, the antigens are immediately processed and presented by the underlying dendritic cells (DCs).

Non-limiting examples of non-steroidal anti-inflammatory drugs include oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone.

Non-limiting examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Non-limiting examples of analgesics (pain relievers) include aspirin and other salicylates (such as choline or magnesium salicylate), ibuprofen, ketoprofen, naproxen sodium, and acetaminophen.

Growth factors are hormones which have numerous functions, including regulation of adhesion molecule production, altering cellular proliferation, increasing vascularization, enhancing collagen synthesis, regulating bone metabolism and altering migration of cells into given area. Non-limiting examples of growth factors include insulin-like growth factor-1 (IGF-1), transforming growth factor-β (TGF-β), a bone morphogenic protein (BMP) and the like.

Non-limiting examples of toxins include the cholera toxin, which also serves as an adjuvant.

Non-limiting examples of anti-proliferative agents include an alkylating agent such as a nitrogen mustard, an ethylenimine and a methylmelamine, an alkyl sulfonate, a nitrosourea, and a triazene; an antimetabolite such as a folic acid analog, a pyrimidine analog, and a purine analog; a natural product such as a vinca alkaloid, an epipodophyllotoxin, an antibiotic, an enzyme, a taxane, and a biological response modifier; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gonadotropin-releasing hormone analog. Specific examples of chemotherapeutic agents include, for example, a nitrogen mustard, an epipodophyllotoxin, an antibiotic, a platinum coordination complex, bleomycin, doxorubicin, paclitaxel, etoposide, 4-OH cyclophosphamide, and cisplatinum.

The HSP family consists of approximately 25 proteins discerned by their molecular weights with highly conserved structures. Almost all humans have cellular and humoral immune reactions against microbial heat-shock protein 60 (HSP60). Because a high degree of antigenic homology exists between microbial (bacterial and parasitic) and human HSP60, the 'cost' of immunity to microbes might be the danger of cross-reactivity with human HSP60 expressed by the endothelial cells of stressed arteries. Genuine autoimmunity against altered autologous HSP60 might trigger this process also (Wick et al. Atherosclerosis as an autoimmune disease: an update. TRENDS in Immunology. 2001; 22(12):665-669). HSP has been implicated as a target autoantigen in several experimental autoimmune diseases (arthritis, type I diabetes). Anti-HSP65 as well as anti-HSP60 antibodies have been demonstrably associated with atheromatous lesions in humans. Studies conducted in rabbits and mice show that the generation of an HSP65-induced immune response by immunization with the recombinant protein or with an HSP65-rich preparation of *Mycobacterium tuberculosis* enhances atherogenesis. As autoimmune processes pointing to HSP65 as a possible antigenic candidate, creating a state of unresponsiveness by induction of mucosal "tolerization" has been employed in order to block these responses, our group reported that early atherosclerosis was attenuated in HSP65-fed mice, compared with either BSA or PBS fed mice (Harats et al. Oral tolerance with heat shock protein 65 attenuates *mycobacterium tuberculosis* induced and high fat diet driven atherosclerosis lesions. J Am Coll Cardiol. 2002; 40:1333-1338), this was further supported by Maron who demonstrated that nasal vaccination with HSP reduces the inflammatory process associated with atherosclerosis (Maron et al. Mucosal administration of heat shock protein-65 decreases atherosclerosis and inflammation in aortic arch of low density lipoprotein receptor-deficient mice. Circulation. 2002; 106: 1708-1715).

Beta-2-glycoprotein I (beta2GPI) is a phospholipid binding protein shown to serve as a target for prothrombotic antiphospholipid antibodies. It has recently been demonstrated to drive an immune mediated reaction and enhance murine atherosclerosis. β-Antibodies to beta-2-GPI have the ability to activate monocytes and endothelial cells and can induce an immune response to beta2GPI in atherosclerosis-prone mice accelerated atherosclerosis. When beta2GPI-reactive lymph node and spleen cells were transferred to LDL-receptor-deficient mice they promoted fatty streak formation, proving a direct proatherogenic role for beta2GPI-specific lymphocytes. Inducing immunological tolerance to beta2GPI by prior oral feeding with the antigen resulted in a significant reduction in the extent of atherosclerotic lesions. Thus, beta2GPI is a candidate player in the atherosclerotic plaque, and can possibly be employed as an immunomodulator of plaque progression. Oral feeding with of beta2GPI inhibited lymph node cell reactivity to beta2GPI in mice immunized against the human protein. IL-4 and IL-10 production was upregulated in lymph node cells of beta2GPI-tolerant mice immunized against beta2GPI, upon priming with the respective protein. Thus, oral administration of beta2GPI is an effective means of suppressing atherogenesis in mice (George et al. Suppression of early atherosclerosis in LDL-receptor deficient mice by oral tolerance with beta2-glycoprotein I. Cardiovasc Res. 2004; 62(3):603-9).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include biochemical and immunological techniques. Such techniques are thoroughly explained in the literature. See, for example, "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; and "Methods in Enzymology" Vol. 1-317, Academic Press; Marshak et al., all of which are incorporated by reference as if fully set forth herein. Other general references are provided throughout this document. The procedures therein are believed to be well known in the art and are provided for the convenience of the reader. All the information contained therein is incorporated herein by reference.

Materials and General Methods

Animals:

Apo-E knockout mice: Apo-E knockout (Apo-E KO) mice used in our experiments are from the atherosclerosis prone strain C57BL/6J-Apoe$^{tm1unc}$. Mice homozygous for the Apoe$^{tm1unc}$ mutations show a marked increase in total plasma cholesterol levels which is unaffected by age or sex. Fatty streaks in the proximal aorta are found at 3 months of age. The lesions increase with age and progress to lesions with less lipid but more elongated cells, typical of a more advanced stage of pre-atherosclerotic lesion.

Strain Development: The Apoe$^{tm1unc}$ mutant strain was developed in the laboratory of Dr. Nobuyo Maeda at University of North Carolina at Chapel Hill. The 129-derived E14Tg2a ES cell line was used. The plasmid used is designated as pNMC109 and the founder line is T-89. The C57BL/6J strain was produced by backcrossing the Apoe$^{tm1unc}$ mutation 10 times to C57BL/6J mice (Plump et al., Severe hypercholesterolemia and atherosclerosis in apolipoprotein-E deficient mice created by homologous recombination in ES cells. *Cell* 1992; 71: 343-353; Zhang et al. Spontaneous hypercholesterolemia and arterial lesions in mice lacking apolipoprotein E. *Science* 1992; 258: 468-471).

The mice were maintained at the Sheba Hospital Animal Facility (Tel-Hashomer, Israel) on a 12-hour light/dark cycle, at 22-24° C. and fed a normal fat diet of laboratory chow (Purina Rodent Laboratory Chow No. 5001) containing 0.027% cholesterol, approximately 4.5% total fat, and water, ad libitum.

LDL-RD mice: LDL-RD Mice [LDLr<mlHer>LDL-/- (C57B/6 50% JSL 25% I129 25%)], 8-12 weeks old, were supplied by the Hadassah Hospital Animal Facility (Hadassah Hospital, Israel).

Lewis rats: Male Lewis rats, aged 9-11 weeks, were supplied by Harlan laboratories (ISRAEL)

Immunization:

I. Intraperitoneal immunization with ALLE: The phospholipid ether analog (ALLE D+L) was coupled to purified protein derivative from tuberculin (PPD). The stock solution of ALLE (D+L) was dissolved in ethanol (99 mg/ml). 5 mg ALLE (D+L), (50.5 µl from stock solution) was diluted to 5 mg/ml with 0.25M phosphate buffer, pH 7.2, by stirring at 0° C. (in an ice bath). 1.5 mg of D- and L-ALLE in 300 µl of phosphate buffer were added to 0.6 mg PPD dissolved in 300 µl of phosphate buffer. 1-Ethyl-3-(3-dimethylaminopropyl)-carbodiimid-HCl (5 mg; Sigma, St. Louis, Mo.) dissolved in 50 µl of water was added by stirring at 4° C. for 20 minutes. The remaining active sites were blocked with 100 µl of 1M glycine. Coupled compounds were dialyzed against phosphate-buffered saline (PBS), adjusted to 3 ml with PBS and stored at 4° C. Immunization with 0.3 ml (150 µg) antigen per mouse was performed intraperitoneally 4 times every 2 weeks.

II. Subcutaneous immunization with Human oxidized LDL: Human oxidized LDL was prepared from human plasma pool (d-1.019 to 1.063 gram/ml by ultracentrifugation) and was Cu-oxidized overnight (by adding 15 µl 1 mM $CuSO_4$ to each ml of LDL previously diluted to 1 mg/ml concentration). The oxidized LDL was dialyzed against PBS and filtrated. For immunization, oxidized LDL was dissolved in PBS and mixed with equal volumes of Freund's incomplete adjuvant. Immunizations were performed by single subcutaneous injection of 50 µg antigen/mouse in 0.2 ml volume. One to three days following the last oral administration the mice received one immunization, and were sacrificed 7-10 days post immunization.

Cholesterol Level Determination: At the completion of the experiment, 1-1.5 ml of blood was obtained by cardiac puncture, 1000 U/ml heparin was added to each sample and total plasma cholesterol levels were determined using an automated enzymatic technique (Boehringer Mannheim, Germany).

FPLC Analysis: Fast Protein Liquid Chromatography analysis of cholesterol and lipid content of lipoproteins was performed using Superose 6 HR 10/30 column (Amersham Pharmacia Biotech, Inc, Peapack, N.J.) on a FPLC system (Pharmacia LKB. FRAC-200, Pharmacia, Peapack, N.J.). A minimum sample volume of 300 µl (blood pooled from 3 mice was diluted 1:2 and filtered before loading) was required in the sampling vial for the automatic sampler to completely fill the 200 µl sample loop. Fractions 10-40 were collected, each fraction contained 0.5 ml. A 250 µl sample from each fraction was mixed with freshly prepared cholesterol reagent or triglyceride reagent respectively, incubated for 5 minutes at 37° C. and assayed spectrophotometrically at 500 nm.

Assessment of Atherosclerosis: Quantification of atherosclerotic fatty streak lesions was done by calculating the lesion size in the aortic sinus as previously described (Paigen et al. Quantitative assessment of atherosclerotic lesions in mice. *Atherosclerosis* 1987; 68: 231-140) and by calculating the lesion size in the aorta. Briefly, after perfusion with saline Tris EDTA, the heart and the aorta were removed from the animals and the peripheral fat cleaned carefully. The upper section of the heart was embedded in OCT medium (10.24% w/w polyvinyl alcohol; 4.26% w/w polyethylene glycol; 85.50% w/w nonreactive ingredients) and frozen. Every other section (10 µm thick) throughout the aortic sinus (400 µm) was taken for analysis. The distal portion of the aortic sinus was recognized by the three valve cusps that are the junctions of the aorta to the heart. Sections were evaluated for fatty streak lesions after staining with oil-red 0. Lesion areas per section were scored on a grid (Rubin et al. Inhibition of early atherogenesis in transgenic mice by human apolipoprotein A-I. *Nature* 1991; 353: 265-267) by an observer counting unidentified, numbered specimens. The aorta was dissected from the heart and surrounding adventitious tissue was removed. Fixation of the aorta and Sudan staining of the vessels were performed as previously described (Bauman and Mangold, *J. Org. Chem.* 31: 498, 1966).

Plasma Measurements and Quantification of Atherosclerotic Lesions: Plasma total cholesterol and total triglyceride levels were measured by COBAS MIRA. Hearts were collected upon sacrifice and the aortic root cryosections were stained using Oil-Red-O staining. Atherosclerotic lesion area was evaluated by computer analysis (Image Pro Plus) and supported by microscope evaluation as well.

Proliferation assays: Mice were fed with ALLE, POVPC or PBS as described for assessment of atherosclerosis, and then immunized one day following the last feeding with oxidized LDL prepared from purified human LDL as described above.

Proliferation was assayed eight days after immunization with the oxidized LDL as follows: Spleens or lymph nodes were prepared by meshing the tissues on 100 mesh screens. (Lymph nodes where immunization was performed, and spleens where no immunization performed). Red blood cells were lysed with cold sterile double distilled water (6 ml) for 30 seconds and 2 ml of NaCl 3.5% were added. Incomplete medium was added (10 ml), cells were centrifuge for 7 minutes at 1,700 rpm, resuspended in RPMI medium and counted in a haemocytometer at 1:20 dilution (10 µl cells+190 µl Trypan Blue). Proliferation was measured by the incorporation of $[^3H]$-Thymidine into DNA in triplicate samples of 100 µl of the packed cells ($2.5 \times 10^6$ cells/ml) in a 96 well microtiter plate. Triplicate samples of oxidized LDL (0-10 µg/ml, 100 µl/well) were added, cells incubated for 72 hours (37° C., 5% $CO_2$ and about 98% humidity) and 10 µl $^3$-[H]-Thymidine (0.5 µCi/well) were added. After an additional day of incubation the cells were harvested and transferred to glass fiber filters using a cell harvester (Brandel) and counted using β-counter (Lumitron). For assay of cytokines the supernatant was collected without adding $^3$-[H]-Thymidine and assayed by ELISA.

A separate group of mice were fed with ALLE or PBS and immunized with oxidized LDL as described above, one day following the last fed dose. Draining inguinal lymph nodes (taken 8 days after immunization) were collected from 3 mice from each of the groups, for the proliferation studies. $1 \times 10^6$ cells per ml were incubated in triplicates for 72 hours in 0.2 ml of culture medium in microtiter wells in the presence 10 µg/ml oxidized LDL. Proliferation was measured by the incorporation of $[^3H]$-thymidine into DNA during the final 12 hours of incubation. The results are expressed as the stimulation index (S.I.): the ratio of the mean radioactivity (cpm) of the antigen to the mean background (cpm) obtained in the absence of the antigen. Standard deviation was always <10% of the mean cpm.

Inflammatory Markers Evaluation in Serum: Serum was separated by centrifuge and stored at −70° C. Analysis of inflammatory markers was performed by ELISA (IL-10; R&D and SAA; BIOSOURCE).

RT-PCR analysis: Aortas, spleens and small intestine were removed out of treated and untreated mice (in a sterile manner) and freezed in liquid nitrogen. The organs were mashed on screen cup and the RNA production was performed using Rneasy kit (QIAGEN). RNA samples were examined in spectrophotometer and normalized relative to β-actin. Reverse transcription of RNA to cDNA and PCR with primers was performed with "Titan one tube RT-PCR kit" (ROCHE). Results were detected on 1% agarose gel and were documented on film.

Statistical Analysis: A one-way ANOVA test was used to compare independent values. $p<0.05$ was accepted as statistically significant.

Example I

Synthesis of the immunomodulizing antigens 2,5'-Aldehyde Lecithin Ether (ALLE) and POVPC

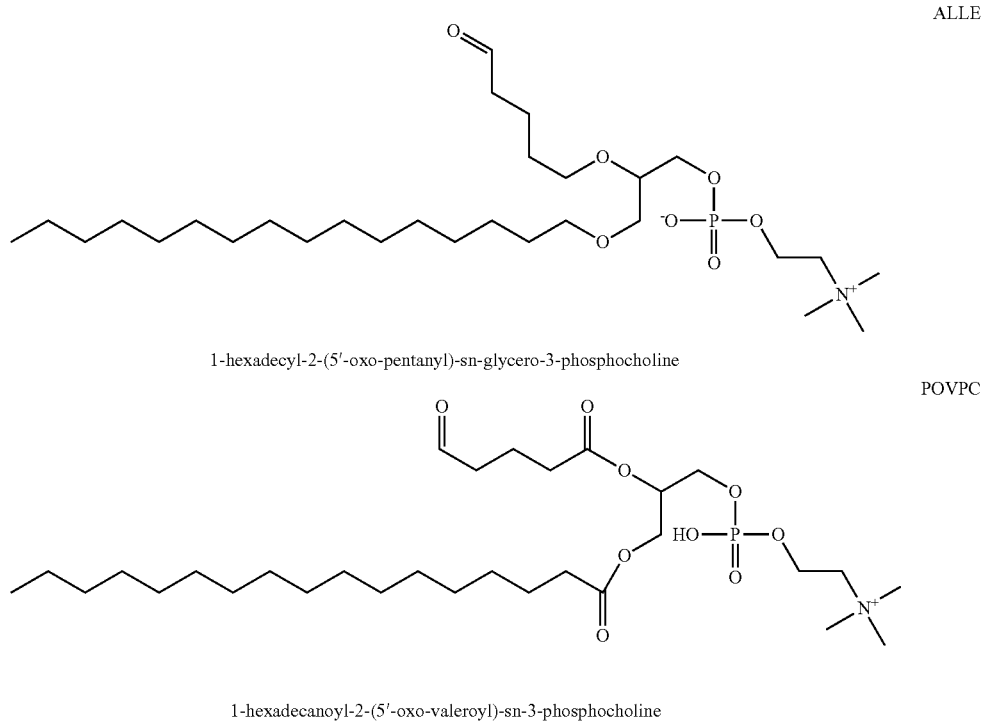

ALLE 1-hexadecyl-2-(5'-oxo-pentanyl)-sn-glycero-3-phosphocholine

POVPC 1-hexadecanoyl-2-(5'-oxo-valeroyl)-sn-3-phosphocholine

Synthesis of 2,5'-Aldehyde Lechitin Ether (ALLE)

2,5'-Aldehyde Lecithin Ether (ALLE) was synthesized according to a modification of general methods for synthesis of ether analogs of lecithins communicated by Eibl H., et al. Ann. Chem. 709:226-230, (1967), W. J. Baumann and H. K. Mangold, J. Org. Chem. 31,498 (1996), E. Baer and Buchnea JBC. 230,447 (1958), Halperin G et al Methods in Enzymology 129, 838-846 (1986). The following protocol refers to compounds and processes depicted in 2-D form in FIG. 1.

Hexadecyl-glycerol ether: D-Acetone glycerol (4 grams) for synthesis of L-ALLE or L-Acetone glycerol for synthesis of D-ALLE, powdered potassium hydroxide (approximately 10 grams) and hexadecyl bromide (9.3 grams) in benzene (100 ml) were stirred and refluxed for 5 hours, while removing the water formed by azeotropic distillation (compare W. J. Baumann and H. K. Mangold, J. Org. Chem. 29: 3055, 1964 and F. Paltauf, Monatsh. 99:1277, 1968). The volume of the solvent was gradually reduced to about 20 ml, and the resulting mixture was cooled to room temperature and dissolved in ether (100 ml). The resulting solution was washed with water (2×50 ml), and the solvent was removed under reduced pressure. A 100 ml mixture of 90:10:5 methanol:water:concentrated hydrochloric acid was added to the residue and the mixture was refluxed for 10 minutes. The product was extracted with ether (200 ml) and was washed consecutively with water (50 ml), 10% sodium hydroxide (20 ml) and again with water (volumes of 20 ml) until neutral. The solvent was removed under reduced pressure and the product (8.8 grams) was crystallized from hexane to give 7.4 grams of pure 1-hexadecyl-glyceryl ether (compound I, FIG. 1) for synthesis of D-ALLE or 3-hexadecyl-glyceryl ether for synthesis of L-ALLE.

5-Hexenyl-methane sulfonate: A mixture of 5-hexene-1-ol (12 ml) and dry pyridine (25 ml) was cooled to between −4° C. and −10° C. in an ice-salt bath. Methanesulfonyl chloride (10 ml) was added dropwise during a period of 60 minutes, and the mixture was kept at 4° C. for 48 hours. Ice (20 grams) was added, the mixture was allowed to stand for 30 minutes, and the product was extracted with ether (200 ml). The organic phase was washed with water (20 ml), 10% hydrochloric acid, 10% sodium bicarbonate (20 ml) and again with water (20 ml). The solvent was evaporated and the crude product was chromatographed on silica gel 60 (100 grams) using a mixture of 80:20 $CHCl_3$:EtOAc as eluent, to give 14 grams of 5-hexenyl-methane sulfonate.

1-Hexadecyloxy-3-trityloxy-2-propanol (for D-ALLE) or 3-Hexadecyloxy-1-trityloxy-2-propanol (for L-ALLE) (compound II): 1-Hexadecyloxy-glycerol (for D-ALLE) or 3-Hexadecyloxy-glycerol (for L-ALLE) (7.9 grams), triphenylchloromethane (8.4 grams) and dry pyridine (40 ml) were heated at 100° C. for 12 hours. After cooling, 300 ml of ether and 150 ml of ice-cold water were added, and the reaction mixture was transferred to a separatory funnel. The organic phase was washed consecutively with 50 ml of ice water, 1% potassium carbonate solution (until basic) and 50 ml of water, then dried over anhydrous sodium sulfate. The solvent was evaporated, the residue was dissolved in 150 ml of warm petroleum ether and the resulting solution was cooled at 4° C. over night. After filtration of the precipitate, the filtrate was evaporated and the residue was recrystallized from 20 ml of ethyl acetate at −30° C., yielding 8.2 grams of 1-Hexadecyloxy-3-trityloxy-2-propanol (for D-ALLE) or 3-hexadecyloxy-1-trityloxy-2-propanol (for L-ALLE) (compound II, FIG. 1), melting point 49° C.

1-Hexadecyl-2-(5'-hexenyl)-glyceryl ether (for D-ALLE) or 3-hexadecyl-2-(5'-hexenyl)-glyceryl ether (for L-ALLE) (compound IV): 1-Hexadecyloxy-3-trityloxy-2-propanol (for D-ALLE) or 3-Hexadecyloxy-1-trityloxy-2-propanol (for L-ALLE) (compound II, FIG. 1) (5.5 grams) was etherified with 5-hexenyl-methanesulfonate, using powdered potassium hydroxide in benzene solution as described above. The crude product 1-Hexadecyloxy-2-(5'-hexenyloxy)-sn-3-trityloxy-propane (for D-ALLE) or 3-Hexadecyloxy-2-(5'-hexenyloxy)-sn-3-trityloxy-propane (for L-ALLE) (compound III, FIG. 1) was dissolved in 100 ml of 90:10:5 methanol:water:concentrated hydrochloric acid and the mixture was refluxed for 6 hours. The product was extracted with ether, washed with water and the solvent was removed. The residue was dissolved in petroleum ether (100 ml) and was kept in 4° C. for overnight, causing most of the triphenyl carbinol to be deposited. After filtration and removal of the solvent from the filtrate the crude product was chromatographed on silica gel 60 (40 grams), using a mixture of 1:1 chloroform:petroleum ether as eluent, to give 1.8 grams of pure 1-hexadecyl-2-(5'-hexenyl)-glyceryl ether (for D-ALLE) or 3-hexadecyl-2-(5'-hexenyl)-glyceryl ether (for L-ALLE) (compound IV, FIG. 1).

1-Hexadecyl-2-(5'-hexenyl)-sn-glycero-3-phosphocholine (for D-ALLE) or 3-Hexadecyl-2-(5'-hexenyl)-sn-glycero-1-phosphocholine (for L-ALLE) (compound V): The following procedure is a modification of the method communicated by Eibl H., et al. Ann. Chem. 709:226-230, 1967.

A solution of 1-hexadecyl-2-hexenyl-glyceryl ether (for D-ALLE) or 3-hexadecyl-2-hexenyl-glyceryl ether (for L-ALLE) (compound IV, FIG. 1) (2 grams) in dry chloroform (15 ml) was added dropwise into a stirred, cooled solution (−4° C. to −10° C.) of dry triethylamine (3 ml) and 2-bromoethyl dichlorophosphate (1.25 ml, prepared as described hereinbelow) in dry chloroform (15 ml), during a period of 1 hour. The mixture was kept at room temperature for 6 hours and then heated to 40° C. for 12 hours. The resulting dark brown solution was cooled to 0° C. and 0.1M potassium chloride (15 ml) was added. The mixture was allowed to reach room temperature and was stirred for 60 minutes. Methanol (25 ml) and chloroform (50 ml) were added and the organic phase was washed with 0.1M hydrochloric acid (20 ml) and water (20 ml). The solvent was evaporated and the crude product was dissolved in methanol (15 ml), the solution was transferred to a culture tube and was cooled in an ice-salt bath. Cold trimethylamine (3 ml, −20° C.) was added and the tube was sealed. The mixture was heated to 55° C. for 12 hours, cooled to room temperature and the solvent evaporated using a stream of nitrogen. The residue was extracted with a mixture of 2:1 chloroform:methanol (25 ml) and washed with 1M potassium carbonate (10 ml) and water (2×10 ml). The solvent was removed under reduced pressure and the crude products were chromatographed on silica gel 60 (20 grams), using a mixture of 60:40 chloroform:methanol, to give 1.5 grams of 1-hexadecyl-2-(5'-hexenyl)-sn-glycero-3-phosphocholine (for D-ALLE) or 3-hexadecyl-2-(5'-hexenyl)-sn-glycero-1-phosphocholine (for L-ALLE) (compound V, FIG. 1). The structure of compound V was confirmed by NMR and mass spectrometry.

1-Hexadecyl-2-(5'-oxo-pentanyl)-sn-glycero-3-phosphocholine (for D-ALLE) or 3-Hexadecyl-2-(5'-oxo-pentanyl)-sn-glycero-1-phosphocholine (for L-ALLE) (compound VI)

A solution of Compound V (0.5 gram) in formic acid (15 ml) and 30% hydrogen peroxide (3.5 ml) was stirred at room temperature over night. The reaction mixture was diluted with water (50 ml), and extracted with a mixture of 2:1 chloroform:methanol (5×50 ml). The solvent was evaporated under reduced pressure and the residue was mixed with methanol (10 ml) and water (4 ml), then stirred at room temperature for 60 minutes. 80% phosphoric acid (2 ml) and potassium meta periodate (0.8 gram) were then added. The mixture was kept at room temperature overnight, diluted with water (50 ml) and extracted with 2:1 chloroform:methanol (50 ml). The organic phase was washed with 10% sodium bisulfite (10 ml) and water (10 ml). The solvent was removed under reduced pressure and the crude product was chromatographed on silica gel 60 (10 grams), using a mixture of 1:1 chloroform:methanol as eluent, to give 249 mg of 1-hexadecyl-2-(5'-oxo-pentanyl)-sn-glycero-3-phosphocholine (for D-ALLE) or 3-hexadecyl-2-(5'-oxo-pentanyl)-sn-glycero-1-phosphocholine (for L-ALLE) (compound VI, FIG. 1), exhibiting an $R_f$ of 0.15 (TLC system, 60:40:8 chloroform:methanol:water) and a positive reaction with dinitrophenylhydrazine. The chemical structure of Compound VI was confirmed by NMR and mass spectrometry.

In an alternative process, the ethylenic group was converted to an aldehyde group by ozonization and catalytic hydrogenation with palladium calcium carbonate.

Preparation of 2-bromoethyl dichlorophosphate: 2-Bromoethyl dichlorophosphate was prepared by dropwise addition of freshly distilled 2-bromoethanol (0.5 M, prepared as described in Gilman Org. Synth. 12:117, 1926) to an ice-cooled solution of freshly distilled phosphorous oxychloride (0.5 M) in dry chloroform, during a one hour period, followed by 5 hours reflux and vacuum distillation (bp 66-68° C. at 0.4-0.5 mm Hg). The reagent was stored (−20° C.) under nitrogen in small sealed ampoules prior to use (Hansen W. H et al. Lipids 17(6):453-459, 1982).

Synthesis of 1-Hexadecyl-2-(5'-carboxy-butyl)-sn-glycero-3-phosphocholine (CI-201)

1-Hexadecyl-2-(5'-oxo-pentanyl)-sn-glycero-3-phosphocholine (Compound VI, prepared as described above), 0.55 grams (0.001 mol), was dissolved in t-BuOH (30 ml). A solution of $NaClO_2$ (0.9 gram, 0.01 mol) and $NaH_2PO_4$ (0.96 gram, 0.07 mol) in 25 ml water was added dropwise during a period of 30 minutes and the mixture was stirred at room temperature for 3 hours. The reaction mixture was acidified to pH=3 with concentrated hydrochloric acid and extracted with a mixture of 2:1 chlroform:methanol. The organic phase was separated and the solvent was evaporated. The residue was purified by chromatography over silica gel using a mixture of chloroform:methanol:water (70:27:3), to give 1-hexadecyl-2-(5'-carboxy-butyl)-sn-glycero-3-phosphocholine (0.42 gram, 72% yield). NMR and mass spectrometry confirmed the chemical structure (Compound VII, FIG. 10).

Synthesis of 1-Hexadecyl-2-(5',5'-dimethoxy-pentyloxy)-sn-glycero-3-phosphocholine 1-Hexadecyl-2-(5'-oxo-pentanyl)-sn-glycero-3-phosphocholine (compound VI, prepared as described above), 0.50 gram (0.89 mmol), was dissolved in formic acid (15 ml) and hydrogen peroxide 30% (3.5 ml) was added. The reaction mixture was stirred overnight at room temperature. After addition of water (50 ml) the product was extracted with a mixture of 2:1 chloroform:methanol (2×50 ml). The organic phase was washed with aqueous 10% sodium bicarbonate (10 ml) and water (10 ml) and the solvent was removed under reduced pressure. The residue (0.4 gram) was dissolved in methanol (10 ml), aqueous 10% sodium hydroxide (4 ml) was then added and the reaction mixture was stirred at room temperature for 1 hour. 80% Phosphoric acid (2 ml) and potassium meta periodate (0.8 gram) were thereafter added and stirring was continued for over night. A mixture of 2:1 chloroform:methanol (50 ml) was then added and the organic phase was washed with aqueous 10% sodium bisulfite (10 ml) and water (10 ml), and the solvent was removed under vacuum. The residue (0.3 gram) was purified by chromatography over silica gel (10 grams) using a mixture of chloroform:methanol (60:40 to 40:60) as graduated eluent, to give 1-hexadecyl-2-(5',5'-dimethoxy-pentyloxy)-sn-glycero-3-phosphocholine (0.25 gram, 46% yield). NMR and mass spectrometry confirmed the chemical structure (Compound VIIIa, FIG. 10).

Synthesis of 1-Hexadecyl-2-(5',5'-diethoxypentyloxy)-sn-glycero-3-phosphocholine Crude 1-Hexadecyl-2-(5'-oxo-pentanyl)-sn-glycero-3-phosphocholine (compound VI, prepared as described above), 50 mg (0.088 mmol), was dissolved in ethanol (10 ml), under a nitrogen atmosphere. Triethyl orthoformate (0.053 ml, 0.0476 gram, 0.32 mmol) and 3 drops of conc. sulfuric acid were added and the reaction mixture was stirred overnight at room temperature. Dichloromethane (75 ml) was then added and the reaction mixture was transferred to a separatory funnel, washed successively with water (75 ml), aqueous 2.5% sodium bicarbonate solution (75 ml) and water (75 ml), and was dried over anhydrous sodium sulfate. After filtration, the solvent was removed under vacuum, to give 50 mg of crude 1-hexadecyl-2-(5',5'-diethoxypentyloxy)-sn-glycero-3-phosphocholine. The structure was confirmed by CMR and MS spectroscopy (Compound VIIIb, FIG. 10).

Synthesis of 1-Hexadecanoyl-2-(5'-oxo-valeroyl)-sn-3-glycerophosphocholine(POVPC)

A mixture of 1-hexadecanoyl-sn-3-glycerophosphocholine (compound I, FIG. 2) (3 grams), 5-hexenoic acid (1.2 ml), 1,3-dicyclohexylcarbodiimide (DCC, 4.05 grams) and N,N-dimethylaminopyridine (DMP, 1.6 grams) in dichloromethane (100 ml, freshly distilled from phosphorus pentoxide) was thoroughly stirred for 4 days at room temperature. The mixture was then chromatographed on silica gel 60 (40 grams) and the product, 1-hexadecanoyl-2-(5'-hexenoyl)-sn-3-glycerophosphocholine (2.8 grams, compound II, FIG. 2) was eluted with a mixture of 25:75 chloroform:methanol. The eluent was dissolved in 30% hydrogen peroxide:formic acid (4:15) and the solution was stirred overnight at room temperature. Water (50 ml) were added, the product was extracted with 2:1 chloroform:methanol (100 ml) and the organic phase was washed with water. The solvent was evaporated under reduced pressure, the residue was dissolved in methanol (15 ml) and 10% ammonia solution (5 ml) and the resulting solution was stirred at room temperature for 6 hours. The crude 1-hexadecanoyl-2-(5',6'-dihydroxy)-hexanoyl-sn-3-glycerophosphocholine (compound III, FIG. 2) (structure confirmed by NMR and mass spectrometry) was further reacted without purification. 80% phosphoric acid (3 ml) and sodium metaperiodate (1 gram) were added to the solution and the mixture was stirred at room temperature for overnight, and was thereafter extracted with a mixture of 2:1 chloroform:methanol. The product was purified by chromatography on silica gel 60 (20 grams), using a mixture of 25:75 chloroform:methanol as eluent. 850 mg of 1-hexadecanoyl-2-(5'-oxo-valeroyl)-sn-3-glycerophosphocholine (POVPC, compound IV, FIG. 2) were obtained, exhibiting chromatographic mobility of lecithin on TLC, and positive dinitrophenyl hydrazine reaction. The structure was assessed by NMR and mass spectrometry.

Alternatively: the ethylenic group was converted to an aldehyde by ozonization and catalytic hydrogenation with palladium calcium carbonate.

Example II

Immunization Against L-ALLE+D-ALLE Specifically Inhibits Atherogenesis in Genetically Disposed (Apo-E KO) Mice The present inventors have demonstrated that immunization with the stable, etherified synthetic LDL component ALLE can reduce the extent of atherosclerotic plaque formation in susceptible mice. 19 female 5-7 weeks old Apo E/C 57 mice were divided into 3 groups. In group A (n=6) the mice were immunized intraperitoneally, as described in Materials and Methods section above, with 150 µg/mouse L-ALLE+D-ALLE once every 2 weeks (0.3 ml/mouse) X4. In group B (n=6) the mice were immunized with tuberculin toxin Purified Protein Derivative (PPD) once every 2 weeks (0.3 ml/mouse). In group C (n=7) the mice received no immunization. Mice from all three groups were bled prior to immunization (Time 0), and one week after the second immunization for determination of anti-ox LDL antibodies, anti-ALLE antibodies and lipid profile. Atherosclerosis assessment was performed as described above, 4.5 weeks post $4^{th}$ immunization. The mice from all groups were weighed at 2 week intervals throughout the experiment. All mice were fed normal chow-diet containing 4.5% fat by weight (0.02% cholesterol) and water ad libitum.

TABLE I

Immunization of Apo-E KO mice with ALLE inhibits atherogenesis

| Groups | | 150 µg/Mouse L-ALLE + D-ALLE immunization N = 6 | PPD N = 5 | Control without immunization N = 7 | Statistics |
|---|---|---|---|---|---|
| Time 0 | Weight | 17.3 ± 0.5 | 17.3 ± 0.7 | 17.8 ± 0.4 | P = 0.780 |
| | Chol | 435 ± 47 | 436 ± 49 | 413 ± 44 | P = 0.919 |
| | TG | 118 ± 9 | 112 ± 10 | 120 ± 14 | P = 0.865 |

TABLE I-continued

Immunization of Apo-E KO mice with ALLE inhibits atherogenesis

| Groups | | 150 μg/Mouse L-ALLE + D-ALLE immunization N = 6 | PPD N = 5 | Control without immunization N = 7 | Statistics |
|---|---|---|---|---|---|
| End | Weight | 20.5 ± 0.5 | 21.6 ± 0.2 | 20.3 ± 0.5 | P = 0.123 |
| | Chol | 299 ± 18 | 294 ± 15 | 3044 ± 22 | P = 0.937 |
| | TG | 57 ± 3 | 53 ± 4 | 66 ± 4 | P = 0.075 |
| | Lesion size ($\mu m^2$) | 101000 ± 8276 | 179500 ± 13449 | 210833 ± 26714 | P = 0.005 |
| | TGF-β pmol/ml | 12032 ± 2308 | 13963 ± 944 | 12825 ± 2340 | P = 0.831 |

Note:
"Weight" is weight in grams;
"Chol" is plasma cholesterol and
"TG" is plasma triglycerides, expressed in mg/dL.

As can be seen in FIG. 3, the results depicted in Table I demonstrate the significant reduction in atheromatous lesions measured in the heart tissues of the ALLE immunized mice, compared to both PPD and unimmunized control mice. No significant effect is apparent on other parameters measured, such as weight gain, triglyceride or cholesterol plasma levels, or immune competence, as measured by the levels of the immunosuppressive cytokine TGF-β. Thus, immunization with the synthetic oxidized LDL component ALLE (a mixture of racemic forms D- and L-) confers significant (>50%) protection from atherosclerotic lesion formation in these genetically susceptible Apo-E KO mice. A significant but less dramatic reduction in plaquing was observed in mice immunized with PPD.

Example III

Figure 1:
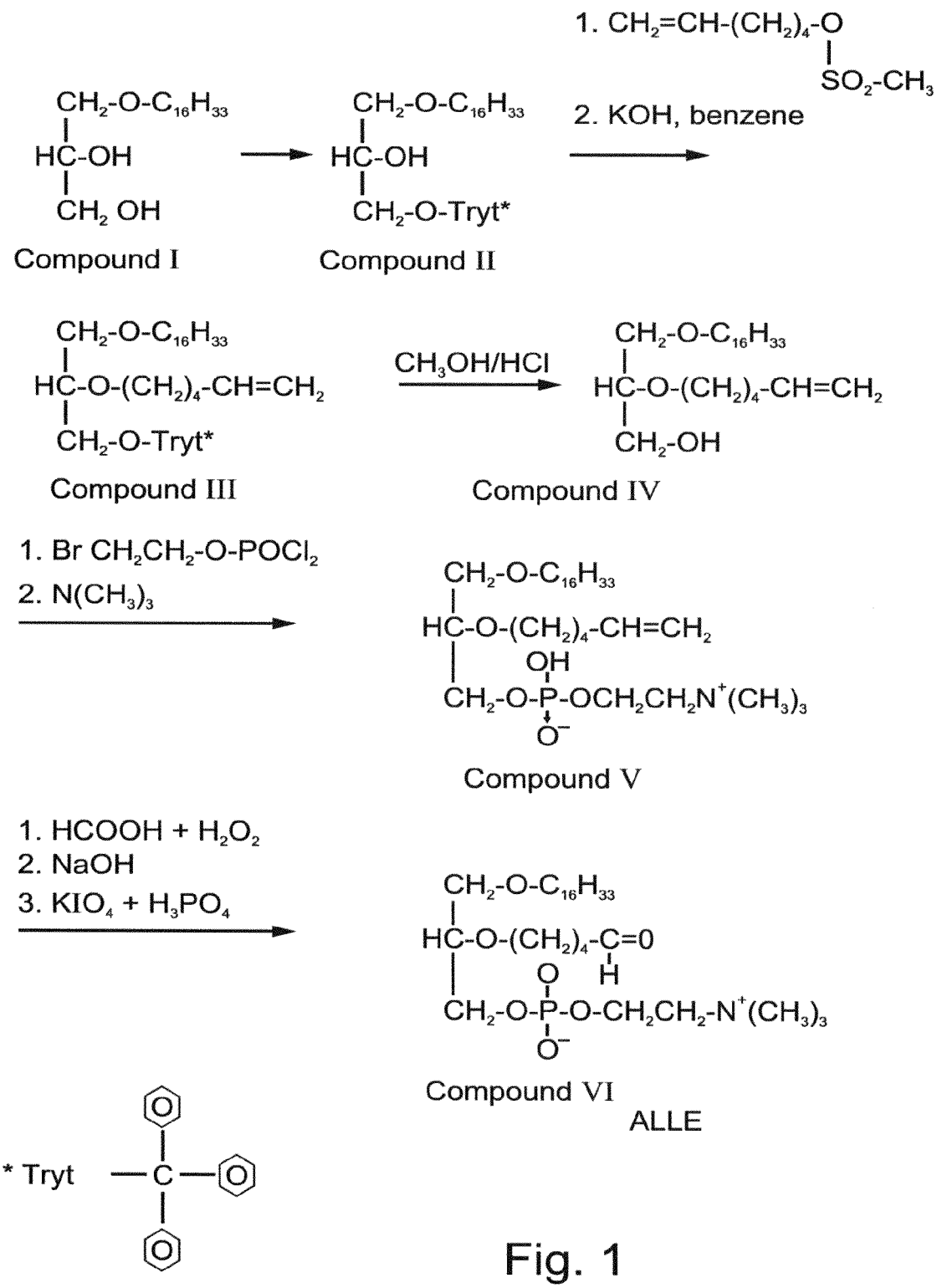

Inhibition of Atherogenesis in Genetically Predisposed (Apo-E KO) Mice by Oral Administration of L-ALLE and D-ALLE Intraperitoneal immunization with the ester analogs of plaque lesion components was effective in inhibiting atherogenesis in Apo-E KO mice (FIG. 1). Thus, the ability of oral administration of L- and D-ALLE to suppress atherogenesis was investigated. 34 male 8-10 week old Apo-E KO mice were divided into three groups. In group A (n=11), mice were orally administered by gavage of L-ALLE+D-ALLE suspended in PBS 5% ethanol (1 mg/mouse) for 5 days every other day. In group B (n=11) mice were fed with 10 μg/mouse L-ALLE+D-ALLE suspended in PBS 5% ethanol for 5 days every other day. (0.2 ml/mouse). Mice in group C (n=12) received PBS (containing the same volume of ethanol as in groups A+B). Mice were bled prior to feeding (Time 0) and at the conclusion of the experiment (End) for determination of lipid profile. Atherosclerosis was assessed in the aorta sinus, as described above, 8 weeks after the last feeding. Mice were weighed every 2 weeks during the experiment. All mice were fed normal chow-diet containing 4.5% fat by weight (0.02% cholesterol) and water ad libitum.

TABLE 2

Inhibition of atherogenesis in Apo-E KO out mice by oral administration of L-ALLE and D-ALLE

| Groups | | PBS N = 12 | 1 mg ALLE N = 11 | 10 μg ALLE N = 11 | Statistics |
|---|---|---|---|---|---|
| Time 0 | Weight | 20.7 ± 0.6 | 21.5 ± 0.8 | 21.1 ± 0.8 | P = 0.794 |
| | Chol | 373 ± 25 | 379 ± 23 | 378 ± 31 | P = 0.983 |
| | TG | 128 | 98 | 90 | P = 0.829 |
| End | Weight | 27.3 ± 0.4 | 27.4 ± 0.5 | 24.1 ± 0.8 | P < 0.001 |
| | Chol | 303 ± 17 | 249 ± 24 | 321 ± 15 | P = 0.031 |
| | TG | 81 ± 4 | 78 ± 8 | 93 ± 6 | P = 0.146 |
| | Lesion size ($\mu m^2$) | 176000 ± 13735 | 85278 ± 11633 | 103889 ± 14320 | P < 0.001 |
| | TGF-β pmol/ml | 14696 ± 1352 | 13388 ± 1489 | 18010 ± 1373 | P = 0.07 |

Note:
"Weight" is weight in grams;
"Chol" is serum cholesterol and
"TG" is serum triglycerides, expressed in mg/dL.

As can be seen from FIG. 4, the results depicted in Table 2 demonstrate a striking attenuation of atherosclerotic progression measured in the tissues of mice fed low doses (10 μg-1 mg/mouse) of ALLE, compared to unexposed control mice. No significant effect is apparent on other parameters measured, such as weight gain, triglyceride or cholesterol blood levels, or immune competence, as measured by the levels of the immunosuppressive cytokine TGF-β. Thus, oral administration of the synthetic oxidized LDL component ALLE provides for significant (>50%) protection from atherosclerosis in these genetically susceptible Apo-E KO mice, similar to the protection achieved with peritoneal immunization (see FIG. 1).

Example IV

Inhibition of Atherogenesis in Genetically Predisposed (Apo-E KO) Mice by Induction of Oral- and Nasal-Mediated Immunomodulation with L-ALLE Mechanisms of mucosal-mediated immunomodulation are active in the nasal mucosa as well as the gut. Thus, nasal exposure and oral exposure to L- and D-ALLE were compared for their effectiveness in suppressing atherogenesis in Apo-E KO mice. 34 male 7-10 weeks old Apo-E KO mice were divided into 3 groups. In group A (n=11) mice were orally administered with L-ALLE suspended in PBS 5% ethanol (1 mg/mouse/0.2 ml) for 5 days every other day. In group B (n=11) mice were nasally administered as described above in Materials and Methods with 10 μg/mouse/10 μL-ALLE suspended in PBS every other day for 3 days. Mice in group C (n=12) received PBS administered orally and nasally (containing the same volume of ethanol as in groups A+B). Mice were bled prior to feeding (Time 0) and at the conclusion of the experiment (End) for determination of lipid profile. Atherosclerosis was assessed in the aorta sinus as described above, 8 weeks after the last feeding. Mice were weighed every 2 weeks during the experiment. All mice were fed normal chow-diet containing 4.5% fat by weight (0.02% cholesterol) and water ad libitum.

As can be seen from FIG. 5, the results depicted in Table 3 demonstrate effective inhibition of atherogenesis measured in the tissues of mice receiving nasal exposure to low doses (10 μg/mouse) of ALLE, compared to unexposed control mice. Nasal administration, like oral administration, had no significant effect on other parameters measured, such as weight gain, triglyceride or cholesterol plasma levels. Thus, the synthetic oxidized LDL component ALLE provides for significant (approximately 50%) protection from atherogenesis in these genetically susceptible Apo-E KO mice, by both oral and nasal administrations.

Example V

Suppression of Specific Anti-oxLDL Immune Reactivity in Genetically Predisposed (Apo-E KO) Mice by Oral Administration of L-ALLE or POVPC Immunomodulation induced by mucosal exposure to oxidized analogs of LDL may be mediated by suppression of specific immune responses to the plaque-related antigens. POVPC (1-Hexadecanoyl-2-(5'-oxo-valeroyl)-sn-glycerophosphocholine) is a non-ether oxidized LDL analog, which, unlike ALLE is susceptible to breakdown in the liver and gut. Lymphocyte proliferation in response to oral exposure to both POVPC and the more stable analog ALLE was measured in Apo-E KO mice. 8 male, 6 week old Apo-E KO mice were divided into 3 groups. In group A (n=2) mice were fed with 1 mg/mouse L-ALLE suspended in 0.2 ml PBS, administered by gavage, as described above, every other day for 5 days. In group B (n=3) mice were fed with 1 mg/mouse POVPC suspended in 0.2 ml PBS, administered per os as described above, every other day for 5 days. The mice in group C (n=3, control) were fed with 200 μl PBS every other day for 5 days. Immune reactivity was stimulated by immunization with Human oxidized LDL as described above in the Materials and Methods section, one day after the last feeding. One week after the immunization lymph nodes were collected for assay of proliferation. All mice were fed normal chow-diet containing 4.5% fat by weight (0.02% cholesterol) and water ad libitum.

TABLE 3

The effect of oral and nasal administration of L-ALLE on metabolic parameters and atherogenesis in Apo-E KO mice

| Groups | | 1 mg ALLE Oral (N = 11) | 10 μg ALLE Nasal (N = 11) | PBS Oral/nasal (N = 12) | Statistics |
|---|---|---|---|---|---|
| Time 0 | Weight | 21.1 ± 0.8 | 21.1 ± 0.7 | 22.1 ± 0.9 | P = 0.624 |
| | Chol | 362 ± 27 | 353 ± 31 | 351 ± 27 | P = 0.952 |
| | TG | 144 | 143 | 138 | P = 0.977 |
| End | Weight | 23.3 ± 1.1 | 24.2 ± 0.2 | 24.0 ± 0.5 | P = 0.558 |
| | Chol | 418 ± 43 | 328 ± 18 | 343 ± 25 | P = 0.084 |
| | TG | 82 ± 7 | 74 ± 6 | 79 ± 5 | P = 0.630 |
| | Lesion size (μm$^2$) | 76944 ± 17072 | 82708 ± 10986 | 135455 ± 12472 | P = 0.007 |

Note:
"Weight" is weight in grams;
"Chol" is plasma cholesterol and
"TG" is plasma triglycerides, expressed in mg/dL.

TABLE 4

Oral pretreatment with synthetic oxidized LDL (ALLE and POVPC) suppresses immune response to Human ox-LDL in Apo-E KO mice Stimulation Index (SI)

| PBS | POVPC | L-ALLE | statistics |
|---|---|---|---|
| 33.1 ± 6.1 | 10.6 ± 2.3 | 7.3 ± 2.3 | P < 0.01 |
| N = 3 | N = 3 | N = 2 | |
|  | −68% | −78% | |

As can be seen from FIG. 6, the results depicted in Table 4 demonstrate significant suppression of immune reactivity to Human oxidized-LDL antigen, measured by inhibition of proliferation in the lymph nodes of Apo-E KO mice. Lymphocytes from mice receiving oral exposure to atherogenesis-inhibiting doses (1 mg/mouse) of ALLE or POVPC showed a reduced stimulation index following immunization with ox-LDL, as compared to control (PBS) mice. Since induction of oral-mediated, like nasal-mediated, immunomodulation had no significant effect on other parameters measured, such as weight gain, triglyceride or cholesterol plasma levels, or immune competence (see Tables 1, 2 and 3), these results indicate a specific suppression of anti-ox-LDL immune reactivity. Thus, oral administration of the synthetic oxidized LDL component L-ALLE is an effective method of attenuating the cellular immune response to immunogenic and atherogenic plaque components in these genetically susceptible Apo-E KO mice. FIG. 4 also demonstrates a similar, if less effective inhibition of proliferation with oral administration of the less stable synthetic oxidized LDL component POVPC.

Example VI

Inhibition of Atherogenesis in Genetically Predisposed (Apo-E KO) Mice by Oral Administration of D- and L-Isomers of ALLE, and POVPC Since feeding of ALLE and POVPC was shown to inhibit early atherogenesis and immune reactivity to plaque-related Human LDL antigen, the ability of both D- and L-isomers of the ether LDL analog, and the non-ether analog POVPC to suppress the progression of atherogenesis in older mice was compared. Their effect on the triglyceride and cholesterol fractions of VLDL was also monitored by FPLC. 57 male, 24.5 week old Apo-E KO mice were divided into 5 groups. In group A (n=11) mice were fed with 1 mg/mouse L-ALLE suspended in 0.2 ml PBS, administered by gavage, as described above, every other day for 5 days. In group B (n=9) mice were fed with 1 mg/mouse D-ALLE suspended in 0.2 ml PBS, administered per os, as described above, every other day for 5 days. In group C (n=10) mice were fed with 1 mg/mouse POVPC suspended in 0.2 ml PBS, administered by gavage, as described above, every other day for 5 days. Control group D (n=10) received oral administration of PBS (containing the same volume of ethanol as in groups A, B, C). Base line group was sacrificed on time=0. Oral administration of the tested antigens took place every 4 weeks (5 oral feedings; every other day) starting at 24.5 weeks age, during 12 weeks (3 sets of feedings).

Mice were bled prior to feeding (Time 0), after the $2^{nd}$ set of feeding and at the conclusion of the experiment (End) for determination of lipid profile, lipid fractionation and plasma collection. Atherosclerosis was assessed as described above in the aorta sinus and aorta. Spleens were collected for proliferation assay 12 weeks after the first feeding. Weight was recorded every 2 weeks throughout the experiment. All mice were fed normal chow-diet containing 4.5% fat by weight (0.02% cholesterol) and water ad libitum.

TABLE 5

Inhibition of atherogenesis in Apo-E KO mice by oral administration of L-ALLE, D-ALLE and POVPC

| Time point | Parameter tested | PBS (n = 10) | 1 mg L-ALLE (n = 11) | 1 mg D-ALLE (n = 9) | 1 mg POVPC (n = 10) | Base line (t = 0) (n = 8) | statistics |
|---|---|---|---|---|---|---|---|
| 0 | Weight | 28.1 ± 0.5 | 29 ± 0.6 | 29.8 ± 0.7 | 29.6 ± 0.7 | 29.8 ± 1.1 | P = 0.445 |
|  | Cholesterol | 413 ± 27 | 413 ± 23 | 409 ± 28 | 401 ± 21 | 393 ± 16 | P = 0.976 |
|  | Triglyceride | 67 ± 5 | 63 ± 8 | 63 ± 4 | 67 ± 7 | 71 ± 8 | P = 0.946 |
| End | Weight | 28.5 ± 0.6 | 29.7 ± 0.5 | 30.4 ± 0.8 | 29.9 ± 0.5 | — | P = 0.177 |
|  | Cholesterol | 365 ± 15 | 391 ± 18 | 394 ± 15 | 358 ± 28 | — | P = 0.481 |
|  | Triglyceride | 84 ± 4 | 83 ± 4 | 94 ± 4 | 85 ± 3 | — | P = 0.207 |
|  | Sinus Lesion µm² | 369688 ± 32570 | 233056 ± 12746 | 245938 ± 20474 | 245750 ± 20423 | 225,714 ± 5,869 | P < 0.001 |
|  | Aorta lesion (% from total area) | 4.5 | 5.4 | 4.5 | 8.3 | 1.4 | P = 0.002 |

Note:
"Weight" is weight in grams;
"Cholesterol" is plasma cholesterol and
"Triglyceride" is plasma triglycerides, expressed in mg/dL.

As can be seen from FIG. 7, the results depicted in Table 5 demonstrate effective inhibition of late stage atherogenesis measured in the tissues of older mice following protracted oral exposure to a 1 mg/mouse dose of the D- and L-isomers of ALLE, and POVPC compared to PBS-fed control mice. Oral administration of these compounds had no significant effect on other parameters measured, such as weight gain, total triglyceride or cholesterol plasma levels. Thus, the synthetic oxidized LDL components D-, L-ALLE and POVPC each individually exert anti-atherogenic activity, conferring nearly complete protection from atheromatous progression (as compared with lesion scores at 24.5 weeks) in these genetically susceptible Apo-E KO mice. Surprisingly, it was observed that the inhibition of atherogenesis by these oxidized LDL analogs is accompanied by a significant reduction in VLDL cholesterol and triglycerides, as measured by FPLC (FIGS. 8 and 9).

Example VII

Inhibition of Atherogenesis in Genetically Predisposed (Apo-E KO) Mice by Oral Administration of CI-201

The ability of a stable form of an etherified phospholipid, the acid derivative of ALLE, CI-201, to suppress atherogenesis was investigated. Male 12 weeks old Apo-E KO mice were divided into two groups. In group A (n=14) mice were orally administered by gavage of CI-201 (0.025 mg/dose) suspended in PBS for 8 weeks every day (5 times a week). Mice in group B (n=15) received PBS (control). Atherosclerosis was assessed as described above. All mice were fed normal chow-diet containing 4.5% fat by weight (0.02% cholesterol) and water ad libitum.

As can be seen from FIG. 11, the results demonstrate a striking attenuation of atherosclerotic progression measured in the tissues of mice fed low doses of CI-201, as compared with unexposed control mice (PBS). Aortic sinus lesion in the CI-201 treated group was $125,192 \pm 19,824$ $\mu m^2$ and in the control group (PBS treated) was $185,400 \pm 20,947$ $\mu m^2$, demonstrating a decrease of 33% (P=0.051) of the aortic sinus lesion by oral administration of CI-201 in low dose. IL-10 expression (determined by RT-PCR) in the aorta was higher by 40% in the CI-201 treated group, as compared with the control group. The elevated expression levels of IL-10 in the target organ, the aorta, support an anti-inflammatory effect induced by CI-201 oral administration. Thus, the stable synthetic oxidized LDL-201, exerts both oral-mediated immunomodulation and anti-inflammatory effect.

Example VIII

Cytokine Expression in the Aorta of Apo-E KO Mice Treated with Oxidized Phospholipids (ALLE, CI-201, Et-Acetal, Me-Acetal & oxLDL)

The effect of ALLE, CI-201, its corresponding acetal derivatives Et-acetal and Me-acetal (Compounds IIa and IIb, FIG. 10) and oxLDL on cytokine expression in the target organ—the aorta—was evaluated using RT-PCR as described hereinabove. Apo-E KO mice were orally administered with 1 mg/mouse ALLE, 1 mg/mouse CI-201, 1 mg/mouse Et-acetal, 1 mg/mouse Me-acetal, 0.1 mg/mouse oxLDL or 0.2 ml/mouse PBS. Oral administrations took place 5 times every other day. The expression of the anti-inflammatory cytokine IL-10 and the pro-inflammatory cytokine IFN-γ and IL-12 were determined 8 weeks after final oral administration.

As can be seen in FIGS. 12a and 12b, mice treated with ALLE, CI-201, Et-acetal, Me-acetal and oxLDL showed elevated levels of IL-10 expression as compared with the control PBS-treated group. As can be seen in FIGS. 12c and 12d, an opposite effect was shown in the expression level of IFN-γ and IL-12. Reduced expression levels of IFN-γ was detectable in mice treated with ALLE, CI-201, Me-acetal and oxLDL and reduced levels of IL-12 was detectable in mice treated with ALLE, CI-201, Et-acetal and oxLDL.

Example IX

Inhibition of Atherogenesis in LDL-RD Mice by Induction of Oral-Mediated Immunomodulation with oxLDL In order to show that the synthetic oxidized phospholipids described above induce a similar effect as human oxidized LDL, a model for evaluating the effect of oxLDL on atherosclerosis progression in mice was designed.

LDL-RD Mice, 8-12 weeks old, were stratified by age, weight and lipid profile (Cholesterol and Triglyceride) to different groups. Each group was treated with oxLDL in escalating doses (10, 100 or 1,000 μg/dose dissolved in PBS in a total volume of 0.2 ml PBS), albumin (100 μg/dose dissolved in PBS in a total volume of 0.2 ml PBS) or PBS (0.2 ml), 5 times every other day. One day following the last oral administration, mice were challenged with an atherogenic diet ("Western diet"), ad libitum, and kept in 12 hours dark/light cycle, for five weeks.

Mice were sacrificed 6.5 weeks after the first oral administration and evaluated for the extent of atheromatous plaque area within the aortic sinus, as described hereinabove.

The effect of oxLDL treatment on metabolic parameters is delineated in Table 6 below. As is shown in Table 6, while oxLDL did not affect body weight or cholesterol levels, OxLDL in a dose of 100 μg/dose significantly (P<0.05) reduced the triglyceride levels as compared with the PBS and albumin control groups.

TABLE 6

Effect of OxLDL treatment on Metabolic Parameters in LDL-RD mice

| Time point | Parameter | Group A OxLDL 1,000 μg/dose | Group B OxLDL 100 μg/dose | Group C OxLDL 10 μg/dose | Group D Human Serum albumin | Group E PBS | Statistics |
|---|---|---|---|---|---|---|---|
| T = 0 | Weight (g) | 28.1 ± 0.6 | 27.3 ± 0.6 | 26.9 ± 0.5 | 28.5 ± 0.6 | 27.9 ± 0.5 | N.S* |
|  | Cholesterol (mg/Dl) | 161 ± 10 | 160 ± 8 | 156 ± 9 | 163 ± 10 | 162 ± 7 | N.S* |
|  | Triglyceride (mg/Dl) | 154 ± 12 | 145 ± 11 | 152 ± 10 | 140 ± 14 | 155 ± 12 | N.S* |
| END | Weight(g) | 29.0 ± 0.7 | 26.8 ± 0.4 | 27.6 ± 0.7 | 29.4 ± 1.8 | 29.1 ± 0.6 | N.S* |
|  | Cholesterol (mg/Dl) | 1,541 ± 175 | 1,372 ± 122 | 1,458 ± 101 | 1,589 ± 76 | 1,554 ± 121 | N.S* |
|  | Triglyceride (mg/Dl) | 344 | 120 | 250 | 303 | 306 | P < 0.001** |

*N.S: Not significant
**Kruskal Wallis One Way Analysis of Variance on Ranks test was performed, data displayed as median values.
Note:
"Weight" is weight in grams;
"Cholesterol" is plasma cholesterol and
"Triglyceride" is plasma triglycerides, expressed in mg/dL.

The attenuation of atherogenesis by oral administration of OxLDL is demonstrated in FIG. 13 and in Table 7 below. As is shown in FIG. 13, treatment with both 100 μg/dose and 1,000 μg/dose oxLDL significantly decreased (P<0.001) the lesion area in the aortic sinus by 45% as compared with the control groups (PBS treated or human serum albumin (HAS) treated).

TABLE 7 effect of OxLDL treatment on atherosclerosis area in the aortic sinus

| Parameter | Group A OxLDL 1,000 μg/ dose | Group B OxLDL 100 μg/ dose | Group C OxLDL 10 μg/ dose | Group D Human Serum albumin | Group E PBS | Statistics |
|---|---|---|---|---|---|---|
| Aortic Sinus Lesion ($\mu m^2$) | 37,750 ± 4,890 | 38,304 ± 4,443 | 45,568 ± 3,309 | 77,604 ± 5,039 | 69,712 ± 6,797 | P < 0.001 |

Example X
Inhibition of Atherogenesis in Genetically Predisposed (Apo-E KO) Mice by Oral Administration of CI-201

26-28 weeks old Apo-E KO mice (APO-E−/−<tm1Unc> [C57B/6J]) were used as a prevention of progression model. Mice were stratified by age, weight and lipid profile (cholesterol and triglyceride) to different groups. One group was sacrificed at the beginning of the experiment and served as the "base line" group. Each of the other groups was treated with CI-201 in escalating doses (0.1, 1 or 10 μg/dose dissolved in PBS, 0.05% ethanol, in a total volume of 0.2 ml PBS). The control group received PBS (0.05% ethanol, 0.2 ml).

Mice were treated with CI-201 or PBS at three sets at the beginning of each month, each set consisted of 5 oral administrations every other day. All mice were fed normal chow-diet containing 4.5% fat by weight (0.02% cholesterol) and water ad libitum and were kept in a 12 hours dark/light cycle.

After 12 weeks mice were sacrificed and evaluated for the extent of atheromatous plaque area within the aortic sinus, as described hereinabove.

The effect of CI-201 treatment on metabolic parameters is presented in Table 8 below. The results show that CI-201 does not affect both the body weight and the lipid profile of the tested mice.

TABLE 8

Effect of CI-201 treatment on Metabolic Parameters in Apo-E KO mice

| Time point | Parameter | Group A CI-201 10 μg/dose | Group B CI-201 1 μg/dose | Group C CI-201 0.1 μg/dose | Group D PBS | Group E Base- Line | Statistics |
|---|---|---|---|---|---|---|---|
| T = 0 | Weight (g) | 26.6 ± 0.5 | 26.4 ± 0.4 | 26.4 ± 0.4 | 26.5 ± 0.4 | 26.7 ± 0.5 | N.S* |
|  | Cholesterol (mg/Dl) | 321 ± 23 | 323 ± 20 | 313 ± 14 | 316 ± 12 | 315 ± 20 | N.S* |
|  | Triglyceride (mg/Dl) | 88 ± 4 | 87 ± 4 | 87 ± 6 | 80 ± 4 | 84 ± 8 | N.S* |
| END | Weight(g) | 29.6 ± 0.5 | 29.0 ± 0.4 | 28.8 ± 0.7 | 28.1 ± 1.8 | — | N.S* |
|  | Cholesterol (mg/Dl) | 344 ± 25 | 382 ± 24 | 406 ± 39 | 354 ± 24 | — | N.S* |
|  | Triglyceride (mg/Dl) | 76 ± 4 | 96 ± 8 | 107 ± 13 | 91 ± 7 | — | N.S* |

*N.S: Not significant
Note:
"Weight" is weight in grams;
"Cholesterol" is plasma cholesterol and
"Triglyceride" is plasma triglycerides, expressed in mg/dL.

The attenuation of atherogenesis by oral administration of CI-201 is demonstrated in FIGS. 14a-b and in Table 9 below.

TABLE 9

CI-201 effect on atherosclerosis area in the aortic sinus

| Parameter | Group A CI-201 10 µg/ dose | Group B CI-201 1 µg/ dose | Group C CI-201 0.1 µg/ dose | Group D PBS | Group E Base-Line | Statistics |
|---|---|---|---|---|---|---|
| Aortic Sinus Lesion ($\mu m^2$) | 272,483 ± 20,505 | 295,729 ± 20,909 | 228,000 ± 25,772 | 328,491 ± 21,920 | 218,602 ± 29,248 | $P < 0.05$ |

The results presented, in Table 9 show that CI-201 treatment completely inhibited disease progression, such that the lesion areas in the aortic sinus of mice treated with different doses of CI-201 were similar to that of the base line group.

Contrary to that, a 50% highly significant (p<0.01) increase in atherosclerotic lesion in the aortic sinus was observed in the PBS treated mice as compared with the base line group (328,491±21,920 $\mu m^2$ in the PBS group versus 218,602±29,248 $\mu m^2$ in the base line group).

As is demonstrated in FIG. 14a, all doses of CI-201 inhibited the disease progression, while the most effective dose was the minimal dose of 0.1 µg/dose. As is demonstrated in FIG. 14b, the group treated with 0.1 µg/dose CI-201 exhibit a 92% significant (P<0.05) decrease in atherosclerotic lesion in the aortic sinus as compared with the PBS treated group (328,491±21,920 $\mu m^2$ in the PBS group versus 228,000±25,772 $\mu m^2$ in the CI-201 treated group).

Example XI

Elevation of Inflammation Markers in the Serum of Apo-E KO Mice Treated with CI-201

In view of the dramatic inhibition of atherosclerosis progression by oral administration of CI-201, which, as described hereinabove, is not attributed to alteration of body weight or lipid profile induced thereby, the effect of oral administration of CI-201 on the level of inflammation markers in the serum was evaluated, in order to investigate its mechanism of action.

As is shown in experimental and clinical studies, IL-10 is a major protective cytokine in plaque growth and stability. For example, Caligiuri et al. (Interleukin-10 deficiency increases atherosclerosis, thrombosis, and low-density lipoproteins in apolipoprotein E knockout mice. *Mol. Med.* 2003; 9(1-2):10-17) recently reported that lesion size was dramatically increased in double KO mice for Apo-E and IL-10, as compared with controls, and the proteolitic and procoagulant activity were elevated, showing that IL-10 may reduce atherosclerosis and improve the stability of plaques.

Another marker of acute inflammatory state is Serum Amyloide A (SAA), a high sensitive inflammatory marker which can be increased up to 1,000 fold during inflammation. SAA as a CRP (C Reactive Protein) is synthesized by the liver in response to IL-1, IL-6 and TNF (Balke and Ridker, Novel clinical markers of vascular wall inflammation, *Circ Res.* 2001; 89:763-771.). SAA has been found to be is expressed by several cell types in atherosclerotic lesion (Meek et al. Expression of apolipoprotein serum amyloid A mRNA in human atherosclerotic lesions and cultured vascular cells: implications for serum amyloid A function. *Proc Natl Acad Sci USA* 1994; 91:3186-3190; Uhlar and Whitehead. Serum amyloid A, the major vertebrate acute-phase reactant. *Eur J Biochem.* 1999; 265:501-523).

Initiation of the inflammatory cascade occurs primarily through activated blood monocytes and tissue macrophages at the site of the inflammatory stimulus. Upon activation macrophages release a range of primary inflammatory mediators, the most important of which are members of the IL-1 and TNF cytokine families, which trigger the release of a range of secondary cytokines and chemokines (IL-6, IL-8 and MCP). The chemotactic activities of these molecules draw leukocytes to the inflammatory site, where they in turn release further pro-inflammatory cytokines.

Thus, Apo-E KO mice were orally administered with 0.1 µg/mouse CI-201 or 0.2 ml/mouse PBS, 5 times every other day. Mice serum was collected before treatment (day 0), at the end of the treatment (two weeks) and two weeks thereafter (4 weeks) and the level of the inflammation markers IL-10 and Serum Amyloide A (SAA) were evaluated.

The obtained data are presented in FIG. 15a (for IL-10 levels) and FIG. 15b (for SAA levels).

As can be seen in FIG. 15a, at the end of the treatment (2 weeks), a substantial increase in IL-10 serum level was observed, while 2 weeks thereafter (4 weeks) a decay has been noticed. In the control, PBS-treated group, no change in IL-10 serum levels was noticed throughout the experiment.

As can be seen in FIG. 15b, while SAA serum levels dramatically increased in the control group, no alterations in SAA serum levels in the CI-201 treated group were observed.

These results clearly indicate that by elevating IL-10 levels in the serum, CI-201 induce an anti-inflammatory response that may shut down a pro-inflammatory response, demonstrated by elevated levels of SAA. Systemic inflammation manifested by high SAA may promote atherosclerotic plaque destabilization in addition to exerting a possible direct effect on atherogenesis. These results further suggest a direct effect of CI-201 on inflammatory processes.

Example XII

Cytokine Expression in Various Organs of Apo-E KO Mice Treated with CI-201

The effects of CI-201 treatment on cytokine expression in the targeted organ—the aorta, as well as in the spleen, liver, kidneys and small intestine were evaluated using RT-PCR as described hereinabove. Apo-E KO mice were orally administered with 1 mg/dose CI-201 or with 0.2 ml/mouse PBS, 5 times every other day. The expression of the anti-inflammatory cytokine IL-10 and the pro-inflammatory cytokine IFN-γ were determined 8 weeks after final oral administration. The data obtained are presented in FIGS. 16a-b and FIG. 17.

As can be seen in FIGS. 16a and 16b, mice treated with CI-201 showed elevated levels of the anti-inflammatory cytokine IL-10 as compared with the control PBS-treated group, while an opposite effect, namely, reduced expression level, was shown in the expression level of the pro-inflammatory cytokine IFN-γ in the CI-201 treated group.

The increase in the anti-inflammatory response, as demonstrated by elevated levels of IL-10, accompanied with decreased pro-inflammatory response, as demonstrated by decreased levels of IFN-γ, further emphasize the immunomodulation induced by CI-201, which is effected by switching from Th1 towards Th2 response within the aorta, as well as the anti-inflammatory effect thereof.

While in the targeted organ, the aorta, CI-201 increases the anti-inflammatory response, such an effect was not observed in other organs. As can be seen in FIG. 17, no differences were observed in cytokine expression in the spleen and in the small intestine between the CI-201 treated group and the control, PBS treated, group. It is suggested that the Peyers patches located therein encountered the orally-administered antigen. No change in cytokine expression was observed in the liver and in kidney as well (data not shown).

The results above suggest that the oxidized phospholipids analogs of the present invention inhibit atherosclerosis via a pathway that affects both the immune system and inflammation. However, it is possible that other mechanisms are also involved in the most potent inhibitory effect thereof.

Example XIII

Inhibition of Rheumatoid Arthritis in Adjuvant Arthritis-Induced Rats by Oral Administration of CI-201

Rheumatoid arthritis (RA) is a severe autoimmune disease involving chronic joint inflammation and destruction. Adjuvant-induced arthritis (AIA) is the first experimental arthritis model (Pearson. Development of arthritis, periarthritis and periostitis in rats given adjuvant. *Proc Soc Exp Biol Med* 1956; 91:95-101; Pearson and Wood. Studies of polyarthritis and other lesions induced in rats by injection of mycobacterial adjuvant. I. general clinical and pathologic characteristics and some modifying factors. *Arthritis Rheum* 1959; 2:440-459).

The morphologic character of early AIA lesions is based on cell-mediated immunity (CMI). Lymphocytes infiltration is followed by edema, fibrin deposition, and necrosis, accompanied by proliferation of synoviocytes and fibroblasts and activation of osteoblasts and osteoclasts. The inflammatory infiltrate in the joint lesions of AIA contain T cells activated by specific antigens. Th1 cytokines, such as IL-17, IFN-γ, and TNF-α, are expressed in early AIA together with cytokines characteristics of macrophage activation. In a later phase of the disease, levels of IL-4, IL-6 and JE (murine homologe of monocyte chemoattractant protein 1) and TGF-β are elevated. There is local release of proteolytic enzymes and/or free radicals of oxygen, which results in a progressive breakdown of collagen type II and IX, matrix damage, and in time, degradation of bone (Van Eden and Waksman. Immune regulation in adjuvant-induced arthritis. Possible implications for innovative therapeutic strategies in arthritis. *Arthritis Rheum* 2003; 48(7):1788-1796).

Several attempts at immunotherapy of human autoimmune diseases such as rheumatoid arthritis (RA), type I diabetes, and multiple sclerosis, based either on modulation of individual immune pathways involved in inflammation or on tolerization to various antigens, have shown that this approach may be viable (Bielekova et al. Encephalitogenic potential of the myelin basic protein peptide (amino acids 83-99) in multiple sclerosis: Results of a phase II clinical trial with an altered peptide ligand. *Nat Med.* 2000; 6:1167-1175; Kappos et al. Induction of a non-encephalitogenic type 2 T helper-cell autoimmune response in multiple sclerosis after administration of an altered peptide ligand in a placebo-controlled, randomized phase II trial. *Nat. Med.* 2000; 6:1176-1182).

In many patients, the outcome of Rheumatoid Arthritis is complicated by cardiovascular disease, the latter being the main cause of the increased mortality in this disorder. Autoantibodies against cardiolipin (CL) and oxidatively modified low density lipoproteins (copper oxidized LDL), including malondialdehyde modified LDL (MDA-LDL), have been suggested to have a predictive value for cardiovascular disease. It has been demonstrated that there are increased levels of autoantibodies against copper-oxidized low density lipoprotein, malondialdehyde-modified low density lipoproteins and cardiolipin in patients with rheumatoid arthritis (Cvetkovic et al. Increased levels of autoantibodies against copper-oxidized low density lipoprotein, malondialdehyde-modified low density lipoprotein and cardiolipin in patients with rheumatoid arthritis. *Rheumatology.* 2002; 41:988-995). Moreover there are evidences for oxidized low density lipoprotein in synovial fluid from rheumatoid arthritis patients (Dai et al. Evidence for oxidized low density lipoprotein in synovial fluid from rheumatoid arthritis patients. *Free Radic Res.* 2000; 32(6):479-486).

Since CI-201 was found to be effective in both induction of immunomodulation to Ox LDL and increasing an anti-inflammatory response, its effect on arthritis development was tested.

Nine weeks old male Lewis rats were orally administered with different doses of CI-201 (4 mg/kg or 0.4 mg/kg) or with PBS, 5 times every other day. Adjuvant arthritis was then induced by intradermal injection of 0.1 ml of tuberculosis suspension. Intensity of arthritis was monitored by measuring paw swelling while mobility of the animals was monitored as well. The study design is presented in FIG. 18. The results are presented in FIG. 19.

As can be seen in FIG. 19, pre-treatment with the higher dose (4.0 mg/kg) of CI-201 resulted in a significant decrease in rats paw swelling, as compared with the control, PBS-pretreated rats.

While the PBS treated rats were barely moving, using only their back legs, the mobility of rats pre-treated with the higher dose of CI-201 was close to that of normal rats.

In order to evaluate the effect of a continuous treatment with CI-201 on AIA-induced Lewis rats, following the AIA-induction, 9 weeks old male Lewis rats were fed, 5 times every other day, before induction of AIA by intradermal injection of 0.1 ml of tuberculosis suspension and were thereafter continuously fed, three times a week, for about 30 days. The study design is presented in FIG. 20. The results are presented in FIG. 21-23.

As can be seen in FIGS. 21-23 CI-201, a continuous treatment with high dose of CI-201 substantially attenuated arthritis development in all the tested parameters.

These results clearly indicate that the anti-inflammatory properties of CI-201 can further influence a classic inflammatory disease, RA, in addition to its effect on atherosclerosis.

CD4+ T-helper cells and macrophages infiltrate the synovial membrane (SM) in chronic, destructive rheumatoid arthritis and probably play a central role in promoting and maintaining the disease process. CD4+ T cells can differentiate into Th1 subpopulation, characterized by predominant production of IFN-γ. Predominance of pro-inflammatory Th1 type cells has been postulated in RA (Schmidt-Weber et al. Cytokine gene activation in synovial membrane, regional lymph nodes, and spleen during the course of rat adjuvant arthritis. *Cell. Immunol.* 1999; 195:53-65.). Macrophages are also highly activated in the inflammatory process in RA, both locally and systemically.

The resemblances in the inflammatory response involved both in atherosclerosis and arthritis support the suggestion that CI-201 induces an anti-inflammatory response in AIA similarly to that demonstrated above in atherosclerosis.

It can therefore be postulated that CI-201 treatment induce IL-10 elevation in AIA model and IL-10 can suppress pro-inflammatory cytokine, thus reducing the disease outcome, as was demonstrated by decreased paw swelling and better mobility. These results therefore implicate that the oxidized phospholipids analogs of the present invention can serve as a new family of therapeutic drug for treating Rheumatoid Arthritis, as well as other autoimmune and/or inflammatory diseases.

Example XIV

Oral Administration of the Pre-Oxidized Compound V to Genetically Predisposed (Apo-E KO) Mice The Effect of an Oxidized Group on Atherogenesis Inhibition The effect of the oxidized group in ALLE and CI-201 was tested by comparing the effect of oral administration of ALLE and CI-201 on early atherogenesis and progression of advanced atherosclerotic plaques, shown above, with the effect of the pre-oxidized derivative thereof. Compound V (1-Hexadecyl-2-(5'-hexenyl)-sn-glycero-3-phosphocholine, Example I).

25 female, 8-10 week old Apo-E KO mice were divided into 4 groups. Each group was fed with 5 mg/mouse Compound V suspended in 0.2 ml PBS (Group A, n=6), 1 mg/mouse Compound V" suspended in 0.2 ml PBS (Group B, n=6), 0.2 mg/mouse Compound V suspended in 0.2 ml PBS (Group C, n=6), and PBS (Group D, control, n=7), every other day for 5 days. Eight weeks after the last oral administration mice were sacrificed. Mice were bled prior to feeding (Time 0) and at the conclusion of the experiment (End) for determination of lipid profile. Atherosclerosis was assessed in the heart, as described hereinabove. All mice were fed normal chow-diet containing 4.5% fat by weight (0.02% cholesterol) and water ad libitum.

The effect of Compound V treatment on metabolic parameters and on atherogenesis is delineated in Table 10 below. The effect of Compound V on atherogenesis is further presented in FIG. 24.

TABLE 10

The effect of the pre-oxidized derivative Compound V on metabolic parameters and atherosclerosis area in the aortic sinus in ApoE KO mice

| Time point | Parameter tested | PBS (n = 7) | 5 mg Comp. V (n = 6) | 1 mg Comp. V (n = 6) | 0.2 mg Comp. V (n = 6) | Statistics (p value) |
|---|---|---|---|---|---|---|
| 0 | Weight | 18.4 ± 0.4 | 18.0 ± 0.3 | 18.3 ± 0.3 | 18.5 ± 0.3 | 0.826 |
|   | Cholesterol | 197 ± 19 | 210 ± 18 | 198 ± 23 | 214 ± 21 | 0.902 |
|   | Triglyceride | 53 ± 10 | 52 ± 4 | 52 ± 5 | 50 ± 7 | 0.993 |
| End | Weight | 20.7 ± 0.4 | 19.8 ± 0.3 | 19.8 ± 0.2 | 20.1 ± 0.3 | 0.161 |
|   | Cholesterol | 387 ± 20 | 431 ± 23 | 398 ± 23 | 409 ± 8 | 0.455 |
|   | Triglyceride | 70 ± 3 | 80 ± 8 | 91 ± 4** | 102 ± 5* | 0.001 |
|   | Sinus Lesion μm² | 314764 ± 14458 | 307291 ± 22689 | 361166 ± 24068 | 334622 ± 26100 | 0.352 |

Note:
"Weight" is weight in grams;
"Cholesterol" is serum cholesterol and
"Triglyceride" is serum triglycerides, expressed in mg/dL.
*P < 0.001 versus the PBS group.
**P < 0.05 versus the PBS group.

As can be clearly seen in FIG. 24, while oral administration of the oxidized compounds CI-201 and ALLE substantially inhibited atherogenesis in Apo-E KO mice, no effect on atherogenesis was observed following treatment with the pre-oxidized derivative Compound V, thus indicating the importance of the presence of the oxidized group in treating atherogenesis.

Example XV

Oral Administration of the Pre-Oxidized Compound V to Genetically Predisposed (Apo-E KO) Mice The Effect of an Oxidized Group on Atherogenesis Progression The pre-oxidized Compound V was further tested in the prevention of progression model in ApoE KO mice, described hereinabove. 23-26 weeks old Apo-E KO mice (APO-E−/− <tm1Unc>[C57B/6J]) were stratified by age, weight and lipid profile (cholesterol and triglyceride) to different groups. One group was sacrificed at the beginning of the experiment and served as the "base line" group (B.L., n=10). The second group was treated with Compound V (0.1 μg/dose, n=10) dissolved in PBS, 0.05% ethanol, in a total volume of 0.2 ml PBS. The control group received PBS (0.05% ethanol, 0.2 ml) (n=11).

Mice were treated with compound V or PBS at three sets at the beginning of each month, each set consisted of 5 oral administrations every other day. All mice were fed normal chow-diet containing 4.5% fat by weight (0.02% cholesterol) and water ad libitum and were kept in a 12 hours dark/light cycle.

After 12 weeks, mice were sacrificed and evaluated for lipid profile and extent of atheromatous plaque area within the aortic sinus, as described herein above. The results are presented in Table 11 below and in FIG. 25 and clearly indicate that oral administration of Compound V did not effect atherogenesis progression.

TABLE 11

The effect of the pre-oxidized derivative Compound V on metabolic parameters and atherosclerosis area in the aortic sinus in ApoE KO mice

| Time point | Parameter | Comp. V 0.1 µg/dose | PBS | Base-Line | Statistics (p value) |
|---|---|---|---|---|---|
| T = 0 | Weight (g) | 26.1 ± 0.7 | 26.2 ± 0.6 | 26.2 ± 0.7 | 0.710 |
| | Cholesterol (mg/Dl) | 401 ± 27 | 393 ± 32 | 406 ± 19 | 0.936 |
| | Triglyceride (mg/Dl) | 128 ± 8 | 129 ± 6 | 125 ± 7 | 0.926 |
| END | Weight (g) | 28.1 ± 0.5 | 28.0 ± 0.5 | — | 0.967 |
| | Cholesterol (mg/Dl) | 292 ± 16 | 277 ± 37 | — | 0.717 |
| | Triglyceride (mg/Dl) | 81 ± 3 | 90 ± 4 | — | 0.094 |
| | Sinus Lesion µm$^2$ | 238156 ± 32206 | 206647 ± 15293 | 137451 ± 18975 | 0.011* |

*There is no statistical difference between the compound V treated mice and the control mice, PBS treated.

Example XVI

The In Vitro Effect of CI-201 on Dendritic Cells

Materials and Methods

Mice: Female 8-10 week old C67BL/6 and SJL mice were purchased from the Harlan laboratories, Israel.

Phospholipids: The molecules tested in vitro for inhibition of DC cytokine secretion were: 1-O-hexadecyl-2-(4'-carboxybutyl)-sn-glycero-3-phosphocholine [(R)—CI-201], (S)—CI-201, Racemic CI-201, Methyl ester of CI-201, Non-phosphorylated metabolite (NPM) of CI-201, 1-O-Hexadecyl-2-(5'-Hexenyl)-sn-glycero-3-phosphocholine (Compound V) and 1-O-Hexadecyl-2-(4'-carboxybutyl)-sn-Glycero-3-Phosphoethanolamine all were synthesized in VBL's chemical laboratory, Or Yehuda, Israel). 1-O-Hexadecyl-2-Acetoyl-sn-Glycero-3-Phosphocholine (PAF), L-α-Phosphatidylcholine, and Valeric acid were from Sigma-Aldrich (Rehovot, Israel). 1-Palmitoyl-2-(5'-oxo-Valeroyl)-sn-Glycero-3-Phosphocholine (POVPC), 1-Palmitoyl-2-Glutaroyl-sn-Glycero-3-Phosphocholine (PGPC), 1-O-Octadecyl-2-Acetoyl-sn-Glycero-3-Phosphocholine (C18 PAF), 1-O-Hexadecyl-2-O-Butyroyl-sn-Glycero-3-Phosphocholine (PAF-2C), 1-O-Palmitoyl-2-Acetoyl-sn-Glycero-3-Phosphocholine (PAF ester) and 1-O-Hexadecyl-2-Azelaoyl-sn-Glycero-3-Phosphocholine (azPC) were purchased from Avanti Polar Lipids (Alabaster, Ala.).

Isolation of bone-marrow derived dendritic cells (BM-DC's): Bone-marrow was flushed out with cold RPMI-1640 from mice femur and tibia. A cell suspension was prepared and erythrocytes were removed using red blood cell (RBC) lysis buffer (Beit Haemek, Israel). Cells were washed in phosphate buffer saline (PBS) (Beit Haemek, Israel), and incubated at 4° C. for 15 minutes in buffer containing PBS and 0.5% bovine serum albumin (BSA) with mouse B220 and CD90 microbeads (Miltenyi biotech, Bergisch Gladbach, Germany). Cells were then washed, resuspended in the same buffer, and depleted from B and T cells on a Midi-Macs separation unit through a LD or LS column (Miltenyi biotech). The depleted cells were then counted, washed and seeded (10$^6$/ml) in medium containing RPMI-1640, L-glutamine, β-mercaptoethanol, 10% FCS, antibiotics (Penicillin, Streptomycin) and 20 ng/ml of mouse GM-CSF (Peprotech, Rehovot, Israel). Medium was replaced every other day and cells were used for subsequent experiments on days 5-6 post culturing.

Isolation of Monocytes/Macrophages: Spleens were removed and a cell suspension was prepared. Erythrocytes were depleted using red blood cell (RBC) lysis buffer (Beit Haemek, Israel). Cells were washed in phosphate buffer saline (PBS) (Beit Haemek, Israel), and incubated in 4° C. for 15 min in buffer containing PBS and 0.5% bovine serum albumin (BSA) with mouse CD11b microbeads (Miltenyi biotech, Bergisch Gladbach, Germany). Cells were then washed, resuspended in the same buffer and positively selected on a Mini-Macs separation unit through a MS column (Miltenyi biotech).

Isolation of human monocyte derived dendritic cells (Mo-DC's): PBMCs were isolated from heparinized whole blood from healthy donors by Ficoll-Paque (Amersham, Uppsala, Sweden). Cells were incubated at 4° C. for 15 minutes in buffer containing PBS, 0.5% bovine serum albumin (BSA) and 2 mM EDTA with human CD14 microbeads (Miltenyi biotech) washed and positively selected on a Midi-Macs separation unit through LS column. The resulting cells were counted washed and seeded (10$^6$/ml) in medium containing RPMI-1640, L-glutamine, β-mercaptoethanol, 10% FCS, antibiotics (Penicillin, Streptomycin), non essential amino acids, sodium pyruvate, 40 ng/ml of human GM-CSF and 20 ng/ml of human IL-4 (R&D systems, Minneapolis, Minn.). Medium was replaced every other day and cells were used for subsequent experiments on days 5-6 post culturing. Cell purity was >75% as determined by FACS for CD11c.

Cytokine analysis: For the detection of cytokine production, supernatants from BMDC's and Mo-DC's following a 24 hour treatment were tested with Duoset ELISA kits for mouse IL12p40, TNF-α, IL-6 and human IL12p40 and TNF-α (R&D systems, Minneapolis, Minn.) respectively.

For measurement of IFN-γ by ex-vivo activated T cells, SJL female mice were orally administered with CI-201 (10 and 100 µg/mouse/feed) or PBS as control, once a day, every other day for a total of 5 doses (dosing volume was 0.2 ml) and then immunized subcutaneously in two flanks with 200 µl of emulsion containing 200 µg of PLP peptide 139-151 and 400 µg of MT followed by 4 more administrations every other day. Lymph nodes were collected 10 days later, stimulated ex vivo with 10 µg/ml of PLP 139-151 peptide or 0.5 µg/ml of anti CD3 and three days later cytokine production from the supernatant was measured using the Duoset ELISA kit (R&D systems, Minneapolis, Minn.).

Ex-vivo ELISA and Intracellular staining: For intracellular staining, C57BL/6 were orally administered with CI-201 (0.1 μg/mouse/feed) or PBS as control, 5 times, once every other day. Dosing volume was 0.2 ml. Subsequently, mice were immunized subcutaneously in two flanks with 200 μl of emulsion containing 200 μg of ovalbumin and MT (100 μg). Ten days later, during which alternate oral feedings of PBS and CI-201 were continued, mice were sacrificed, a cell suspension was prepared from the draining lymph nodes and cells were activated ex vivo with 1 mg/ml of ovalbumin. One week later, cells were re-stimulated with plate-bound anti CD3 and anti CD28 and tested for cytokine production by intracellular staining. Results are on gated CD4+ T cells. All antibodies used (IL-4-APC, IFN-γ-PE, TNF-α-APC, IL-10-PE, CD4-FITC) are from Pharmingen (San Diego, Calif.).

Preparation of RNA, cDNA and Quantitative Real Time PCR (Q-PCR): RNA was prepared from cells using RNeasy mini kit (Qiagen, Valencia, Calif.). For cDNA preparation, 1 μg of RNA was combined with Oligo dT for 10 minutes at 70° C., $1^{st}$ strand buffer, DTT and dNTP and super-script reverse transcriptase (SS-II) (Invitrogen, Carlsbad, Calif.) were added for 50 minutes at 42° C. and the reaction was ended by incubation for an additional 15 minutes at 70° C. All real time PCR reactions were performed using lightcycler Taqman master (Roche diagnostics, Mannheim, Germany) and run on the LightCycler machine (Roche). Q-PCR was done with a set of matched primers (Sigma-Genosys, Israel) and probes (Roche diagnostics, Mannheim, Germany) as was suggested in Roche's web site: www.roche-applied-science.com/servlet for mouse IL27p28 (5'-CATGGCATCACCTCTCTGAC, SEQ ID NO: 1), (3'-AAGGGCCGAAGTGTGGTAG, SEQ ID NO: 2), probe #38 Cat#04687965001, IL12p35 (5'-GAGACTTCTTCCACAACAAGAGG, SEQ ID NO: 3), (3'-CTACCAAGGCACAGGGTCAT, SEQ ID NO: 4) probe #27 cat#04687582001 and IL23p19 (5'-CACCAGCGGGA-CATATGAA, SEQ ID NO: 5), (3'-CCTTGTGGGTCA-CAACCAT, SEQ ID NO: 6), prone #47 cat#04688074001. Ready sets of probe with primer were used for IL12p40 and GAPDH assays (Applied Biosystems, assays #Mm01288992_ml and Mm99999915_g1 respectively) with the latter served to normalize RNA levels.

Cell stimulation: Mouse BMDC's were activated with 100 ng/ml *E. coli* LPS 05:55 (Sigma-Aldrich), 10 μg/ml peptidoglycan (PGN), 25 μg/ml Poly I:C, 300 ng/ml $Pam_3CSK4$ and 1 μg/ml Fc-soluble CD40L (InvivoGen, San Diego, Calif.). Cells were pre-incubated for 1 hour with various phospholipids at the indicated concentrations before activation with TLR ligands or Fc-soluble CD40L and supernatants collected 24 hours later. Human Mo-DC's were activated with PGN. For PBMC's and CD14+, cells were pre incubated with human IFN-γ (20 ng/ml) and maintained during a 24 hour activation. For RNA preparation, cells were pre incubated for 1 hour with 20 μg/ml of CI-201 and then activated for the indicated time points with PGN before collection. In the experiments conducted to determine potential active sites, phospholipids were added at the indicated concentrations 1 hour prior to activation with PGN.

Gene Chip analysis: Mouse BMDC's were enriched for CD11c+ DC (>90%) with mouse CD11c microbeads from 5-6 days cultures over MS or LS columns (Miltenyi biotech). CD11c+ DC were stimulated for 3 hours with 10 μg/ml PGN alone or in the presence of 20 μg/ml of CI-201. RNA was prepared and used to generate cRNA. Preparation of cRNA, hybridization and scanning was done in the Weizmann Institute of Science (Rehovot, Israel) on the mouse genome 430A 2.0 array (Affymetrix, Santa Clara, Calif.).

XV1A: CI-201 Inhibits IL12p40 but not TNF-α, IL-6 and IL-1 Production from Activated BMDC's As indicated above, oral administration of CI-201 reduces the level of IFN-γ messenger RNA in the aortas of ApoE−/− mice. As T cells are a major source of IFN-γ and Th1 cells were shown to play a role in atherosclerosis, the effect of CI-201 treatment on IFN-γ production by CD4+ T cells was assessed.

Results

The data presented in FIGS. 26A-B demonstrates that in vivo treatment with CI-201 resulted in reduced IFN-γ production by CD4+ T cells.

In light of the above, it was speculated that CI-201 might have a direct inhibitory effect on IFN-γ production by T cells. To address that, radiolabeled CI-201 was incubated with different immune cell lines and the level of incorporation was measured. Unexpectedly, the highest CI-201 incorporation was detected in DC's and macrophages, and not in T cells, which showed a mild increase in radioactive levels only at the 24 hours time point compared to control cells (FIG. 27). Accordingly, it was hypothesized that CI-201 impairs IFN-γ production by CD4+ T cells through regulation of IL12p40 (p40) secretion by APC's.

To test that, BMDC's were activated with several TLR antagonists in the presence of varying concentrations of CI-201. Supernatants collected 24 hours later were assayed for the production of p40 by ELISA. FIGS. 28A-F demonstrate that IL12p40 production was inhibited to various degrees by CI-201 treatment following activation of BMDC's with the different TLR ligands used. When BMDC'S were activated with PGN (TLR 2/6), a significant and dose dependent reduction in p40 production was observed (FIG. 28A), while activation with another TLR 2 ligand, Pam3CSK4 (TLR1/2) resulted in significant p40 inhibition (FIG. 28B).

The effect on p40 production was then tested following activation with LPS, an agonist to TLR4 that signals downstream through both Myd88 dependent and independent pathways. A significant, but small reduction of p40 levels were detected in the presence of intermediated concentrations of CI-201 (FIG. 28C).

Next, the effect of CI-201 on p40 production from DC's activated through intracellular TLR was investigated. While a significant and dose dependent p40 inhibition with CI-201 could be noticed following PolyI:C (TLR3) activation (Myd88 independent) (FIG. 28D), only 20 μg/ml of CI-201 was able to significantly inhibit p40 secretion after CpG (TLR9) engagement (FIG. 28E). To determine whether CI-201 conveys its inhibitory function via interfering with TLR binding, BMDC's were activated with Fc-CD40L. This induces cytokine production by BMDC's in a TLR, MyD88-independent pathway. As shown in FIG. 28F, Fc-CD40L activation in the presence of CI-201 resulted in a significant reduction of p40 secretion by BMDC's.

Because activation of BMDC's through TLR's and CD40 is known to induce the production of cytokines other than p40, TNF-α levels were measured following activation with all TLR agonists used above. In addition, IL-6 and IL-1 levels were also measured following PGN DC's activation in the presence of CI-201. The results presented in FIGS. 28G-M demonstrate that except for PolyI:C, CI-201 did not impair the production of TNF-α by other activators, and likewise did not impair the production of IL-6 and IL-1 following PGN activation of BMDC's. Taken together, these results suggest that CI-201 impedes a particular pathway responsible for the induction of p40 production while leaving pathways regulating acute proinflammatory cytokine production unaffected.

XV1B: Gene Chip and Real-Time PCR Analysis

In order to determine p40's level of regulation and to reveal putative additional modified genes subsequent to CI-201 treatment, gene chip analysis was conducted on purified CD11c+ BMDC's activated for 3 hours with PGN in the presence of CI-201.

Results

Figure 29A:
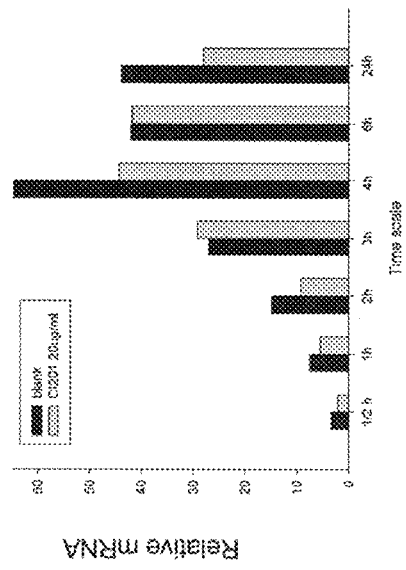
Figure 29B:
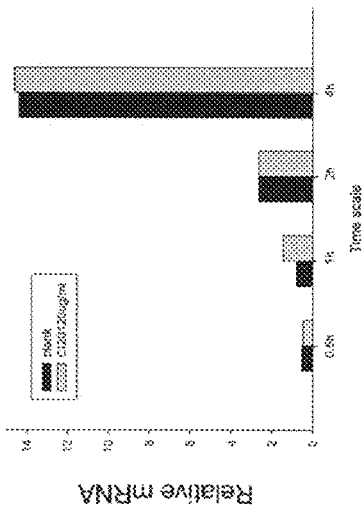
Figure 29C:
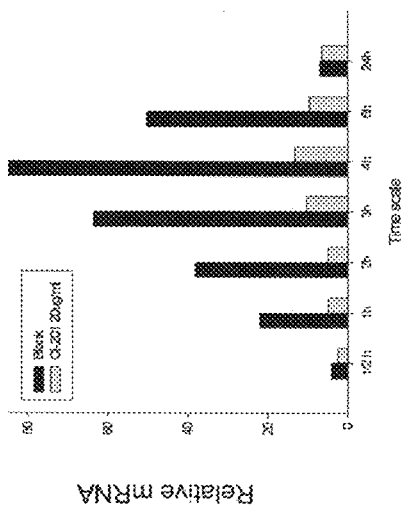
Figure 29D:
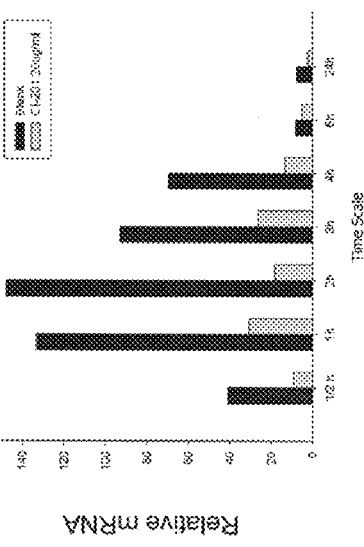

Several genes were found to be up-regulated and 5 genes, including p40 had a reduced RNA expression. In order to confirm the gene chip results and examine p40's regulation kinetics by CI-201, quantitative real time PCR was performed for p40 and for the paired chains constituting IL12(p35), IL-23(p19) and IL-27(p28) with the latter recently shown to play a role in IFN-γ production by T cells as well. Similar to the results obtained from the gene chip analysis, CI-201 clearly inhibited p40 RNA expression in the first 6 hours following activation (FIG. 29A) by more than two folds compared to control. It was also discovered that treatment with CI-201 resulted in a substantial inhibition of the RNA expression level of p19 (FIG. 29C). Following reevaluation of the gene chip results, a reduced p19 expression in the CI-201 treated cells was indeed observed, thereby confirming the real time PCR results. CI-201 did not modify the RNA expression levels of p35 and p28 (FIGS. 29B and 29D). These results indicate that CI-201 regulates the RNA expression levels of IL-12 and IL-23, two key pro-inflammatory cytokines shown to play a pivotal role in inflammatory diseases.

XV1C: CI-201 Alters p40 Production by Mo-DC

Since CI-201 leads to the reduction of p40 expression from activated BMDC's the effect of CI-201 on human cells was also examined. Mo-DC's were activated with PGN in the presence of CI-201 and the supernatants were tested for p40 and TNF-α production.

Results

The results depicted in FIG. 30A indicate that CI-201 can inhibit p40 production by activated Mo-DC's without altering the cells ability to produce TNF-α (FIG. 30B).

XV1C: CI-201 Inhibits p40 Production by PBMC but not by Monocytes/Macrophages

The data presented above clearly demonstrate that CI-201 can regulate p40 production by DC's. The next experiment was performed in order to test whether p40 inhibition could be detected when CI-201 is applied on total PBMC's and monocytes/macrophages.

Results

Figure 31A:
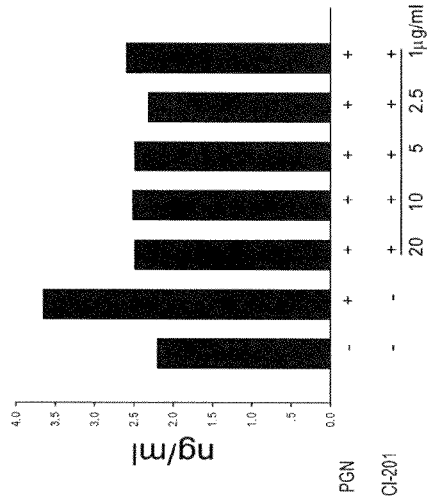
Figure 31B:
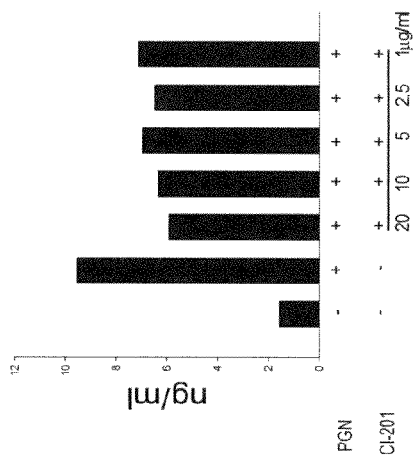
Figure 31C:
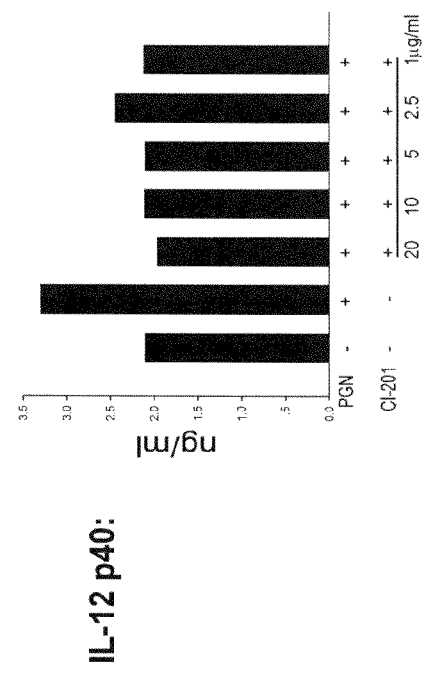
Figure 31D:
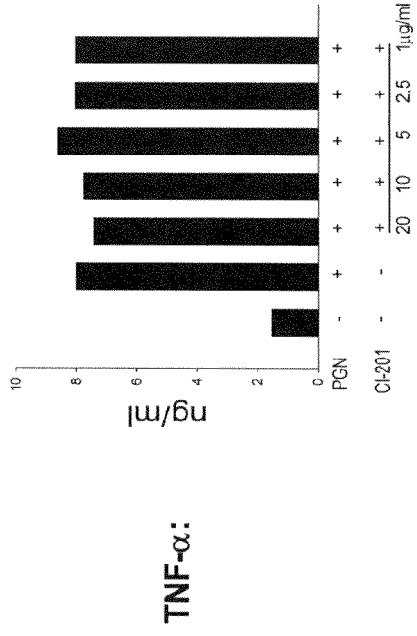

PBMC's from healthy donors were incubated over-night with IFN-γ and then activated with PGN in the presence of CI-201 for another 24 hours. Supernatants were then evaluated for p40 and TNF-α production. As observed with DC's, CI-201 inhibited p40 production when applied to PGN activated PBMC's from two different donors. However, unlike with DC's, a close to complete inhibition of p40 production could be achieved in all CI-201's tested concentrations (FIGS. 31A-B). In agreement with the DC data above, CI-201 did not impair TNF-α production by PBMC's from donor I while a modest reduction in TNF-α levels was measured from donor II PBMC's (FIGS. 31C-D).

In order to assess CI-201 effect on p40 production by macrophages, splenic CD 11b cells were incubated over night with IFN-γ and then activated for 24 hours with PGN in the presence CI-201. When supernatants were evaluated for p40, no major differences in p40 and TNF-α production levels were observed between control and CI-201 treated cells suggesting that CI-201 may selectively act on DC's (FIGS. 32A-B).

XV1D: Structure-Function Studies with CI-201

The in vitro experiments described hereinabove demonstrated that p40 production by activated DC's could be maximally inhibited by the highest concentration of CI-201 used (20 μg/ml). However, based on previous experience with small molecules designed for therapeutic applications, it is highly desirable to reach beneficial effect with lower substance concentration in the range of ng/ml. Therefore, it was a priority to design a superior molecule on the backbone of CI-201 that will exhibit similar in vitro effect on p40 production when applied to DC's. To attain such a molecule, it is important to establish the residue/s which are essential for CI-201's functionality.

Results

Figure 33H:
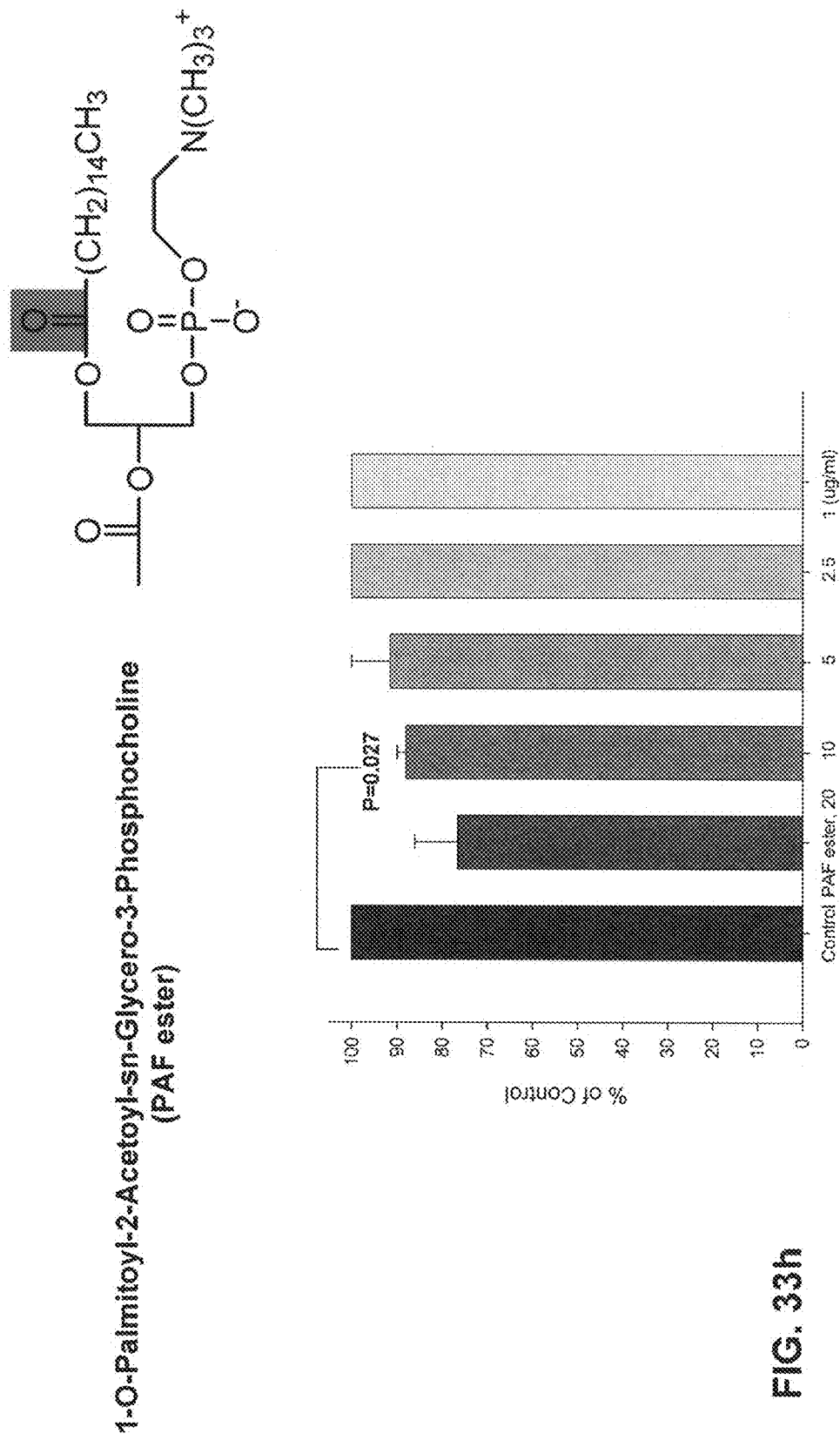
Figure 33I:
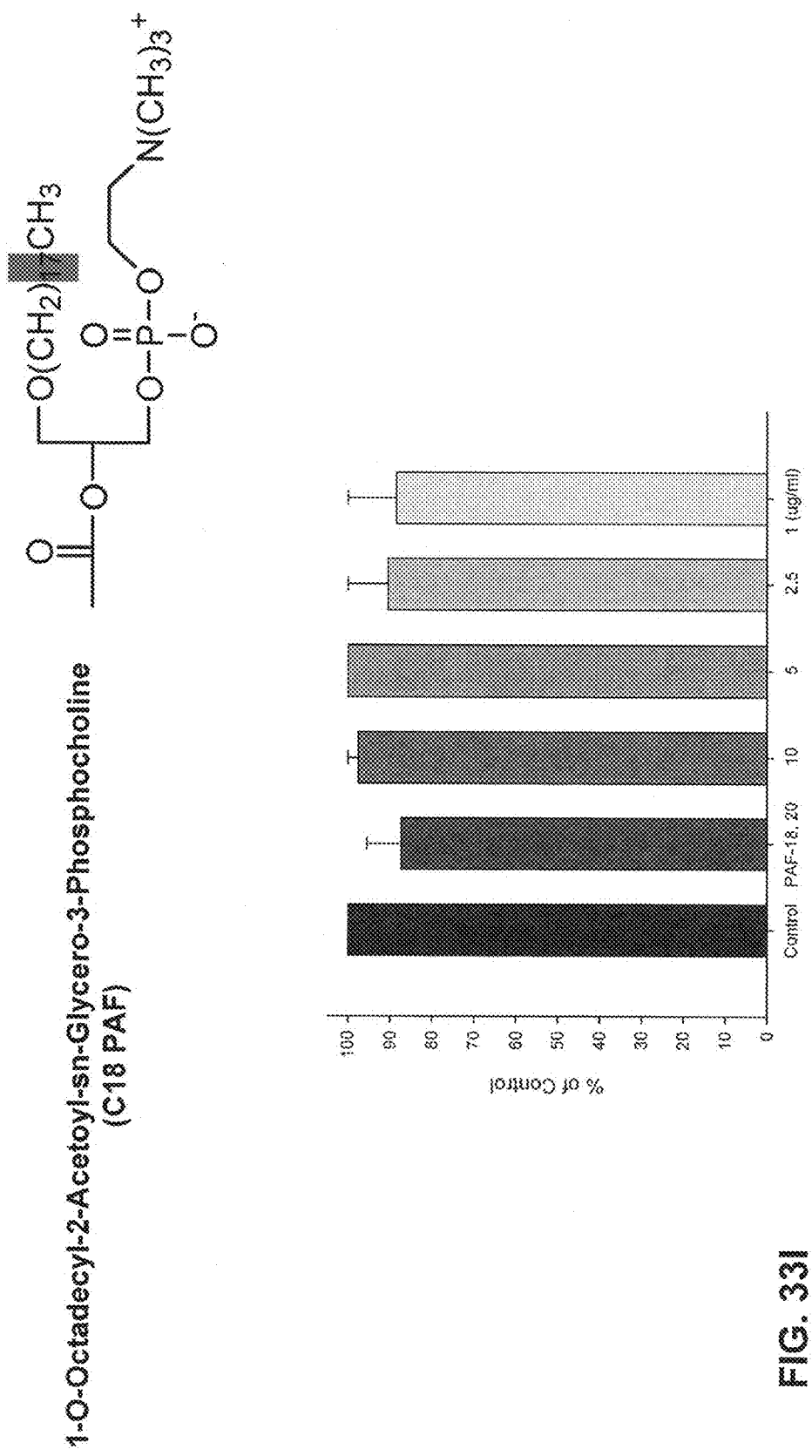

In a set of experiments, BMDC's were activated with PGN in the presence of commercially available and self synthesized oxidized and non oxidized phospholipids, with p40 production levels placed as the measured parameter to determine inhibitory efficacy. Preliminary results indicated that several facets such as the length, the chemical composition and the chemical bonds of each chain should be considered in future molecular designs. Thus, replacement of the hydrogen group for a methyl group in R2 (methyl ester of CI-201) and removal of the phosphocholine group in R3 (non phosphorylated metabolite of CI-201) restored p40 production (FIGS. 33B-C). Nonetheless, exchange of the three methyl groups in R3 for three hydrogen molecules (phosphoethanol amine) did not alter the molecule's p40 inhibitory effect (FIG. 33D). A group of molecules, some closely resembling the structure of CI-201 (POVPC and PVPC), were tested, all bearing an esteric bond on R1 and R2 instead of the etheric bonds found in CI-201. A third group of molecules was also selected for testing that were derived from PAF, which has some similarities to CI-201. It was found that PAF itself and PAF2C with an extended R2 molecule were efficient in p40 inhibition (FIGS. 33H-I). Shortening of R2 mildly reduced the activity of PAF (FIG. 33K), but an additional esteric bond in R1, elongation by 2 methyl group of R2 or a long R2 with oxidized edge, all resulted in loss of p40 inhibition (FIGS. 33L-M).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

ADDITIONAL REFERENCES OF INTEREST

Not Cited within the Text

Wick G, Schett G, Amberger A, Kleindienst R, Xu Q. Is atherosclerosis an immunologically mediated disease? Immunol Today 1995; 16: 27-33.

Libby P, Hansson G K. Involvement of the immune system in human atherogenesis: current knowledge and unanswered questions. Lab Invest 1991; 64: 5-15

Steinberg D, Parathasarathy S, Carew T E, Khoo J C, Witztum J L. Beyond cholesterol. Modifications of low-density lipoprotein that increase its atherogenicity. N Engl J Med 1989; 320: 915-924.

Witztum J. The oxidation hypothesis of atherosclerosis. Lancet 1994; 344: 793-795.

Palinski W, Miller E, Witztum J L. Immunization of low density lipoprotein (LDL) receptor-deficient rabbits with homologous malondialdehyde-modified LDL reduces atherogenesis. Proc Natl Acad Sci USA. 1995; 92: 821-825.

George J, Afek A, Gilburd B, Levy Y, Levkovitz H, Shaish A, Goldberg I, Kopolovic Y, Wick G, Shoenfeld Y, Harats D. Hyperimmunization of ApoE deficient mice with homologous oxLDL suppresses early atherogenesis. Atherosclerosis. 1998; 138: 147-152.

Weiner H, Freidman A, Miller A. Oral tolerance: immunologic mechanisms and treatment of animal and human organ specific autoimmune diseases by oral administration of autoantigens. Annu Rev Immunol 1994; 12: 809-837.

Palinski W, Ord V A, Plump A S, Breslow J L, Steinberg D, Witztum J L. Apo-E-deficient mice are a model of lipoprotein oxidation in atherogenesis. Demonstration of oxidation-specific epitopes in lesions and high titers of autoantibodies to malondialdehyde-lysine in serum. Arterioscler Thromb 1994; 14: 605-616

Roselaar S E, Kakkanathu P X, Daugherty A. Lymphocyte populations in atherosclerotic lesions of apo-E−/− and LDL receptor−/− mice; Decreasing density with disease progression. Arterioscler Thromb Vasc Biol 1996; 16: 1013-1018.

Palinski W, Yla-Herttuala S, Rosenfeld M E, Butler S W, Socher S A, Parthasarathy S, Curtiss L K, Witztum J L. Antisera and monoclonal antibodies specific for epitopes generated during oxidative modification of low density lipoprotein. Arteriosclerosis 1990; 10: 325-335.

Ou Z., Ogamo A., Guo L., Konda Y., Harigaya Y. and Nakagawa Y. Anal. Biochem. 227: 289-294, 1995.

E. Baer and Buchnea JBC. 230,447, 1958.

Quintana F J, Carmi P, Mor F and Cohen R. Inhibition of adjuvant arthritis by a DNA vaccine encoding human heat shock protein 60. J. Immunol. 2002; 169:3422-3428.

Cobelens P M, Heijnen C J, Nieuwenhois E E S et al. Treatment of adjuvant induced arthritis by oral administration of mycobacterial Hsp65 during disease. Arthritis Rheum. 2000; 43(12):2694-2702.

Cobelens P M, Kavelaars A, Van Der Zee R et al. Dynamics of mycobacterial HSP65-induced T-cell cytokine expression during oral tolerance induction in adjuvant arthritis. Rheumatology. 2002; 41:775-779.

What is claimed is:

1. A method of treating an inflammation associated with an endogenous oxidized lipid, said inflammation being associated with a disease selected from the group consisting of psoriasis, rheumatoid arthritis, inflammatory bowel disease, multiple sclerosis and atherosclerosis, the method comprising administering to a subject in need thereof a therapeutically effective amount of at least one oxidized lipid having the general formula I:

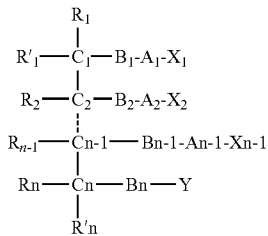

Formula I wherein:
n is an integer of 1-6, whereas if n=1, Cn, Bn, Rn and Y are absent;
each of $B_1, B_2, \ldots Bn-1$ and Bn is independently selected from the group consisting of oxygen, sulfur, nitrogen, phosphorus and silicon, whereby each of said nitrogen, phosphorus and silicon is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo;
each of $A_1, A_2, \ldots An-1$ and An is independently selected from the group consisting of CR"R'", C=O and C=S,
Y is selected from the group consisting of hydrogen, alkyl, aryl, cycloalkyl, carboxy, saccharide, phosphoric acid, phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-biphosphonate, pyrophosphate, phosphoethanolamine-diethylenetriamine-pentaacetate, dinitrophenyl-phosphoethanolamine and phosphoglycerol; and
each of $X_1, X_2, \ldots Xn-1$ is independently a saturated or unsaturated hydrocarbon having the general formula II:

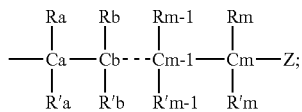

Formula II wherein:
m is an integer of 1-26; and
Z is selected from the group consisting of:

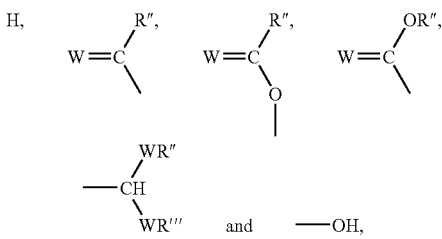

whereas W is selected from the group consisting of oxygen, sulfur, nitrogen and phosphorus, whereby each of said nitrogen and phosphorus is substituted by at least one substituent selected from the group consisting of hydrogen, lone pair electrons, alkyl, halo, cycloalkyl, aryl, hydroxy, thiohydroxy, alkoxy, aryloxy, thioaryloxy, thioalkoxy and oxo; and
at least one of $X_1, X_2, \ldots Xn-1$ comprises a Z different than hydrogen and wherein:

each of $R_1$, $R'_1$, $R_2$, ... $Rn-1$, $Rn$, $R'n$, each of R" and R'" and each of Ra, R'a, Rb, R'b, ... Rm-1, R'm-1, Rm and R'm is independently selected from the group consisting of hydrogen, a bond, alkyl, alkenyl, alkylnyl, cycloalkyl, aryl, heteroaryl, halo, trihalomethyl, hydroxy, alkoxy, aryloxy, thiohydroxy, thioalkoxy, thioaryloxy, phosphonate, phosphate, phosphinyl, sulfonyl, sulfinyl, sulfonamide, amide, carbonyl, thiocarbonyl, C-carboxy, O-carboxy, C-carbamate, N-carbamate, C-thiocarboxy, S-thiocarboxy and amino, or, alternatively, at least two of $R_1$, $R'_1$, R2, ... Rn-1, Rn and R'n and/or at least two of Ra, R'a, Rb, R'b, ... Rm-1, R'm-1, Rm and R'm form at least one four-, five- or six-membered aromatic, heteroaromatic, alicyclic or heteroalicyclic ring; and each of $C_1$, $C_2$, ..., $Cn-1$, $Cn$, and each of Ca, Cb, ... Cm-1 and Cm is a chiral or non-chiral carbon atom, whereby each chiral carbon atom has a S-configuration and/or a R-configuration, a pharmaceutically acceptable salt, a prodrug, a hydrate or a solvate thereof, thereby treating the inflammation associated with an endogenous oxidized lipid in said subject.

2. The method of claim 1, wherein at least one of $A_1$, $A_2$, ... and $An-1$ is CR"R'".

3. The method of claim 2, wherein at least one of said at least one of $A_1$, $A_2$, ... and $An-1$ is linked to a $X_1$, $X_2$ ... or $Xn-1$ which comprises a Z different than hydrogen.

4. The method of claim 1, wherein n equals 3.

5. The method of claim 4, wherein at least one of $A_1$ and $A_2$ is CR"R'".

6. The method of claim 5, wherein $A_2$ is CR"R'".

7. The method of claim 5, wherein each of $A_1$ and $A_2$ is CR"R'".

8. The method of claim 4, wherein $X_2$ comprises a Z different than hydrogen.

9. The method of claim 8, wherein said Z is selected from the group consisting of

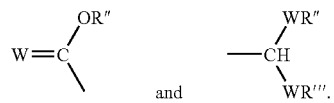

10. The method of claim 9, wherein W is oxygen and each of R" and R'" is independently selected from the group consisting of hydrogen and alkyl.

11. The method of claim 10, wherein:
each of $A_1$ and $A_2$ is CR"R'";
each of $B_1$, $B_2$ ... Bn is oxygen;
$X_1$ is a saturated hydrocarbon having said general formula II, whereas Z is hydrogen;
$X_2$ is a saturated hydrocarbon having said general Formula II, whereas said Z is

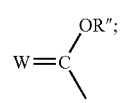

and
Y is phosphoryl choline.

12. The method of claim 11, wherein:
$X_1$ is said saturated hydrocarbon having said general formula II, whereas Z is hydrogen and m equals 15; and $X_2$ is a saturated hydrocarbon having said general Formula II, whereas m equals 3.

13. The method of claim 11, wherein each of $R_1$, $R'_1$, $R_2$, ... $Rn-1$, $Rn$, $R'n$, each of R" and R'" and each of Ra, R'a, Rb, R'b, ... Rm-1, R'm-1, Rm and R'm is hydrogen.

14. The method of claim 13, wherein $C_2$ is a chiral carbon atom which has a S-configuration or a R-configuration.

15. The method of claim 13, wherein said oxidized lipid is selected from the group consisting of 1-Hexadecyl-2-(4'-Carboxy-butyl)-sn-glycero-3-phosphocholine and 3-Hexadecyl-2-(4'-Carboxy-butyl)-sn-glycero-1-phosphocholine.

16. The method of claim 13, wherein said oxidized lipid has the formula:

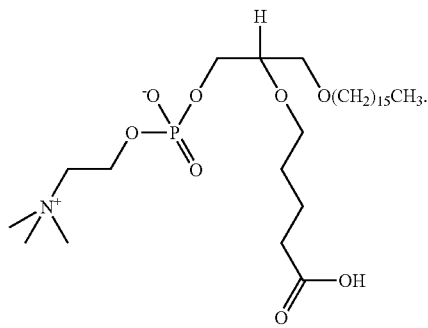

17. The method of claim 13, wherein said oxidized lipid has the formula:

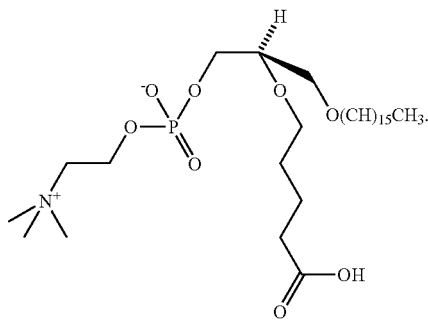

18. The method of claim 1, wherein n equals 1.

19. The method of claim 18, wherein at least one of $R_1$ and $R'_1$ is a phosphate or a phosphonate.

20. The method of claim 1, wherein n equals 5 or 6, and at least one of $R_1$, $R'_1$ and at least one of Rn and R'n form at least one heteroalicyclic ring.

21. The method of claim 20, wherein said at least one heteroalicyclic ring is a monosaccharide ring.

22. The method of claim 1, wherein said oxidized lipid is selected from the group consisting of: 1-palmitoyl-2-azelaoyl-sn-glycero-3-phosphocholine, 1-hexadecyl-2-azelaoyl-sn-glycero-3-phosphocholine, 1-palmitoyl-2-glutaroyl-sn-glycero-3-phosphocholine (PGPC), 1-palmitoyl-2-(5-oxovaleroyl)-sn-glycero-3-phosphocholine (POVPC), 1-palmitoyl-2-(9-oxononanoyl)-sn-glycero-3-phosphocholine, 1-hexadecyl-2-acetoyl-sn-glycero-3-phosphocholine, 1-octadecyl-2-acetoyl-sn-glycero-3-phosphocholine, 1-hexadecyl-2-butyroyl-sn-glycero-3-phosphocholine, 1-octadecyl-2-butyroyl- sn-glycero-3-phosphocholine, 1-palmitoyl-2-acetoyl-sn-glycero-3-phosphocholine, 1-octadecenyl-2-acetoyl-sn-glycero-3-phosphocholine, 1-hexadecyl-2-(homogammalinolenoyl)-sn-glycero-3-phosphocholine, 1-hexadecyl-2-arachidonoyl-sn-glycero-3-phosphocholine, 1-hexadecyl-2-eicosapentaenoyl-sn-glycero-3-phosphocholine, 1-hexadecyl-2-docosahexaenoyl-sn-glycero-3-phosphocholine, 1-octadecyl-2-methyl-sn-glycero-3-phosphocholine, 1-hexadecyl-2-butenoyl- sn-glycero-3-phosphocholine, Lyso PAF C16, Lyso PAF C18, 1-O-1'-(Z)-hexadecenyl-2-[12-[(7-nitro-2-1,3-benzoxadiazol-4-yl)amino]dodecanoyl]-sn-glycero-3-phosphocholine, 1-O-1'-(Z)-hexadecenyl-2-oleoyl-sn-glycero-3-phosphocholine, 1-O-1' -(Z)-hexadecenyl-2-arachidonoyl-sn-glycero-3-phosphocholine, 1-O-1'-(Z)-hexadecenyl-2-docosahexaenoyl-sn-glycero-3-phosphocholine, 1-O-1'-(Z)-hexadecenyl-2-oleoyl- sn-glycero-3-phosphoethanolamine, 1-O-1'-(Z)-hexadecenyl-2-arachidonoyl-sn-glycero-3-phosphoethanolamine, and 1-O-1'-(Z)-hex adecenyl-2-doco s ahexaenoyl-sn-glycero-3-phosphoethanolamine.

23. The method of claim 1, further comprising administering to said subject a therapeutically effective amount of at least one additional compound capable of treating said inflammation.

24. The method of claim 23, wherein said at least one additional compound is selected from the group consisting of a HMGCoA reductase inhibitor (a statin), a mucosal adjuvant, a corticosteroid, a steroidal anti-inflammatory drug, a non-steroidal anti-inflammatory drug, an analgesic, a growth factor, a toxin, a HSP, a Beta-2-glycoprotein I, a cholesteryl ester transfer protein (CETP) inhibitor, a perixosome proliferative activated receptor (PPAR) agonist, an anti-atherosclerosis drug, an anti-proliferative agent, ezetimide, nicotinic acid, a squalen inhibitor, an ApoE Milano, and any derivative and analog thereof.

25. A method of treating an inflammation associated with an endogenous oxidized lipid, the method comprising administering to a subject in need thereof a therapeutically effective amount of an oxidized lipid having the formula:

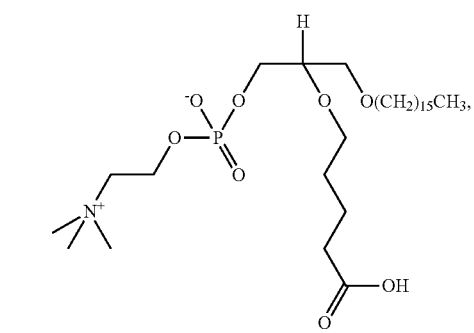

a pharmaceutically acceptable salt, a prodrug, a hydrate or a solvate thereof, thereby treating the inflammation associated with an endogenous oxidized lipid in said subject.

26. The method of claim 25, wherein said oxidized lipid has the formula:

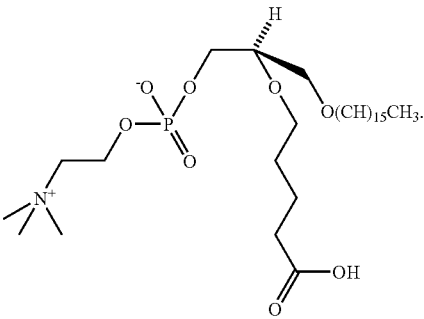

27. The method of claim 25, wherein said inflammation is associated with a disease selected from the group consisting of an idiopathic inflammatory disease, a chronic inflammatory disease, an acute inflammatory disease, an autoimmune disease, an infectious disease, an inflammatory malignant disease, an inflammatory transplantation-related disease, an inflammatory degenerative disease, a disease associated with a hypersensitivity, an inflammatory cardiovascular disease, an inflammatory cerebrovascular disease, a peripheral vascular disease, an inflammatory glandular disease, an inflammatory gastrointestinal disease, an inflammatory cutaneous disease, an inflammatory hepatic disease, an inflammatory neurological disease, an inflammatory musculo-skeletal disease, an inflammatory renal disease, an inflammatory reproductive disease, an inflammatory systemic disease, an inflammatory connective tissue disease, an inflammatory tumor, necrosis, an inflammatory implant-related disease, an inflammatory aging process, an immunodeficiency disease and an inflammatory pulmonary disease.

28. The method of claim 27, wherein said hypersensitivity is selected from the group consisting of Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity, delayed type hypersensitivity, helper T lymphocyte mediated hypersensitivity, cytotoxic T lymphocyte mediated hypersensitivity, TH1 lymphocyte mediated hypersensitivity, and TH2 lymphocyte mediated hypersensitivity.

29. The method of claim 27, wherein said inflammatory cardiovascular disease is selected from the group consisting of an occlusive disease, atherosclerosis, a cardiac valvular disease, stenosis, restenosis, in-stent-stenosis, myocardial infarction, coronary arterial disease, acute coronary syndromes, congestive heart failure, angina pectoris, myocardial ischemia, thrombosis, Wegener's granulomatosis, Takayasu's arteritis, Kawasaki syndrome, anti-factor VIII autoimmune disease, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity, Chagas' disease, and anti-helper T lymphocyte autoimmunity.

30. The method of claim 27, wherein said cerebrovascular disease is selected from the group consisting of stroke, cerebrovascular inflammation, cerebral hemorrhage and vertebral arterial insufficiency.

31. The method of claim 27, wherein said peripheral vascular disease is selected from the group consisting of gangrene, diabetic vasculopathy, ischemic bowel disease, thrombosis, diabetic retinopathy and diabetic nephropathy.

32. The method of claim 27, wherein said autoimmune disease is selected from the group consisting of chronic rheumatoid arthritis, juvenile rheumatoid arthritis, systemic lupus erythematosus, scleroderma, mixed connective tis sue disease, polyarteritis nodosa, polymyositis/dermatomyositis, Sjogren's syndrome, Bechet's disease, multiple sclerosis, autoimmune diabetes, Hashimoto's disease, psoriasis, primary myxedema, pernicious anemia, myasthenia gravis, chronic active hepatitis, autoimmune hemolytic anemia, idiopathic thrombocytopenic purpura, uveitis, vasculitides and heparin induced thrombocytopenia.

33. The method of claim 27, wherein said inflammatory glandular disease is selected from the group consisting of pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome.

34. The method of claim 27, wherein said inflammatory gastrointestinal disease is selected from the group consisting of colitis, ileitis, Crohn's disease, chronic inflammatory intestinal disease, inflammatory bowel syndrome, chronic inflammatory bowel disease, celiac disease, ulcerative colitis, an ulcer, a skin ulcer, a bed sore, a gastric ulcer, a peptic ulcer, a buccal ulcer, a nasopharyngeal ulcer, an esophageal ulcer, a duodenal ulcer and a gastrointestinal ulcer.

35. The method of claim 27, wherein said inflammatory cutaneous disease is selected from the group consisting of acne, autoimmune bullous skin disease, pemphigus vulgaris, bullous pemphigoid, pemphigus foliaceus, contact dermatitis and drug eruption.

36. The method of claim 27, wherein said inflammatory hepatic disease is selected from the group consisting of autoimmune hepatitis, hepatic cirrhosis, and biliary cirrhosis.

37. The method of claim 27, wherein said inflammatory neurological disease is selected from the group consisting of multiple sclerosis, Alzheimer's disease, Parkinson's disease, myasthenia gravis, motor neuropathy, Guillain-Barre syndrome, autoimmune neuropathy, Lambert-Eaton myasthenic syndrome, paraneoplastic neurological disease, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, Huntington's disease, AIDS associated dementia, amyotrophic lateral sclerosis (AML), multiple sclerosis, stroke, an inflammatory retinal disease, an inflammatory ocular disease, optic neuritis, spongiform encephalopathy, migraine, headache, cluster headache, and stiff-man syndrome.

38. The method of claim 27, wherein said inflammatory connective tissue disease is selected from the group consisting of autoimmune myositis, primary Sjogren's syndrome, smooth muscle autoimmune disease, myositis, tendinitis, a ligament inflammation, chondritis, a joint inflammation, a synovial inflammation, carpal tunnel syndrome, arthritis, rheumatoid arthritis, osteoarthritis, ankylosing spondylitis, a skeletal inflammation, an autoimmune ear disease, and an autoimmune disease of the inner ear.

39. The method of claim 27, wherein said inflammatory renal disease is autoimmune interstitial nephritis and/or renal cancer.

40. The method of claim 27, wherein said inflammatory reproductive disease is repeated fetal loss, ovarian cyst, or a menstruation associated disease.

41. The method of claim 27, wherein said inflammatory systemic disease is selected from the group consisting of systemic lupus erythematosus, systemic sclerosis, septic shock, toxic shock syndrome, and cachexia.

42. The method of claim 27, wherein said infectious disease is selected from the group consisting of a chronic infectious disease, a subacute infectious disease, an acute infectious disease, a viral disease, a bacterial disease, a protozoan disease, a parasitic disease, a fungal disease, a mycoplasma disease, gangrene, sepsis, a prion disease, influenza, tuberculosis, malaria, acquired immunodeficiency syndrome, and severe acute respiratory syndrome.

43. The method of claim 27, wherein said inflammatory transplantation-related disease is selected from the group consisting of graft rejection, chronic graft rejection, subacute graft rejection, acute graft rejection hyperacute graft rejection, and graft versus host disease.

44. The method of claim 27, wherein said inflammatory tumor is selected from the group consisting of a malignant tumor, a benign tumor, a solid tumor, a metastatic tumor and a non-solid tumor.

45. The method of claim 27, wherein said inflammatory pulmonary disease is selected from the group consisting of asthma, allergic asthma, emphysema, chronic obstructive pulmonary disease, sarcoidosis and bronchitis.

46. The method of claim 25, further comprising administering to said subject a therapeutically effective amount of at least one additional compound capable of treating said inflammation.

47. The method of claim 46, wherein said at least one additional compound is selected from the group consisting of a HMGCoA reductase inhibitor (a statin), a mucosal adjuvant, a corticosteroid, a steroidal anti-inflammatory drug, a non-steroidal anti-inflammatory drug, an analgesic, a growth factor, a toxin, a HSP, a Beta-2-glycoprotein I, a cholesteryl ester transfer protein (CETP) inhibitor, a peroxisome proliferative activated receptor (PPAR) agonist, an anti-atherosclerosis drug, an anti-proliferative agent, ezetimide, nicotinic acid, a squalen inhibitor, an ApoE Milano, and any derivative and analog thereof.

48. A method of treating an inflammation associated with an endogenous oxidized lipid, said inflammation being associated with a disease selected from the group consisting of psoriasis, rheumatoid arthritis, inflammatory bowel disease, multiple sclerosis and atherosclerosis, the method comprising administering to a subject in need thereof a therapeutically effective amount of an oxidized lipid having the formula:

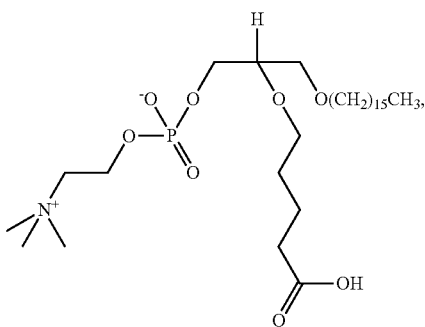

a pharmaceutically acceptable salt, a prodrug, a hydrate or a solvate thereof, thereby treating the inflammation associated with an endogenous oxidized lipid in said subject.

49. The method of claim 48, wherein said oxidized lipid has the formula:

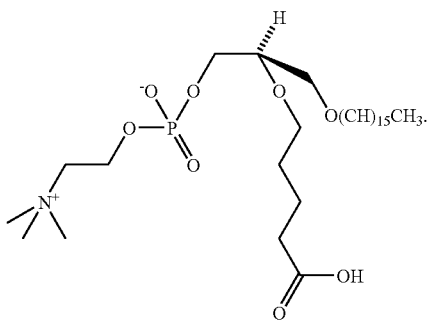

50. The method of claim 48, further comprising administering to said subject a therapeutically effective amount of at least one additional compound capable of treating said inflammation.

51. The method of claim 46, wherein said at least one additional compound is selected from the group consisting of a HMGCoA reductase inhibitor (a statin), a mucosal adjuvant, a corticosteroid, a steroidal anti-inflammatory drug, a non-steroidal anti-inflammatory drug, an analgesic, a growth factor, a toxin, a HSP, a Beta-2-glycoprotein I, a cholesteryl ester transfer protein (CETP) inhibitor, a peroxisome proliferative activated receptor (PPAR) agonist, an anti-atherosclerosis drug, an anti-proliferative agent, ezetimide, nicotinic acid, a squalen inhibitor, an ApoE Milano, and any derivative and analog thereof.

* * * * *

```
                        SEQUENCE LISTING

<160> NUMBER OF SEQ ID NOS: 6

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
catggcatca cctctctgac                                                    20

<210> SEQ ID NO 2
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 2
aagggccgaa gtgtggtag                                                     19

<210> SEQ ID NO 3
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 3
gagacttctt ccacaacaag agg                                                23

<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotide
```

```
<400> SEQUENCE: 4
ctaccaaggc acagggtcat                                          20

<210> SEQ ID NO 5
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 5
caccagcggg acatatgaa                                           19

<210> SEQ ID NO 6
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 6
ccttgtgggt cacaaccat                                           19
```